US012065702B2

(12) United States Patent
Barrachina Castillo et al.

(10) Patent No.: US 12,065,702 B2
(45) Date of Patent: **\*Aug. 20, 2024**

(54) MITOCHONDRIAL MARKERS OF NEURODEGENERATIVE DISEASES

(71) Applicants:FUNDACIÓ INSTITUT D'INVESTIGACIÓ BIOMÈDICA DE BELLVITGE (IDIBELL) S.A., Hospitalet de Llobregat (ES); UNIVERSITAT DE BARCELONA, Barcelona (ES)

(72) Inventors: Marta Barrachina Castillo, Hospitalet de Llobregat-Barcelona (ES); Isidre Ferrer Abizanda, Hospitalet de Llobregat-Barcelona (ES); Marta Blanch Lozano, Hospitalet de Llobregat-Barcelona (ES)

(73) Assignees: FUNDACIÓ INSTITUT D'INVESTIGACIÓ BIOMÉDICA DE BELLVITGE (IDIBELL) S.A., Hospitalet De Llobregat (ES); UNIVERSITAT DE BARCELONA, Barcelona (ES)

( * ) Notice: Subject to any disclaimer, the term of this patent is extended or adjusted under 35 U.S.C. 154(b) by 0 days.

This patent is subject to a terminal disclaimer.

(21) Appl. No.: 17/337,355

(22) Filed: Jun. 2, 2021

(65) Prior Publication Data

US 2022/0049307 A1 Feb. 17, 2022

Related U.S. Application Data

(63) Continuation of application No. 15/300,248, filed as application No. PCT/ES2015/070230 on Mar. 27, 2015, now Pat. No. 11,053,549.

(30) Foreign Application Priority Data

Mar. 28, 2014 (ES) ............................... ES201430444

(51) Int. Cl.
*C12Q 1/6883* (2018.01)
(52) U.S. Cl.
CPC ...... *C12Q 1/6883* (2013.01); *C12Q 2600/118* (2013.01); *C12Q 2600/154* (2013.01); *C12Q 2600/156* (2013.01)

(58) Field of Classification Search
None
See application file for complete search history.

(56) References Cited

U.S. PATENT DOCUMENTS

2004/0029133 A1 2/2004 Herrnstadt
2012/0232016 A1 9/2012 Coleman

FOREIGN PATENT DOCUMENTS

| JP | 2005-000044 A1 | 1/2005 |
| WO | 98/38334 A1 | 9/1998 |
| WO | 00/63441 A2 | 10/2000 |
| WO | 03/046225 A1 | 6/2003 |

OTHER PUBLICATIONS

Bellizzi (DNA Research 20 pp. 537-547 Pub Jun. 26, 2013).*
Iacobazzi (Molecular Genetics and Metabolism 110 (Jul. 19, 2013) 25-34).*
Martorana (CNS Neuroscience and Therapeutics 16 (2010) pp. 235-245).*
Tost (Nature Protocols vol. 2 No. 9 2007 pp. 2265-2275).*
Autere, J., et al., "Mitochondrial DNA polymorphisms as risk factors for Parkinson's disease and Parkinson's disease dementia," Human Genetics, vol. 115, 2004, pp. 29-35.
Bellizzi et al., "The Control Region of Mitochondrial DNA Shows an Unusual CpG and Non-CpG Methylation Pattern," DNA Research 20:537-547, 2013.
Blanch, M., et al., Altered Mitochondrial DNA Methylation Pattern in Alzheimer Disease-Related Pathology and in Parkinson Disease 186(2):385-397, Feb. 1, 2016.
Byun, H.-M., et al., Effects of Airborne Pollutants on Mitochondrial DNA Methylation, Particle and Fibre Toxicology, 10:18, May 8, 2013, 8 pages.
Coppieters, N., et al., "Global changes in DNA methylation and hydroxymethylation in Alzheimer's disease human brain," Neurobiology of Aging, vol. 35, 2014, pp. 1334-1344.
Devall et al., "The mitochondrial epigenome: a role in Alzheimer's disease?" Epigenomics 6(6):665-675, 2014.
Extended European Search Report issued in connection with European Patent Application No. 15770042.8 dated Jan. 15, 2018.
Hong et al., "Regionally Specific and Genome-Wide Analyses Conclusively Demonstrate the Absence of CpG Methylation in Human Mitochondrial DNA," Mol. Cell Biol. 33(14):2683-2690, Jul. 2013.
Iacobazzi, V., et al., "Mitochondrial DNA methylation as a next-generation biomarker and diagnostic tool," Molecular Genetics and Metabolism, vol. 110, 2013, pp. 25-34.
Lakatos, A., et al., "Association between mitochondrial DNA variations and Alzheimer's Disease in the ADNI cohort," Neurobiology of Aging, vol. 31, No. 8, 2010, pp. 1355-1363.
Maekawa, M., Methylation of Mitochondrial DNA is Not a Useful Marker for Cancer Detection, Clinical Chemistry 50(8):1480-1481, Jun. 10, 2004.
Mancuso, M., et al., "Mitochondrial DNA sequence variation and neurodegeneration," Human Genomics, vol. 3, No. 1, 2008, pp. 71-78.
Martorana et al., "Beyond the Cholinergic Hypothesis: Do Current Drugs Work in Alzheimer's Disease?" CNS Neuroscience & Therapeutics 16:235-245, 2010.

(Continued)

*Primary Examiner* — Amanda Haney
(74) *Attorney, Agent, or Firm* — SEED INTELLECTUAL PROPERTY LAW GROUP LLP

(57) ABSTRACT

The present invention relates to an in vitro method to diagnose or determine the risk of developing a neurodegenerative disease in a subject based on the determination of the methylation pattern in certain regions of mitochondrial DNA from the subject. Finally, the present invention relates to nucleic acids suitable for application of the invention.

12 Claims, 11 Drawing Sheets

Specification includes a Sequence Listing.

(56) References Cited

OTHER PUBLICATIONS

Masliah, E., et al., "Distinctive patterns of DNA methylation associated with Parkinson disease: Identification of concordant epigenetic changes in brain and peripheral blood leukocytes," Epigenetics vol. 8, No. 10, Oct. 2013, pp. 1030-1038.

Matsuda et al., "Accurate Estimation of 5-Methylcytosine in Mammalian Mitochondrial DNA," Scientific Reports 8:5801, 2018., pp. 1-13.

Mawlood, "Quantification of Global Mitochondrial DNA Methylation Levels and Inverse Correlation With Age at Two CpG Sites," Aging 8(4):636-641, 2016.

Mechta et al., "Evidence Suggesting Absence of Mitochondrial DNA Methylation," Frontiers in Genetics 8, 1-9, 2017.

Park, C. B., et al., "Mitochondrial DNA mutations in disease and aging," Journal of Cell Biology, vol. 103, No. 5, 2011, pp. 809-818.

Rezak, "Current Pharmacotherapeutic Treatment Options in Parkinson's Disease," Dis Mon 53:214-222, 2007.

Sharma, S., et al., "Biomarkers in Parkinson's disease (recent update)," Neurochemistry International, 2013, vol. 63, No. 3, pp. 201-229.

Sims et al., "Sequencing depth and coverage: key considerations in genomic analyses," Nature Reviews 15:121-132, 2014.

Takasaki, S., "Japanese Alzheimer's Disease and Other Complex Disorders Diagnosis Based on Mitochondrial SNP-Haplogroups," International Journal of Alzheimer's Disease, vol. 2012, Article ID 245038, pp. 1-19.

Takasaki, S., "Mitochondrial haplogroups associated with Japanese centenarians, Alzheimer's patients, Parkinson's patients, type 2 diabetic patients and healthy non-obese young males," Journal of Genetics Genomics, vol. 36, No. 7, 2009, pp. 425-434.

Takasaki, S., "Mitochondrial SNPs associated with Japanese centenarians, Alzheimer's patients, and Parkinson's patients," Computational Biology and Chemistry, vol. 32, No. 5, 2008, pp. 332-337.

Tost et al., "DNA methylation analysis by pyrosequencing," Nature Protocols 2(9):2265-2275, 2007.

Wang, S.-C., et al., Age Specific Epigenic Drift in Late-Onset Alzheimer's Disease, PLOS One 3(7):e2698, Jul. 16, 2008, 11 pages.

Wong, M., et al., "Mitochondrial DNMT3A and DNA methylation in skeletal muscle and CNS of transgenic mouse models of ALS," Frontiers in Cellular Neuroscience, vol. 7, 2013, Article 279, pp. 1-16.

Yang, H., Correlation Between Increased ND2 Expression and Demethylated Displacement Loop of mtDNA in Colorectal Cancer, Molecular Medicine Reports 6: Apr. 12, 2012, p. 125-130.

International Search Report mailed by Oficina Española de Patentes y Marcas on Nov. 3, 2015 in the corresponding PCT App. No. PCT/ES2015/070230, 11 pages.

\* cited by examiner

MITOCHONDRIAL MARKERS OF NEURODEGENERATIVE DISEASES

STATEMENT REGARDING THE SEQUENCE LISTING

The Sequence Listing associated with this application is provided in text format in lieu of a paper copy, and is hereby incorporated by reference into the specification. The name of the text file containing the Sequence Listing is 370092_401C1_SEQUENCE_LISTING.txt. The text file is 28.4 KB, was created on Oct. 6, 2021, and is being submitted electronically via EFS-Web.

FIELD OF THE INVENTION

The present invention is classified as part of the diagnosis methods of neurological diseases.

BACKGROUND OF THE INVENTION

A considerable amount of neurodegenerative diseases are caused by or associated with altered mitochondrial function.

Alzheimer's disease (AD) and Parkinson's disease (PD) are within this group. The pathophysiological characteristics of AD and PD are related to deposits of aggregated protein. Specifically, AD is associated with the formation of intracellular phosphorylated tau aggregates in neurofibrillary tangles and extracellular aggregates of β-amyloid peptide in the senile plaques and PD is associated with the formation of abnormal α-synuclein aggregates that constitute the main component of the so called Lewy bodies and Lewy neurites.

It is accepted that Alzheimer's patients show decreased levels of the subunit ND4 in their brain tissue and that Parkinson's patients show reduced levels of ND6 in the substantia nigra. Furthermore, genetic studies have identified mutations in several COX genes and in the D-loop region as well as deletions of mtDNA in the brains of subjects with AD and in the substantial nigra of subjects with PD.

Different methods and strategies have been developed in the technology for diagnosis, prediction of onset and the development of neurodegenerative diseases, and specifically of AD and PD. In that way, diagnosis methods have been described for neurodegenerative diseases based on the identification of mutations in mitochondrial DNA through the employment of the RFLP (restriction fragment length polymorphism) technique or of other related techniques. The WO98038334 document describes a method of AD diagnosis based on the identification of mutations in COX genes. It has also proposed a method of PD diagnosis in a subject through the identification of single nucleotide polymorphisms in mitochondrial DNA samples of a subject (WO 2000063441). Other documents of the prior art describe diagnosis methods of Alzheimer's or Parkinson's disease based on the identification of polymorphisms in nuclear protein encoding genes that control the process of mitochondrial transcription. Despite the efforts that have been made to date, there remains a need for reliable methods of diagnosis for neurodegenerative diseases such as AD and PD, as well for the diagnosis of the stage of such diseases and to prognosticate the evolution of the same.

SUMMARY OF THE INVENTION

The first feature of the invention relates to an in vitro method to diagnose or to determine the risk of development of a neurodegenerative disease selected from Alzheimer's disease and Parkinson's disease in a subject that contains, in a sample from said subject containing mitochondrial DNA, the methylation pattern in the D-loop region and/or in the ND1 gene, wherein the methylation pattern is determined in at least one site selected from the group formed by:

i. the CpG sites in the D-loop region shown in Table 1
ii. the CpG sites in the ND1 gene shown in Table 2,
iii. the CHG sites in the D-loop region shown in Table 3,
iv. the CHG sites in the ND1 gene shown in Table 4, and/or
v. the CHH sites in the D-loop region shown in Table 5, where there is hypermethylation in at least one of said CpG sites in the D-loop region, hypermethylation in at least one of said CHG sites in the D-loop region, hypermethylation in at least one of said CHH sites in the D-loop region, hypomethylation in at least one of said CpG sites in the ND1 gene and/or hypomethylation in at least one of said CHG sites in the ND1 gene it is indicative that the subject suffers from Alzheimer's disease or that the subject has an elevated risk of developing Alzheimer's disease or in the case of hypomethylation in at least one of said CpG sites in the D-loop region, hypomethylation in at least one of said CHG sites in the D-loop region and/or hypomethylation in at least one of said CHH sites in the D-loop region it is indicative that the subject suffers from Parkinson's disease or that the subject has an elevated risk of developing Parkinson's disease.

The second feature of the invention relates to an in vitro method to select a subject for submission to preventive treatment of a neurodegenerative disease selected from Alzheimer's disease and Parkinson's disease in a subject that contains, in a sample from said subject containing mitochondrial DNA, the methylation pattern in the D-loop region and/or in the ND1 gene, where the methylation pattern is determined in at least one site selected from the group formed by:

i. the CpG sites in the D-loop region shown in Table 1,
ii. the CpG sites in the ND1 gene shown in Table 2;
iii. the CHG sites in the D-loop region shown in Table 3,
iv. the CHG sites in the ND1 gene shown in Table 4, and/or
v. the CHH sites in the D-loop region shown in Table 5 where there is hypermethylation in at least one of said CpG sites in the D-loop region, hypermethylation in at least one of said CHG sites in the D-loop region, hypermethylation in at least one of said CHH sites in the D-loop region, hypomethylation in at least one of said CpG sites in the ND1 gene and/or hypomethylation in at least one of said CHG sites in the ND1 gene, it is indicative that the subject is eligible to receive treatment aimed at preventing Alzheimer's disease or where there is hypomethylation in at least one of said CpG sites in the D-loop region, hypomethylation in at least one of said CHG sites of the D-loop region and/or hypomethylation in at least one of said CHH sites in the D-loop region, it is indicative that the subject is eligible to receive treatment aimed at preventing Parkinson's disease.

The third feature of the invention relates to an in vitro method to monitor the progression of a neurodegenerative disease selected from Alzheimer's disease or Parkinson's disease in a subject that contains in a sample from said subject containing mitochondrial DNA:

a) the methylation pattern in the D-loop region, and/or in the ND1 gene, where the methylation pattern is determined in at least one site selected from the group formed by:
i. the CpG sites in the D-loop region shown in Table 1,
ii. the CpG sites in the ND1 gene shown in Table 2;

iii. the CHG sites in the D-loop region shown in Table 3,
iv. the CHG sites in the ND1 gene shown in Table 4, and/or
v. the CHH sites in the D-loop region shown in Table 5 b) comparing the methylation pattern determined in step a) with said methylation pattern obtained in an earlier stage of the disease, where there is hypomethylation in at least one of said CpG sites in the D-loop region, hypomethylation in at least one of the said CHG sites in the D-loop region, hypomethylation in at least one of said CHH sites in the D-loop region, hypomethylation in at least one of said CpG sites in the ND1 gene and/or hypomethylation in at least one of said CHG sites in the ND1 gene with respect to said methylation pattern determined in an earlier stage of disease, it is indicative of the advance of Alzheimer's disease; and where there is hypomethylation in at least one of said CpG sites in the D-loop region, hypomethylation in at least one of said CHG sites in the D-loop region and/or hypomethylation in at least one of the said CHH sites in the D-loop region with respect to said determined methylation pattern at an earlier stage of the disease, is indicative of the advance of Parkinson's disease.

The fourth feature of the invention relates to an in vitro method to diagnose or determine the risk of development of Alzheimer's disease in a subject that contains in a sample comprising mitochondrial DNA from said subject, the nucleotide at the polymorphic position 16519 according to the sequence defined under the accession number NC_012920 in the NCBI database, wherein the detection of nucleotide C at said polymorphic position or presence of the nucleotide C at said polymorphic position in at least 60% of the molecules of mitochondrial DNA of the subject is indicative that the subject suffers from said disease or that the subject has an elevated risk of developing the disease.

In the fifth feature the invention relates to an in vitro method to select a subject to be submitted to preventive treatment for Alzheimer's disease, that involves determining in a sample containing mitochondrial DNA from said subject, the nucleotide at the polymorphic position 16519 according to the sequence defined under accession number NC_012920 in the NCBI database, where the detection of nucleotide C at said polymorphic position or the presence of the nucleotide C at said polymorphic position in at least 60% of the mitochondrial DNA molecules from said subject is indicative that the subject is eligible to receive treatment aimed at preventing Alzheimer's disease.

In the sixth feature, the invention relates to a nucleic acid selected from the group formed by:
(i) a nucleic acid comprising at least 9 contiguous nucleotides in a region of Mitochondrial DNA where said region comprises at least one methylation site selected from the group formed by:
  a) the CpG sites in the D-loop region shown in Table 1,
  b) the CpG sites in the ND1 gene shown in Table 2;
  c) the CHG sites in the D-loop region shown in Table 3,
  d) the CHG sites in the ND1 gene shown in Table 4, and
  e) the CHH sites in the D-loop region shown in table 5,
(ii) a nucleic acid comprising at least 9 contiguous nucleotides in a region of mitochondrial DNA region where said region comprises at least one methylation site selected from the group formed by:
  a) the CpG sites in the D-loop region shown in Table 1,
  b) the CpG sites in the ND1 gene shown in Table 2;
  c) the CHG sites in the D-loop region shown in Table 3,
  d) the CHG sites in the ND1 gene shown in Table 4, and
  e) the CHH sites in the D-loop region shown in Table 5.
where the position corresponding to the cytosine in the CpG, CHG or CHH site is uracil; and
(iii) a polynucleotide that hybridizes specifically with the nucleic acids of (i) or (ii)

The seventh aspect of the invention relates to a kit comprising at least one oligonucleotide capable of specifically hybridizing and in a methylation-dependent manner with a mitochondrial DNA sequence comprising a methylation site selected from the group formed by:
  i. the CpG sites in the D-loop region shown in Table 1,
  ii. the CpG sites in the ND1 gene shown in Table 2;
  iii. the CHG sites in the D-loop region shown in Table 3,
  iv. the CHG sites in the ND1 gene shown in Table 4, and/or
  v. the CHH sites in the D-loop region shown in Table 5

The eighth aspect the invention relates to a kit comprising at least one oligonucleotide capable of specifically hybridizing at position 5' or at position 3' with respect to a methylation site in the selected mitochondrial DNA from the group formed by:
  (i) the CpG sites in the D-loop region shown in Table 1,
  (ii) the CpG sites in the ND1 gene shown in Table 2;
  (iii) the CHG sites in the D-loop region shown in Table 3,
  (iv) the CHG sites in the ND1 gene shown in Table 4, and/or
  (v) the CHH sites in the D-loop region shown in Table 5
where the methylated cytosine in said position has converted to uracil or to another base that is distinguishable from cytosine in its hybridization properties.

Finally, the ninth feature of the invention corresponds to the use of the kits defined in the seventh and eight inventive aspects to determine the methylation pattern of mitochondrial DNA and to determine the diagnosis neurodegenerative disease in a subject selected from Alzheimer's disease and Parkinson's disease.

BRIEF DESCRIPTION OF THE DRAWINGS

FIGS. 4A-48: Graphics log 2 (OR) for CpG (A) and CHG (B) sites in the amplicon D-Loop in the frontal cortex of APP/PS1 mice and wild mice (WT) of three, six and twelve months. methylation sites sorted by 5' to 3' are represented in the x-axis The sites marked with a diamond are differentially methylated sites (FDR<0.05). Dots are estimated OR values, one for each site, and the band is the band of union of all the confidence intervals of 95%. C: control samples, WT: wild, TG: Transgenic.

DETAILED DESCRIPTION OF THE INVENTION

Figure 1A:
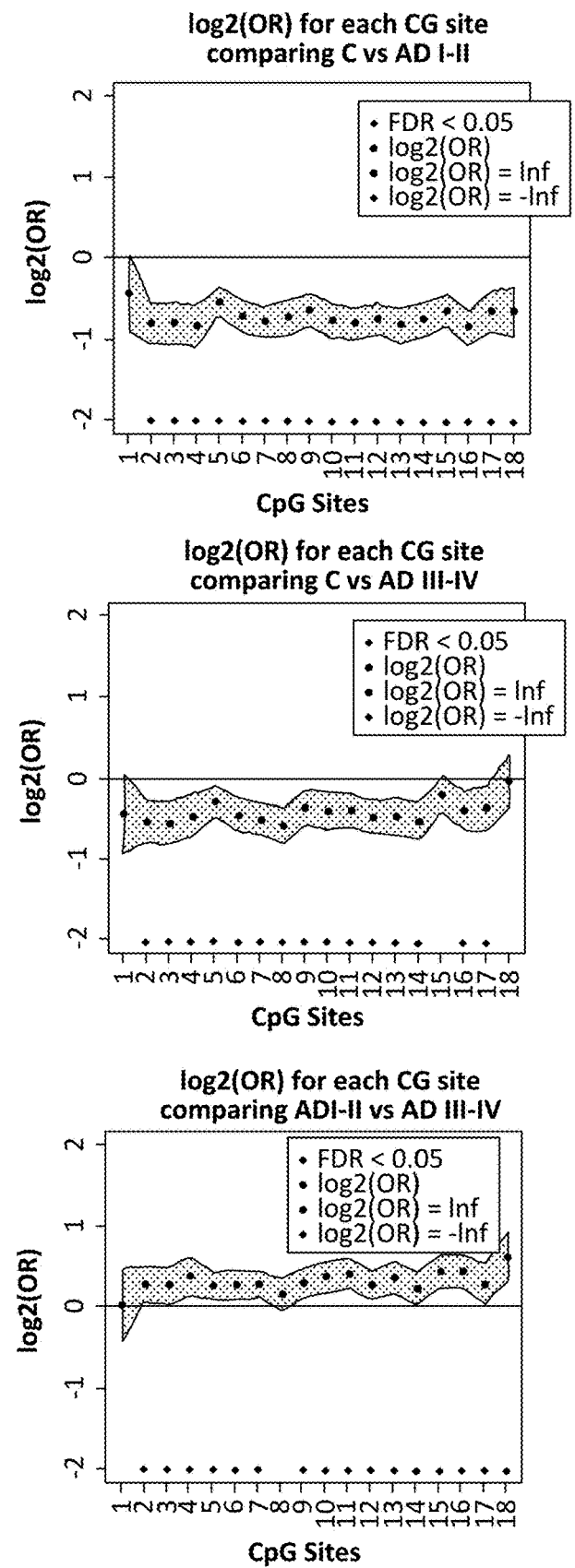
FIGS. 1A-1C: Graphics Log 2 (OR) for CpG (A) CHG (B) and CHH (C) sites in the amplicon D-Loop in the entorhinal cortex in AD pathology related cases. Methylation sites of 5' to 3' are represented in the x-axis. The sites marked with a diamond are differentially methylated sites (FDR<0.05). Dots are OR estimate values, one for each site, and the band is the band of union of all the confidence intervals of 95%. C: samples control, AD: Alzheimer's Disease.

The authors of the present invention have developed a method for diagnosing neurodegenerative diseases based on the determination of the methylation pattern in a sample of mitochondrial DNA from a subject. The inventors have found that, surprisingly, there are variations in the methylation pattern in the D-loop region and the ND1 gene in subjects suffering from AD or PD when compared with healthy subjects such as demonstrated in the examples. Furthermore, the inventors have discovered differential methylation patterns associated with the development of these diseases.

First Method of the Invention

The first feature of the invention relates to an in vitro method to diagnose or determine the risk of developing a neurodegenerative disease selected from Alzheimer's disease and Parkinson's disease in a subject (hereinafter, first method of the invention) that involves determining in a sample from said subject comprising mitochondrial DNA, the methylation pattern in the D-loop region and/or in the ND1 gene, where the methylation pattern is determined in at least one site selected from the group formed by:

(i) the CpG sites in the D-loop region shown in Table 1,
(ii) the CpG sites in the ND1 gene shown in Table 2;
(iii) the CHG sites in the D-loop region shown in Table 3,
(iv) the CHG sites in the ND1 gene shown in Table 4, and/or
(v) the CHH sites in the D-loop region shown in Table 5;
where there is hypomethylation in at least one of said CpG sites in the D-loop region, hypermethylation in at least one of said CHG sites in the D-loop region, hypermethylation in at least one of said CHH sites in the D-loop region, hypomethylation in at least one of said CpG sites in the ND1 gene and/or hypomethylation in at least one of said CHG sites in the ND1 gene, it is indicative that the subject suffers from Alzheimer's disease or that the subject is at an elevated risk of developing Alzheimer's disease or where there is hypomethylation in at least one of said CpG sites in the D-loop region, hypomethylation in at least one of said CHG sites in the D-loop region and/or hypomethylation in at least one of the said CHH sites in the D-loop region, it is indicative that the subject suffers from Parkinson's disease or that the subject is at an elevated risk of developing Parkinson's disease.

The term "diagnosis" as used in this document, refers to both the process of trying to determine and/or identify a possible disease in a subject, that is to say the diagnostic procedure, as well as the opinion reached through this process, that is to say, the diagnostic opinion. As such, it can also be seen as an attempt to classify the status of an individual in separate and distinct categories that allow medical decisions about treatment and prognosis to taken. As will be understood by the person skilled in the art, such diagnosis may not be correct for 100% of the subjects to be diagnosed with, although it is preferred that it is. However, the term requires that a statistically significant portion of subjects can be identified as suffering from a disease, in particular a neurodegenerative disease selected from Alzheimer's disease and Parkinson's disease in the context of the invention, or a predisposition thereto. The person skilled in the art may determine whether a part is statistically significant using different well known statistical evaluation tools, for example, by determining confidence intervals, determining the value of p, Student's t-test, the Mann-Whitney test, etc. (See Dowdy Wearden, 1983). Preferred confidence intervals are at least 50%, at least 60%, at least 70%, at least 80%, at least 90% or at least 95%. P values are preferably 0.05, 0.025, 0.001 or lower.

The expression "risk of developing a neurodegenerative disease" as used herein, refers to the predisposition, susceptibility or propensity of a subject to develop a neurodegenerative disease. The risk of developing a neurodegenerative disease generally implies that there is a high or low risk or higher or lower risk. Uke that, a subject has a high risk of developing a neurodegenerative disease, particularly Alzheimer's disease or Parkinson's disease, has a likelihood of developing this disease of at least 50%, or at least 60%, or at least 70%, or at least 80%, or at least 90, or at least 95%, or at least 97%, or at least 98%, or at least 99%, or at least 100%. Similarly, a subject at a low risk of developing a neurodegenerative disease, particularly Alzheimer's disease or Parkinson's disease, is a subject having at least one chance of developing the disease from at least 0%, or at least one 1%, or at least 2%, or at least 3%, or at least 5%, or at least 10%, or at least 20%, or at least 30%, or at least 40%, or at least 49%.

In general, the expression "predict risk" risk prediction", or similar, refers to the risk that a patient has of developing a neurodegenerative disease selected from Alzheimer's disease or Parkinson's disease, either high or low. As will be understood by the person skilled in the art, the prediction (or risk), albeit preferred, does not need to be correct for 100% of the subjects to be evaluated, but it is preferable that it is. The term, however, requires that a statistically significant portion of subjects can be identified with a higher probability to have a particular result. The person skilled in the art can determine without difficulty whether a part is statistically significant using several well-known statistical tools for assessment, for example, determination of confidence intervals, determination of p-value, cross-validation classification indices, etc. (more details in "Statistics for research" Dowdy and Wearden, John Wiley & Sons, New York, 1983). Preferred confidence intervals are at least 50%, at least 60%, at least 70%, at least 80%, at least 90% or at least 95%. P-values are, preferably, 0.1, 0.05, 0.02, 0.01 or lower The term "neurodegenerative disease" as used herein, includes chronic and progressive processes which are characterized by the selective and symmetric loss of neurons in motor, sensory and cognitive systems.

The term "Alzheimer's disease" or "senile dementia" or AD refers to a mental impairment associated with a specific degenerative brain disease characterized by the appearance of senile plaques, neuritic tangles and progressive neuronal loss that is clinically manifested in progressive deficiencies of memory, confusion, behavioral problems, inability to care for oneself, gradual physical deterioration and, ultimately, death. In preferred embodiments, the Alzheimer's disease at any stage according to Braak staging:

Stages I-II: the brain area affected by the presence of neurofibrillary tangles corresponding to the transentorhinal region of the brain Stages III-IV: the affected brain area also extends to areas of the limbic region such as the hippocampus Stages V-VI: the affected brain area also involves the neocortical region This classification by neuropathological stages correlates with the clinical evolution of the existing disease and there is a parallel between the decline in memory with the neurofibrillary changes and the formation of neuritic plaques in the entorhinal cortex and the hippocampus (stages I to IV). Also, the isocortical presence of these changes (stages V and VI) correlates with clinically severe alterations. The transentorhinal state (I-II) corresponds to clinically silent periods of disease. The limbic state (III-IV) corresponds to a clinically incipient AD. The neocortical state corresponds to a fully developed AD.

The term "Parkinson's disease" or "idiopathic parkinsonism" or "paralysis agitans" or PD as used herein, refers to a chronic, degenerative disease that involves problems of movement control, tremor, rigidity, bradykinesia in all kinds of movements such as walking, sitting, eating, talking, etc., and well as postural instability. Symptoms of the disease are clearly associated with the selective degeneration of dopaminergic neurons in the substantia nigra. The dopaminergic deficit induces a consequent loss of striatal neurons causing a variety of cytological changes including α-synuclein aggregation in so-called Lewy bodies. The "substantia nigra" is a nucleus of the basal ganglia located in the upper portions of the midbrain, under the thalamus and takes its color from the neuromelanin. In preferred embodiments, the PD is in any of the stages according to the Braak staging:

Stage I: the affected area is the dorsal motor nucleus and/or intermediate reticular zone.

Stage II: the affected area extends to coreuleus locus and to the nucleus raphes Stage III: the affected area extends to the midbrain, in particular the substantia nigra pars compacta.

Stage IV: The affected area extends to the transentorhinal region of the anteromedial temporal mesocortex and alocortex.

Stage V: The affected area extends to the insular cortex, the cingulate cortex and the temporal gyrus.

Stage VI: The affected area extends to frontal and parietal area of the cortex.

The term "subject" as used herein, refers to a person, such as a human being, non-human primate (e.g., chimpanzees and other apes and monkey species), farm animals, such as birds, fish, cattle, sheep, pigs, goats and horses, Pets such as dogs and cats; mammals, laboratory animals including rodents, such as mice, rats and guinea pigs. The term does not denote a particular age or sex. In a specific embodiment of the invention, the subject is a mammal. In a preferred embodiment of the invention, the subject is a human.

The expression "sample comprising mitochondrial DNA" as used herein refers to any sample that can be obtained from a subject in which there is genetic material from the mitochondria suitable for detecting the methylation pattern.

The term "mitochondrial DNA" or "mtDNA" as used herein, refers to the genetic material located in the mitochondria of living organisms. It is a closed, circular double-stranded molecule. In humans it consists of 16,569 base pairs, containing a small number of genes, distributed between the H chain and L chain. Mitochondrial DNA encodes 37 genes: two ribosomal RNA, 22 transfer RNA and 13 proteins that participate in oxidative phosphorylation.

In a specific embodiment of the invention, the sample comprising mitochondrial DNA is selected from a solid tissue biopsy or biofluid. The samples can be obtained by conventional methods known to the person skilled in the art.

In an even more specific embodiment, the biofluid is selected from peripheral blood or cerebrospinal fluid.

In an even more specific embodiment, said solid tissue is brain tissue.

In a preferred embodiment of the invention, if desired to diagnose a subject or if desired to determine the risk of developing PD, said sample is a brain tissue sample obtained from the substantia nigra.

If the material where it is desired to determine the methylation pattern according to the present method, that is to say the mtDNA, is in a solid tissue or biofluid preferably, it proceeds a prior nucleic acid extraction from the sample using any suitable technique for this. In a preferred embodiment of the invention, the DNA fraction suitable for the implementation of the invention is 35 total DNA. DNA extraction may be carried out using method known to the persons skilled in the art (Sambrook et al., 2001. "Molecular Cloning: A Laboratory Manual", 3rd ed, Cold Spring Harbor Laboratory Press, NY, Vol. 1-3) including, without limitation, density gradient centrifugation, extraction in two stages using aqueous phenol or chloroform with ethanol, column chromatography, methods based on the ability of DNA to bind itself on glass and/or silicates, such as diatomaceous earth as preparations or crystal beds, using commercial kits, for example, "Q-Biogene fast DNA® kits" or "QIAamp® (R) DNA Blood Mini Kit" (Qiagen, Hilden, Germany) the "G-Spin lip" (Intron Biotechnology, Korea) or the "Bio 101 Fast Prep System" (Qbiogene®, Madrid, Spain) or the methods described in U.S. Pat. Nos. 5,057,426, 4,923,978 and European Patent Application EP0512767A1.

If desired, the present method can be carried out in samples in which the mitochondrial fraction has previously been isolated and subsequently the DNA thereof has been isolated. The isolation of the mitochondrial fraction can be carried out using any known method of cell fractionation. Such methods comprise the previous cell disruption by techniques including physical disruption of the membranes, application of ultrasounds, pressure application or enzymatic techniques, followed by differential centrifugation by applying density gradients (such as those of Ficoll as or Percoll). They can also use commercial kits, for example, Qproteome "Mitochondrial isolation kit" (Qiagen, Hilden, Germany) or "Mitochondrial isolation kit for cultured cells" (Thermo Scientific, USA). These kits are based on the same basic principle, namely cell lysis and differential centrifugation to isolate or enrich the mitochondrial fraction.

The first method of the invention involves determining the methylation pattern in a sample from a subject comprising mitochondrial DNA. The term "DNA methylation" As used herein, refers to a biochemical process involving the addition of a methyl group ($-CH_3$) to DNA cytosine nucleotides (C) or adenine (A). DNA methylation at the 5 position of cytosine has the specific effect of gene repression and has been found in all of the vertebrates examined.

The term "methylation pattern" as used herein refers but is not limited to the presence or absence of methylation of one or more nucleotides. In this way, said one or more nucleotides are comprised in a single nucleic acid molecule.

Said one or more nucleotides are capable of being methylated or not. The term "methylation status" can also be used when only considered a single nucleotide. A methylation pattern can be quantified; in the case it is considered more than one nucleic acid molecule.

The term "D-loop" or "control region" as used herein, refers to a region of non-coding mtDNA containing approximately 1100 base pairs, visible under electron microscopy, which is generated during H chain replication for the synthesis of a short segment of the heavy strand, 7S DNA.

The term "ND1" or "NADH dehydrogenase 1" or "ND1mt", as used herein, refers to the gene localized in the mitochondrial genome that encodes the protein NADH dehydrogenase 1 or ND1. The human ND1 gene sequence is deposited in the GenBank database (version of Jan. 2, 2014) under the accession number NC_012920. SEQ ID NO 1. The ND1 protein is part of the enzyme complex called complex I which is active in the mitochondria and is involved in the process of oxidative phosphorylation.

The term "CpG site" as used herein, refers to DNA regions, particularly mitochondrial DNA regions, where a cytosine nucleotide is followed by a guanine nucleotide in linear sequence of bases along its length. "CpG" is an abbreviation for "C-phosphate-G", i.e., cytosine and guanine separated by only a phosphate; phosphate binds together any two nucleosides in the DNA. The term "CpG" is used to distinguish this linear sequence of CG bases pairing of guanine and cytosine. Cytosine in the CpG dinucleotides may be methylated to form 5-methylcytosine.

The term "CHG site" as used herein, refers to DNA regions, particularly mitochondrial DNA regions, where a cytosine nucleotide and a guanine nucleotide are separated by a variable nucleotide (H) which can be adenine, cytosine or thymine. The cytosine of the CHG site can be methylated to form 5-methylcytosine.

The term "CHH site" as used herein, refers to DNA regions, particularly regions of mitochondrial DNA, where a cytosine nucleotide is followed by a first and a second variable nucleotide (H) which can be adenine, cytosine or thymine. The cytosine of the CHG site can be methylated to form 5-methylcytosine.

In a specific embodiment, the first method of the invention comprises determining in a sample of a subject comprising mitochondrial DNA, the methylation pattern in at least one site selected from the CpG sites of the D-loop region, selected from the sites shown in Table 1.

TABLE 1

List of CpG positions 16386 and 256 in the D-loop region.

| CpG site | Position (bp) |
|---|---|
| CpG 2 | 16427 |
| CpG 3 | 16449 |
| CpG 4 | 16454 |
| CpG 5 | 16495 |
| CpG 6 | 16542 |
| CpG 7 | 16565 |
| CpG 8 | 33 |
| CpG 9 | 61 |
| CpG 10 | 78 |

TABLE 1-continued

List of CpG positions 16386 and 256 in the D-loop region.

| CpG site | Position (bp) |
|---|---|
| CpG 11 | 80 |
| CpG 12 | 91 |
| CpG 13 | 96 |
| CpG 14 | 105 |
| CpG 15 | 120 |
| CpG 16 | 162 |
| CpG 17 | 170 |
| CpG 18 | 186 |

The term "determination of the methylation pattern in a CG site" as used herein, refers to the determination of the methylation status of a particular CpG site. The determination of the methylation pattern of a CpG site can be performed by multiple processes known to the person skilled in the art.

In a specific embodiment, the first method of the invention involves determining the methylation pattern of at least one CpG site in the D-loop region selected from the sites shown in Table 1. In another specific embodiment, the first method of the invention involves determining the methylation pattern in at least 2, at least 3, at least 4, at least 5, at least 6, at least 7, at least 8, at least 9, at least 10, at least 11, at least 12, at least 13, at least 14, at least 15 or at least 16 CpG sites selected from Table 1.

In a still more specific and preferred embodiment of the invention, the first method of the invention comprises determining the methylation pattern of all of the CpG sites in the D-loop region shown in Table 1.

In another specific embodiment, the first method of the invention comprises determining in a sample of a subject containing mitochondrial DNA, the methylation pattern in at least one site selected from CpG sites of the ND1 gene shown in Table 2.

TABLE 2

List of CpG sites in the ND1 gene between the positions 3313 and 3686.

| CpG site | Position (bp) |
|---|---|
| CpG 1 | 3351 |
| CpG 2 | 3375 |
| CpG 3 | 3379 |
| CpG 4 | 3406 |
| CpG 7 | 3453 |
| CpG 12 | 3549 |
| CpG 13 | 3642 |

In another particular embodiment, the first method of the invention involves determining the methylation pattern in a CpG site selected from the ND1 gene shown in Table 2. In another specific embodiment, the first method of the invention involves determining the methylation pattern in at least 2, at least 3, at least 4, at least 5 or at least 6 CpG sites selected from Table 2.

In a still more particular and preferred embodiment of the invention, the first method of the invention involves determining the methylation pattern in all of the CpG sites of the ND1 gene shown in Table 2.

In another particular embodiment, the first method of the invention comprises determining in a sample of a subject comprising mitochondrial DNA, the methylation pattern in at least one site selected from the CHG sites in the D-loop region, shown in Table 3.

TABLE 3

List of the CHG sites between positions
16386 and 256 of the D-loop region

| CHG site | Position (bp) |
|---|---|
| CHG 2 | 16426 |
| CHG 3 | 16453 |
| CHG 4 | 16459 |
| CHG 5 | 16466 |
| CHG 6 | 16479 |
| CHG 7 | 16514 |
| CHG 8 | 6 |
| CHG 9 | 33 |
| CHG 10 | 64 |
| CHG 11 | 104 |
| CHG 12 | 122 |
| CHG 13 | 128 |
| CHG 14 | 141 |
| CHG 16 | 253 |

The term "determination of the methylation pattern in a CHG site" as used herein, refers to the determination of the methylation status of a particular CHG site.

The determination of the methylation pattern of a CHG site can be performed by multiple processes known to the person skilled in the art.

In a specific embodiment, the first method of the invention involves determining the methylation pattern of at least one CHG site of the D-loop region selected from the sites shown in Table 3. In another specific embodiment, the first method of the invention involves determining the methylation pattern in at least 2, at least 3, at least 4, at least 5, at least 6, at least 7, at least 8, at least 9, at least 10, at least 11, at least 12, at least 13 or at least 14 or at least 15 CHG sites selected from Table 3.

In a still more specific and preferred embodiment of the invention, the first method of the invention involves determining the methylation pattern in all of the CHG sites of the D-loop region shown in Table 3.

In another specific embodiment, the first method of the invention comprises determining in a sample of a subject comprising mitochondrial DNA, the methylation pattern in at least one site selected from CHG sites of the ND1 gene shown in Table 4.

TABLE 4

List of CHG sites in the ND1 gene between the
positions 3313 and 3686.

| CHG site | Position (bp) |
|---|---|
| CHG 1 | 3374 |
| CHG 2 | 3435 |
| CHG 4 | 3524 |
| CHG 5 | 3529 |
| CHG 6 | 3589 |
| CHG 7 | 3641 |
| CHG 8 | 3657 |

In another specific embodiment, the first method of the invention involves determining the methylation pattern in at least one CHG site in the ND1 gene selected from the sites shown in Table 4. In another specific embodiment, the first method of the invention comprises determining the methylation pattern in at least 2, at least 3, at least 4, at least 5 or at least 6 CHG sites selected from Table 4.

In a still more specific and preferred embodiment of the invention, the first method of the invention involves determining the methylation pattern in all of the CHG sites of the ND1 gene shown in Table 4.

In another specific embodiment, the first method of the invention comprises determining in a sample of a subject comprising mitochondrial DNA, the methylation pattern in at least one site selected from the CHH sites of the D-loop region, selected from the CHH sites shown in table 5.

TABLE 5

List of CHH sites between positions 16386 and
256 positions of the D-loop region.

| CHH site | Position (bp) |
|---|---|
| CHH 5 | 16419 |
| CHH 6 | 16425 |
| CHH 7 | 16429 |
| CHH 8 | 16439 |
| CHH 9 | 16442 |
| CHH 10 | 16446 |
| CHH 11 | 16451 |
| CHH 12 | 16458 |
| CHH 13 | 16465 |
| CHH 14 | 16478 |
| CHH 15 | 16498 |
| CHH 16 | 16507 |
| CHH 17 | 16511 |
| CHH 18 | 16520 |
| CHH 19 | 16527 |
| CHH 20 | 16536 |
| CHH 21 | 16540 |
| CHH 22 | 16546 |
| CHH 23 | 16549 |
| CHH 24 | 16560 |
| CHH 25 | 16563 |
| CHH 26 | 4 |
| CHH 27 | 11 |
| CHH 28 | 15 |
| CHH 29 | 18 |
| CHH 30 | 26 |
| CHH 31 | 29 |
| CHH 32 | 39 |
| CHH 33 | 43 |
| CHH 34 | 48 |
| CHH 35 | 76 |
| CHH 36 | 86 |
| CHH 37 | 110 |
| CHH 38 | 113 |
| CHH 39 | 132 |
| CHH 40 | 140 |
| CHH 41 | 144 |
| CHH 42 | 147 |
| CHH 43 | 150 |
| CHH 44 | 164 |
| CHH 45 | 167 |
| CHH 46 | 190 |
| CHH 47 | 194 |
| CHH 49 | 198 |

The term "determination of a methylation pattern in a CHH site", as used herein, refers to determining the methylation status of a particular CHH site. The determination of the methylation pattern of a CGH site you can be performed by multiple processes known to the person skilled in the art.

In another specific embodiment, the first method of the invention comprises determining the methylation pattern in at least one CHH site of the D-loop region selected from those shown in Table 5. In another specific embodiment, the first method of the invention involves determining the methylation pattern in at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least at least 22, at least 23, at least 24, at least 25, at least 26, at least 27, at least 28 at least 29, at least 30, at least 31, at least 32, at least 33, at least 34, at least 35, at least 36, at least 37, at least 38, at least 39, at least 40, at least 41, at least 42, or at least 43 CHH sites selected from Table 5.

In a still more specific and preferred embodiment of the invention, the first method of the invention involves determining the methylation pattern in all of the CHH sites in the D-loop region shown on table 5.

In preferred methods of embodiment, the first method of the invention includes:
  (i) determination of the pattern of methylation in all of the CpG sites of the D-loop region shown in Table 1 and all CpG sites of the ND1 gene shown in Table 2
  (ii) determination of the methylation pattern in all of the CpG sites in the D-loop region shown in Table 1 and in all of the CHG sites of the D-loop region shown in Table 3
  (iii) determination of the methylation pattern in all of the CpG sites of the D-loop region shown in Table 1 and all CHG sites of the ND1 gene shown in Table 4
  (iv) determination of the methylation pattern in all CpG sites in the D-loop region shown in Table 1 and in all CHH sites in the D-loop region shown in Table 5
  (v) determination of the methylation pattern in all of the CpG sites in the ND1 gene shown in Table 2 1 and in all of the CHG sites in the D-loop region shown on Table 3
  (vi) determination of the methylation pattern in all of the CpG sites in the NDI gene shown in Table 2 and in all of the CHG sites in the NDI gene shown in Table 4,
  (vii) determination of the methylation pattern in all of the CpG sites in the ND1 gene shown in Table 2 and in all of the CHH sites of the D-loop region shown in Table 5
  (viii) determination of the methylation pattern in all of the CHG sites in the D-loop region shown in Table 3 and all CHG sites of the ND1 gene shown in Table 4
  (ix) determination of the methylation pattern in all CHG sites in the D-loop region shown in Table 3 and/or
  (x) determination of the methylation pattern in all of the CHG sites in the ND1 gene shown in Table 4 and in all of the CHH sites in the D-loop region in Table 5

In some embodiments, the determination of the methylation pattern in at least one CpG site, at least one CHG site and/or at least one CHH site according to the first method of the invention is carried out in a whole blood sample, in which case the determination can be made directly. In other embodiments, the sample that contains mitochondrial DNA, preferably a sample of total DNA, is extracted from cells present in a biological fluid (e.g., whole blood, cerebrospinal fluid) as an initial stage and in such cases, the total nucleic acid extracted from these samples represent the suitable work material for the later analysis. The Isolation of total DNA or mitochondrial DNA can be performed by conventional methods known to the person skilled in the art (cited supra). After isolating and amplifying (if necessary) the nucleic acid that contains mitochondrial DNA, the methylation pattern of one or more CpG sites, one or more CHG sites and/or one or more CHH sites is determined. The person skilled in the art will easily recognize that the analysis of the methylation pattern present in one or several of the CpG, CHG and/or CHH sites described herein in the mitochondrial DNA of a subject, can be carried out by any method or technique capable of measuring the methylation pattern present in such sites.

In another specific embodiment, the first method of the invention involves determining the methylation pattern in said CpG, CHG and/or CHH sites through a technique selected from the group consisting of Methylation Specific PCR (MSP), a method based on enrichment. (e.g. MeDIP, MBD-seq and MethylCap), bisulfite sequencing and through a bisulphite based method (eg. RRBs, Infinium, Golden-Gate, Cobra, MSP, MethyUght) and a method by restriction of digestion (e.g., MRE-seq, or HELP trial), pyrosequencing, or differential conversion, differential restriction, differential weight of the methylated DNA CpG, CHG and/or CHH sites.

In a specific and preferred embodiment of the invention the methylation pattern of one or more CpG, CHG and/or CHH sites in the D-loop region and/or one or more CpG and/or CHG sites in the ND1 gene is determined through pyrosequencing. Briefly, this technique is based on the principle of sequencing by synthesis and detection of released pyrophosphate (PPi) during DNA synthesis. This technique employs a series of four enzymes to detect nucleic acid sequences during the synthesis process; DNA polymerase, ATP sulfurylase, luciferase, apyrase and adenosine 5' fosofosulphate (APS) and luciferin used as substrates.

To determine the methylation pattern in mitochondrial DNA, it is necessary to chemically treat said sample so that all cytosine unmethylated bases are modified at uracil bases, or so another base which differs from cytosine in terms of base pairing behavior, while the bases of 5 methylcytosine remain unchanged. The term "modify" as used herein means the conversion of an unmethylated cytosine to another nucleotide that will distinguish the unmethylated cytosine from the methylated cytosine. The conversion of unmethylated cytosine bases, but not methylated, in the sample containing mitochondrial DNA is carried out with a conversion agent. The term "conversion agent" or "conversion reagent" as used herein, refers to a reagent capable of converting an unmethylated cytosine to uracil or another base that is differentially detectable to cytosine in terms of hybridization properties. The conversion agent is preferably a bisulfate such as bisulfites or hydrogen sulfite. However, other agents that similarly modify unmethylated cytosine, but not methylated cytosine can also be used in this method of the invention, such as hydrogen sulfite. The reaction is performed according to standard procedures (Frommer et al., 1992, Proc. Natl. Acad. Sci. USA 89: 1827-1831; Olek, 1996, Nucleic Acids Res. 24: 5064-6; EP 1394172). It is also possible to carry out the conversion enzymatically, eg. using cytidine deaminases specific methylation.

In a preferred embodiment of the first method of the invention, the sample containing mitochondrial DNA has been treated with a reagent capable of converting an unmethylated cytosine to uracil or another base that is detectably different from cytosine in terms of hybridization properties. In a more preferable embodiment, the sample comprising mitochondrial DNA is treated with bisulfite using an appropriate commercial kit, for example "EZ Methylation Kit" (Zymo Research, Ecogen; Barcelona, Spain).

Once the sample containing mitochondrial DNA has been treated with a bisulfite, the D-loop region and/or the ND1 gene containing one or more CpG, CHG and/or CHH sites shown in Tables 1 to 5 can be amplified using primers that distinguish unmethylated sequence (in which the cytosine of the CpG site is converted into uracil) from the methylated sequence (in which the cytosine in the CpG site remains as cytosine). Many amplification methods rely on an enzymatic chain reaction such as, for example, a polymerase chain reaction (PCR), ligase chain reaction (LCR), ligase chain reaction Polymerase 35, Gap-LCR, repair chain reaction, 3SR and NASBA. Furthermore, there is strand displacement amplification (SDA), transcription mediated amplification (TMA), and Qs-amplification, etc, this being merely an illustrative list. Methods of nucleic acid amplification are described in Sambrook et al., 2001 (cited supra). Other amplification methods include PCR method specific methylation (MSP) described in document U.S. Pat. No. 5,786,146 which combines bisulfite treatment and allele-specific PCR (see. eg., U.S. Pat. Nos. 5,137,806, 5,595,890, 5,639,611). Uracil is recognized as a thymine by Taq polymerase and therefore, according to PCR, the resultant product contains cytosine only at the position where 5-methylcytosine DNA exist in the starting template.

In a preferred embodiment of the invention, once the sample comprising mitochondrial DNA, preferably a sample of total DNA, has been treated with bisulfite, the region containing one or more CpG, CHG and/or CHH site(s) can be amplified using primers that are not specific to the methylated sequence. For example, the preferred sequence of the primers not corresponding to a nucleotide sequence comprising a CpG dinucleotide.

Amplification products are detected according to standard procedures in prior art. The amplified nucleic acid can be determined through methods known to person skilled in the art and are described in. eg., Sambrook et al., 2001 (cited et supra). There may also be additional purification steps before the target nucleic acid is detected, for example a precipitation step. The detection methods may include but may not limited to binding or interleaving of specific dyes such as ethidium bromide which intercalate into double stranded DNA and changes its fluorescence thereafter. The purified nucleic acids may also be separated by electrophoretic methods optionally after a restriction of digestion and be displayed later. There are also probe-based assays which exploit the oligonucleotide hybridization to specific sequences and subsequent detection of the hybrid. It is also possible to sequence the target nucleic acid after further steps known to the person skilled in the art. Other methods use various nucleic acid sequences with a silicon chip to which specific probes are bound and produce a signal when a complementary sequence binds.

In a preferred embodiment of the invention, after amplification of the region of interest where it is desired to determine the methylation pattern (eg in the D-loop region or in the ND1 gene) pyrosequencing is used to determine in said sequence CpG, CHG and/or modified CHH sites after treatment with bisulphite The reason for cytosine/thymine in each of the sites can be quantitatively determined based on the amount of cytosine and thymine incorporated during the extension step of the sequence.

Alternatively, the methylation pattern of at least one CpG, CHG and/or CHH sites in the D-loop region or in at least one CpG and/or CHG site of the ND1 gene of the site can be confirmed by restriction enzyme digestion and Southern blot analysis. Examples of endonucleases methylation sensitive restriction that may be used include SmaI, SacII, EagI, MspI, HpaII, BstUI Y BssHII, for example.

The term "hypermethylation" as used herein, refers to an altered methylation pattern where one or more nucleotides, preferably cytosines from CpG, CHG and/or CHH sites are methylated compared to a reference sample. Said reference sample is preferably a sample that contains mitochondrial DNA obtained from a subject not suffering from a neurodegenerative disease selected from AD or PD. In particular, the term refers to a number larger than 5-methylcytosines in one or more CpG sites in the D-loop region shown in Table 1, in one or more CpG sites in the ND1 gene shown in Table 2, in one or more CHG sites in the D-loop region shown in Table 3, in one or more CHG sites in the ND1 gene shown in Table 4 and/or one or more CHH sites in the D-loop region shown in Table 5, in a sequence of mitochondrial DNA when compared with the relative amount of 5-methylcytosines present in said one or more sites in a reference sample.

The term "hypomethylation" as used herein, refers to an altered methylation pattern where one or more nucleotides, preferably cytosines in the CpG, CHG and/or CHH sites, are unmethylated compared to a reference sample. The term "reference sample" refers to a sample containing mitochondrial DNA obtained from a subject not suffering from a neurodegenerative disease selected from AD or PD. In particular, said term refers to a small number of 5-methylcytosines in one or more CpG sites in the D-loop region shown in Table 1, in one or more CpG sites of the ND1 gene shown in Table 2, in one or more sites CHG sites in the D-loop region shown in Table 3, in one or more CHG sites in the ND1 gene shown in Table 4 and/or one or more CHH sites in the D-loop region shown in Table 5 in a sequence of mitochondrial DNA as compared to the relative amount of 5-methylcytosines present in said one or more CpG sites, one or more CHG sites and/or one or more CHH sites in a reference sample.

In a preferred embodiment of the invention, said reference sample containing mitochondrial DNA is selected from tissue samples, or biofluids, preferably blood samples or cerebrospinal fluid of subjects. In a preferred embodiment, said reference sample is total DNA. Methods to obtain these samples as well as methods of isolating total DNA or mitochondrial DNA of a sample have been detailed above. In a still more preferred embodiment, the reference sample is a sample containing mitochondrial DNA from age-matched subjects.

In this first method, the invention provides some specific CpG, CHH and CHG sites that are related to the diagnosis or risk of developing a neurodegenerative disease selected from Alzheimer's disease and Parkinson's disease. Therefore:

hypermethylation in at least one of the CpG sites in the D-loop region shown in Table 1,
hypermethylation in at least one of the CHG sites in the D-loop region shown in Table 3,
hypermethylation in at least one of the CHH sites in the D-loop region shown in Table 5,
hypomethylation in at least one of the CpG sites in the ND1 gene shown in Table 2, and/or
hypomethylation in at least one of the CHG sites in the ND1 gene shown in Table 4, is indicative that the subject suffers from Alzheimer's disease or that the subject is at a high risk of developing Alzheimer's disease; or
hypomethylation in at least one of the CpG sites in the D-loop region shown in Table 1,
hypomethylation in at least one of the CHG sites in the D-loop region shown in Table 3, and/or
hypomethylation in at least one of the CHH sites in the D-loop region shown in Table 5 is indicative that the subject suffers from Parkinson's or that the subject is at a high risk of developing Parkinson's disease.

In a specific embodiment, the first method of the invention involves determining the methylation pattern of all the CpG sites, all CHG sites and all CHH sites in the D-loop region shown in Tables 1, 3 and 5, and the methylation pattern of all the CpG sites all of all CHG sites of the ND1 gene shown in Tables 2 and 4.

The authors of the present invention have found that the degree of methylation in the CpG, CHG and CHH sites in the D-loop region is greater in subjects suffering from Alzheimer's in stages I-II than in subjects suffering from the disease in stages III-IV.

In a specific embodiment, if the methylation pattern with respect to the reference pattern is observed in a sample containing mitochondrial DNA from a subject diagnosed with Alzheimer's disease stage I-II, then hypomethylation in at least one of the CpG sites in the D-loop region shown in Table 1 or hypomethylation in one of said CHG sites in the D-loop region shown in Table 3, indicates that the subject suffers from Alzheimer's disease stage III-IV.

Second Method of the Invention

In the second feature, the invention relates to an in vitro method to select a subject to be submitted to preventive treatment of a neurodegenerative disease selected from Alzheimer's disease and Parkinson's disease in a subject (hereinafter, second method of the invention) that involves determining in a sample of said subject containing mitochondrial DNA the methylation pattern in the D-loop region, and/or in the ND1 gene, where the methylation pattern is determined in at least one site selected from the group formed by:
  i. the CpG sites in the D-loop region shown in Table 1,
  ii. the CpG sites in the ND1 gene shown in Table 2;
  iii. the CHG sites in the D-loop region shown in Table 3,
  iv. the CHG sites in the ND1 gene shown in Table 4, and/or
  v. the CHH sites in the D-loop region shown in Table 5 where there is hypomethylation in at least one of said CpG sites in the D-loop region, hypermethylation in at least one of said CHG sites in the D-loop region, hypermethylation in at least one of said CHH sites in the D-loop region, hypomethylation in at least one of said CpG sites in the ND1 gene and/or hypomethylation in at least one of said CHG sites in the ND1 gene, it is indicative that the subject is a candidate to receive treatment aimed at preventing Alzheimer's disease or where there is hypomethylation in at least one of said CpG sites in the D-loop region, hypomethylation in at least one of said CHG sites in the D-loop region and/or hypomethylation in at least one of the said CHH sites in the D-loop region it is indicative that the subject is a candidate to receive treatment aimed at preventing Parkinson's disease.

The term "preventive treatment", as used herein, refers to the prevention or conjunction of prophylactic measures to prevent disease to prevent or delay the onset of symptoms thereof as well as reducing or alleviating clinical symptoms thereof. In particular, the term refers to the prevention or set of measures to prevent the occurrence, to delay or to relieve the clinical symptoms associated with a neurodegenerative disease selected from Alzheimer's and Parkinson's disease. Desired clinical outcomes associated with the administration of the treatment to a subject include but are not limited to, stabilization of the pathological stage of the disease, delay in the progression of the disease or improvement in the physiological state of the subject.

Suitable preventative treatments aimed at preventing or delaying the onset of the symptoms of Alzheimer's disease include but are not limited to, cholinesterase inhibitors such as donepezil hydrochloride (Arecept), rivastigmine (Exelon) and galantemina (Reminyl) or antagonists N-methyl-D-aspartate (NMDA). Treatments aimed at preventing or delaying the onset of the symptoms of Parkinson's disease include but are not limited to, L-dopa, inhibitors of catechol-o-methyl transferase (COMT) such as tolcapone (Tasmar) and entacapone (Comtan), monoamine oxidase B (MAOB) such as selegiline (Eldepryl) and rasagaline (Azilect) and dopamine agonists such as pramipexole, rotigotine and ropinirole.

The term "to select" as used herein, refers to the action of choosing a subject for submission to preventive treatment of a neurodegenerative disease selected from Alzheimer's disease and Parkinson's disease.

The terms "subject", "neurodegenerative disease", "Alzheimer's disease", "Parkinson's disease", "sample", "mitochondrial DNA", "D-loop region", "ND1 gene", "CpG site", "CHG site", CHH site", "methylation pattern", "hypermethylation" and "hypomethylation" have been described in detail in the context of the first method of the invention and used with the same meaning in the second method of the invention.

In a specific embodiment of the second method of the invention, the sample comprising mitochondrial DNA is selected from a biopsy of a solid tissue or biofluid. The samples can be obtained by conventional methods known to the person skilled in the art.

In an even more specific embodiment, the biofluid is selected from peripheral blood or cerebrospinal fluid.

In an even more specific embodiment, said solid tissue is brain tissue. In a preferred embodiment of the invention, if desired to select a subject to be submitted to preventive treatment of Parkinson's disease, said sample is a brain tissue sample obtained from the substantia nigra.

In a specific embodiment, the second method of the invention involves determining in a sample of a subject containing mitochondrial DNA, the methylation pattern in at least one site selected from CpG sites in the D-loop region, shown in Table 1.

In a specific embodiment, the second method of the invention involves the determination of the methylation pattern in at least one CpG site in the D-loop region selected from those shown in Table 1. In another specific embodiment, the first method of the invention involves determining the methylation pattern in at least 2, at least 3, at least 4, at least 5, at least 6, at least 7, at least 8, at least 9, at least 10, at least 11, at least 12, at least 13, at least 14, at least 15 or at least 16 CpG sites selected from Table 1.

In a still more specific and preferred embodiment of the invention, the second method of the invention involves determining the methylation pattern in all of the CpG sites in the D-loop region shown in Table 1.

In another specific embodiment, the second method of the invention involves determining in a sample of a subject comprising mitochondrial DNA, the methylation pattern in at least one site selected from the CpG sites in the ND1 gene, shown in Table 2.

In another specific embodiment, the second method of the invention involves determining the methylation pattern in a CpG site in the ND1 gene selected from the sites shown in Table 2. In another specific embodiment, the second method of the invention involves determining the methylation pattern in at least 2, at least 3, at least 4, at least 5 or at least 6 CpG sites selected from Table 2.

In a still more specific and preferred embodiment of the invention, the second method of the invention involves determining the methylation pattern of all of the CpG sites in the ND1 gene shown in Table 2.

In another particular embodiment, the second method of the invention involves determining in a sample of a subject containing mitochondrial DNA, the methylation pattern in at least one site selected from the CHG sites in the D-loop region, shown in Table 3.

In a particular embodiment, the second method of the invention involves determining the methylation pattern in at least one CHG site in the D-loop region selected from the sites shown in Table 3. In another specific embodiment, the second method of the invention involves determining the methylation pattern in at least 2, at least 3, at least 4, at least 5, at least 6, at least 7, at least 8, at least 9, at least 10, at least 11, at least 12, at least 13 or at least 14 or at least 15 CHG sites selected from Table 3.

In a still more specific and preferred embodiment of the invention, the second method of the invention involves determining the methylation pattern of all the CHG sites in the D-loop region shown in Table 3.

In another specific embodiment, the second method of the invention involves the determination in a sample of a subject that contains mitochondrial DNA, the methylation pattern in at least one site selected from the CHG sites in ND1 gene, shown in Table 4.

In another specific embodiment, the second method of the invention involves determining the methylation pattern in at least one CHG site in the ND1 gene selected from the sites shown in Table 4. In another specific embodiment, the second method of the invention involves determining the methylation pattern in at least 2, at least 3, at least 4, at least 5 or at least 6 CpG sites selected from Table 4.

In a still more particular and preferred embodiment of the invention, the second method of the invention involves determining the methylation pattern in all of the CHG sites of the ND1 gene shown in Table 4.

In another specific embodiment, the second method of the invention involves determining in a sample of a subject containing mitochondrial DNA, the methylation pattern in at least one site selected from the CHH sites in the D-loop region, shown in Table 5.

In another specific embodiment, the second method of the invention involves determining the methylation pattern in at least one CHH site in the D-loop region selected from those shown in Table 5. In another specific embodiment, the second method of the invention involves determining the methylation pattern in at least 2, at least 3, at least 4, at least 5, at least 6, at least 7, at least 8, at least 9, at least 10, at least 11, at least 12, at least 13, at least 14, at least 15, at least 16, at least at least 17, at least 18, at least 19, at least 20, at least 21, at least at least 22, at least 23, at least 24, at least 25, at least 26, at least 27, at least 28, at least 29, at least 30, at least 31, at least 32, at least 33, at least 34, at least 35, at least 36, at least 37, at least 38, at least 39 at least 40, at least 41, at least 42 or at least 43 CHH sites selected from Table 5.

In a still more specific and preferred embodiment of the invention, the second method of the invention involves determining the methylation pattern in all of the CHH sites in the D-loop region shown in Table 5.

In preferred methods of embodiment, the second method of the invention includes:
(i) determination of the methylation pattern in all of the CpG sites in the D-loop region shown in Table 1 and in all of the CpG sites in the ND1 gene shown in Table 2
(ii) determination of the methylation pattern in all of the CpG sites in the D-loop region shown in Table 1 and in all of the CHG sites in the D-loop region shown in Table 3
(iii) determination of the methylation pattern in all of the CpG sites in the D-loop region shown in Table 1 and in all of the CHG sites in the ND1 gene shown in Table 4
(iv) determination of the methylation pattern in all CpG sites in the D-loop region shown in Table 1 and in all CHH sites in the D-loop region shown in Table 5
(v) determination of the methylation pattern in all of the CpG sites in the ND1 gene shown in Table 2 1 and in all CHG sites in the D-loop region shown in Table 3
(vi) determination of the methylation pattern in all of the CpG sites in the NDI gene shown in Table 2 and in all of the CHG sites in the NDI gene shown in Table 4
(vii) determination of the methylation pattern in all CpG sites in the ND1 gene shown in Table 2 and in all the CHH sites in the D-loop region shown in Table 5
(viii) determination of the methylation pattern in all of the CHG sites in the D-loop region shown in Table 3 and in all of the CHG sites in the ND1 gene shown in Table 4
(ix) determination of the methylation pattern in all of the CHG sites in the D-loop region shown in Table 3 and/or
(x) determination of the methylation pattern in all of the CHG sites in the ND1 gene shown in Table 4 and in all of the CHH sites in the D-loop region shown in Table 5

Suitable methods for determining the methylation pattern in a sample of a subject containing mitochondrial DNA have been described in detail in the context of the first method of the invention.

In a specific embodiment, the second method of the invention involves determining the methylation pattern in said CpG, CHG and/or CHH sites through a technique selected from the group consisting of Methylation-Specific PCR-based enrichment method (e.g. MeDIP, MBD-seq and MethylCap), sequencing bisulfite and based on bisulfite method (e.g. RRBs, Infinium, GoldenGate, Cobra, MSP, MethyUght) and a method for restriction digestion (e.g., MRE-seq, or HELP trial), pyrosequencing, assay chIP-on-chip, or differential conversion, differential restriction, differential weight of the CpG, CHG and/or CHH sites methylated DNA.

In a specific and preferred embodiment of the invention the methylation pattern of one or more CpG, CHG and/or CHH sites in the D-loop region and/or one or more CpG or CHH sites in the ND1 gene, according to the second method of the invention is determined by pyrosequencing.

According to the second method of the invention:
hypermethylation in at least one of the CpG sites in the D-loop region shown in Table 1,
hypermethylation in at least one of CHG sites in the D-loop region shown in Table 3,
hypermethylation in at least one of the CHH sites in the D-loop region shown in Table 5
hypomethylation in at least one of the CpG sites in the ND1 gene shown in Table 2
and/or hypomethylation in at least one of the CHG sites in the ND1 gene shown in Table 4, is indicative that the subject is a candidate to receive treatment aimed at preventing Alzheimer's disease; or
hypomethylation in at least one of the CpG sites in the D-loop region shown in Table 1
hypomethylation in at least one of the CHG sites in the D-loop region shown in Table 3,
and/or hypomethylation in at least one of the CHH sites in the D-loop region shown in Table 5
is indicative that the subject is a candidate to receive treatment aimed at preventing Parkinson's disease.

In a specific embodiment, the second method of the invention involves determining the methylation pattern of all the CpG sites, all CHG sites and all of the CHH sites in the D-loop region shown in Tables 1, 3 and 5, and the methylation pattern of all the CpG sites and all of the CHG sites in the ND1 gene shown in Tables 2 and 4.

Third Method of the Invention

In the third feature, the invention relates to an in vitro method to monitor the progression of a neurodegenerative disease selected from Alzheimer's or Parkinson's disease in a subject (hereinafter, ti method of the invention) Involving:
(a) Determination in a sample from said subject containing mitochondrial DNA, the methylation pattern in the D-loop region, and/or in the ND1 gene, where the methylation pattern is determined at least one site selected from the group formed by:
  (i) the CpG sites in the D-loop region shown in Table 1,
  (ii) the CpG sites in the ND1 gene shown in Table 2;
  (iii) the CHG sites in the D-loop region shown in Table 3,
  (iv) the CHG sites in the ND1 gene shown in Table 4, and/or
  (v) the CHH sites in the D-loop region shown in Table 5 and
(b) comparing the methylation pattern determined in step a) with said methylation pattern obtained in an earlier stage of the disease, in the case of hypomethylation in at least one of said CpG sites in the D-loop region, hypomethylation in at least one of said CHG sites in the D-loop region, hypomethylation in at least one of the said CHH sites in the D-loop region, hypomethylation in at least one of said CpG sites in the ND1 gene and/or hypomethylation in at least one of said CHG sites in the ND1 gene relative to said methylation pattern determined at an earlier stage of disease, is indicative of the advance of Alzheimer's disease; and where there is hypomethylation in at least one of said CpG sites in the D-loop region, hypomethylation in at least one of said CHG sites in the D-loop region and/or hypomethylation in at least one of said CHH sites in the D-loop region with respect to said methylation pattern determined at an earlier stage of the disease is indicative of the advance of Parkinson's disease.

The term "monitor the progression" which is equivalent to "determine the prognosis" refers to determining the progression of a disease in a subject diagnosed with said disease. Particularly, the term refers to determining the progression of a neurodegenerative disease selected from Alzheimer's disease and Parkinson's disease in a subject diagnosed with said disease. As the person skilled in the art knows, there are several suitable parameters to determine the evolution of a disease in a subject, for example, the evolution of a neurodegenerative disease selected from AD and PD, can be determined by, determination of overall survival.

In a specific embodiment, the subject under study has been diagnosed with AD stage I-II.

In another specific embodiment, the subject under study has been diagnosed with PD in stages III-V.

The term "overall survival", as used herein, refers to the percentage of patients who survive from the time of diagnosis or treatment of a neurodegenerative disease selected from Alzheimer's and Parkinson's disease, after a defined period of time.

The terms "subject", "neurodegenerative disease", "Alzheimer's disease", "Parkinson's disease", "sample", "mitochondrial DNA", "D-loop region", "ND1 gene", "CpG site", "CHG site "CHH site", "methylation pattern", "hypermethylation" and "hypomethylation" have been described in detail in the context of the first method of the invention and are used with the same meaning in the third method of the invention.

According to the third method of the invention, the first step of determining the prognosis of a neurodegenerative disease selected from AD and PD involves determining in a sample containing mitochondrial DNA from a subject diagnosed with said neurodegenerative disease, the methylation pattern in the D-loop region and/or in the ND1 gene in at least one site selected from sites shown in Tables 1 to 5.

In a second step, the third method of the invention involves comparing the methylation pattern obtained in said first step with said methylation pattern obtained in an earlier stage of disease. Therefore, the third method of the invention involves determining the methylation pattern in a sample containing mitochondrial DNA (first sample) from a subject diagnosed with said neurodegenerative disease, the methylation pattern in the D-loop region and/or in the ND1 gene in at least one site selected from the CpG, CHG and/or CHH sites shown in Tables 1 to 5 and, after a suitable period of time, determining in a sample containing mitochondrial DNA (second sample) of said subject diagnosed with said neurodegenerative disease, the methylation pattern at these sites. Said second sample can be obtained a period of one month, two months, three months, four months, five months, six months, one year, two years, three years, four years, five years, ten years or more after obtaining the first sample.

In a particular embodiment, said first sample is obtained from a subject who is not receiving any proper treatment for said neurodegenerative disease selected from AD and PD and said second sample is obtained after a period of time where treatment of the disease is taking place. In another specific embodiment, said first sample is obtained at the beginning of appropriate treatment for said neurodegenerative disease and the second sample is obtained at one or more points during the course of the treatment.

According to the third method of the invention:
hypomethylation in at least one of the CpG sites in the D-loop region shown in Table 1,
hypomethylation in at least one of the CHG sites in the D-loop region shown in Table 3,
hypomethylation in at least one of the CHH sites in the D-loop region shown in Table 5,
hypomethylation in at least one of the CpG sites in the ND1 gene shown in Table 2,
and/or hypomethylation in at least one of the CHG sites in the ND1 gene shown in Table 4, with respect to said methylation pattern determined at an earlier stage of disease is indicative of the advance of Alzheimer's disease; or
hypomethylation in at least one of the CpG sites in the D-loop region shown in Table 1,
hypomethylation in at least, one of the CHG sites in the D-loop region shown in Table 3,
and/or hypomethylation in at least one of the CHH sites in the D-loop region shown in Table 5,
with respect to said methylation pattern determined at an earlier stage of disease is indicative of the advance of Parkinson's disease.

The expression "advance of Alzheimer's disease" as used herein, refers to the subject being at a more evolved stage of the disease with respect to the stage where the subject was diagnosed. That is, if the subject was classified as stage I-II of the AD (according to the brain impairment and/or symptoms or clinical manifestations of the disease present in that subject) it is considered that the subject is at a more advanced stage of the disease if the subject goes from being classified at stage III-IV or a stage V-VI or if the subject goes from being classified as stage III-IV to being classified as stage V-VI stage of AD.

The expression "advancement of Parkinson's disease" as used herein, refers to the subject being at a more evolved stage of the disease with respect to the stage where the subject was diagnosed. That is, if the subject was classified as stage I-II of PD (according to brain impairment and/or symptoms or clinical manifestations of disease present in that subject) it is considered that the subject is in a more advanced stage of the disease if the subject goes from being classified as stage III-IV or at stage V-VI or if the subject goes from being classified as stage III-IV to being classified as stage V-VI of PD.

In a specific embodiment of the third method of the invention, the sample comprising mitochondrial DNA is selected from a biopsy of a solid tissue or biofluid. The samples can be obtained by conventional methods known to the persons skilled in the art In an even more specific embodiment, the biofluid is selected from peripheral blood or cerebrospinal fluid.

In an even more specific embodiment, said solid tissue is brain tissue.

In a preferred embodiment of the invention, if the progression of Parkinson's disease is monitored, said brain tissue sample is obtained from the substantia nigra.

In a particular embodiment, the third method of the invention involves determining in a sample of a subject containing mitochondrial DNA, the methylation pattern in at least one site selected from the CpG sites in the D-loop region, shown in table 1.

In a specific embodiment, the third method of the invention involves determining the methylation pattern of at least one CpG site in the D-loop region selected from the sites shown in Table 1. In another specific embodiment, the first method of the invention involves determining the methylation pattern in at least 2, at least 3, at least 4, at least 5, at least 6, at least 7, at least 8, at least 9, at least 10, at least 11, at least 12, at least 13, at least 14, at least 15 or at least 16 CpG sites selected from Table 1.

In a still more specific and preferred embodiment of the invention, the third method of the invention comprises determining the methylation pattern of all of the CpG sites in the D-loop region shown in Table 1.

In another specific embodiment, the third method of the invention comprises determining in a sample of a subject containing mitochondrial DNA, the methylation pattern in at least one site selected from the CpG sites in the ND1 gene shown in Table 2.

In another specific embodiment, the third method of the invention involves determining the methylation pattern in a CpG site in the ND1 gene selected from the sites shown in Table 2.

In another specific embodiment, the third method of the invention involves determining the methylation pattern in at least 2, at least 3, at least 4, at least 5 or at least 6 CpG sites selected from Table 2.

In a still more specific and preferred embodiment of the invention, the third method of the invention involves determining the methylation pattern in all of the CpG sites in the ND1 gene shown in Table 2.

In a specific embodiment, the third method of the invention involves determining in a sample of a subject containing mitochondrial DNA, the methylation pattern in at least one site selected from the CHG sites in the D-loop region, shown in Table 3.

In a specific embodiment, the third method of the invention involves determining the methylation pattern in at least one CHG site in the D-loop region selected from the sites shown in Table 3. In another specific embodiment, the third method of the invention involves determining the methylation pattern in at least 2, at least 3, at least 4, at least 5, at least 6, at least 7, at least 8, at least 9, at least 10, at least 11, at least 12, at least 13 or at least 14 or 15 CHG sites selected from Table 3.

In a still more specific and preferred embodiment of the invention, the third method of the invention involves determining the methylation pattern in all of the CHG sites in the D-loop region shown in Table 3.

In another specific embodiment, the third method of the invention involves determining in a sample of a subject containing mitochondrial DNA, the methylation pattern in at least one site selected from the CHG sites in the ND1 gene, shown in Table 4.

In another specific embodiment, the third method of the invention involves determining the methylation pattern in at least one CHG site in the ND1 gene selected from the sites shown in Table 4. In another specific embodiment, the third method of the invention involves determining the methylation pattern in at least 2, at least 3, at least 4, at least 5, or at least 6 CpG sites selected from Table 4.

In a still more specific and preferred embodiment of the invention, the third method of the invention involves determining the methylation pattern in all of the CHG sites of the ND1 gene shown in Table 4.

In another specific embodiment, the third method of the invention involves determining in a sample of a subject containing mitochondrial DNA, the methylation pattern in at least one site selected from the CHH sites in the D-loop region, shown in Table 5.

In another specific embodiment, the third method of the invention involves determining the methylation pattern in at least one CHH site in the D-loop region selected from the sites shown in Table 5. In another specific embodiment, the third method of the invention involves determining the methylation pattern in at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28 at least 29, at least 30, at least 31, at least 32, at least 33, at least 34, at least 35, at least 36, at least 37, at least 38, at least 39, at least 40, at least 41, at least 42, or at least 43 CHH sites selected from Table 5.

In a still more specific and preferred embodiment of the invention, the third method of the invention involves determining the methylation pattern in all of the CHH sites in the D-loop region shown in Table 5.

In preferred methods of embodiment, the third method of the invention includes:
i. determination of the methylation pattern in all of the CpG sites in the D-loop region shown in Table 1 and in all of the CpG sites in the ND1 gene shown in Table 2
ii. determination of the methylation pattern in all of the CpG sites in the D-loop region shown in Table 1 and in all CHG sites of the D-loop region shown in Table 3,
iii. determination of the methylation pattern in all of the CpG sites in the D-loop region shown in Table 1 and in all of the CHG sites in the ND1 gene shown in Table 4,
iv. determination of the methylation pattern in all CpG sites in the D-loop region shown in Table 1 and in all CHH sites in the D-loop region shown in Table 5, v. determination of the methylation pattern in all CpG sites of the ND1 gene shown in Table 2 1 and in all the CHG sites in the D-loop region shown in Table 3, vi. determination of the methylation pattern in all of the CpG sites in the ND1 gene shown in Table 2 and in all of the CHG sites in the ND1 30 gene shown in Table 4, vii. determination of the methylation pattern in all CpG sites in the ND1 gene shown in Table 2 and in all the CHH sites in the D-loop region shown in Table 5.

viii. determination of the methylation pattern in all of the CHG sites in the D-loop region shown in Table 3 and all of the CHG sites in the ND1 gene shown in Table 4 and/or ix. determination of the methylation pattern in all of the CHG sites in the D-loop region shown in Table 3 x. determination of the methylation pattern in all CHG sites in the ND1 gene shown in Table 4 and in all the CHH sites in the D-loop region shown in Table 5.

Suitable methods to determine the methylation pattern in a sample of a subject containing mitochondrial DNA methods have been described in detail in the context of the first method of the invention.

In another specific embodiment, the third method of the invention involves determining the methylation pattern in said CpG, CHG and/or CHH sites through a technique selected from the group consisting of Methylation Specific PCR (MSP), a method based on enrichment. (e.g. MeDIP, MBD-seq and MethylCap), bisulfite sequencing and through a bisulphite based method (eg. RRBs, Infinium, Golden-Gate, Cobra, MSP, MethyUght) and a method by restriction of digestion (e.g., MRE-seq, or HELP trial), pyrosequencing, or differential conversion, differential restriction, differential weight of the methylated DNA CpG, CHG and/or CHH sites.

In a specific and preferred embodiment of the invention the methylation pattern of one or more CpG, CHG and/or CHH sites in the D-loop region and/or one or more CpG or CHH sites in the ND1 gene, according to the third method of the invention, is determined by pyrosequencing.

In another specific embodiment, the third method of the invention involves determining the methylation pattern of all CpG sites, all CHG sites and all CHH sites in the D-loop region shown in Tables 1, 3 and 5, and the methylation pattern of all CpG sites and all of all the CHG sites in the ND1 gene shown in Tables 2 and 4.

Fourth Method of the Invention

The authors of the present invention have discovered a single nucleotide polymorphism (SNP) in the D-loop region of mitochondrial DNA that is statistically associated with the development of Alzheimer's disease if the SNP is in at least 60% of the mtDNA molecules of a subject.

Therefore, in the fourth feature, the invention relates to an in vitro method to diagnose or determine the risk of developing Alzheimer's disease in a subject (hereinafter, the fourth method of the invention) that involves determining in a sample that contains mitochondrial DNA of said subject the nucleotide at the polymorphic position 16519 according to the sequence defined under accession number NC_012920 (SEQ ID NO: 1) in the NCBI database, where detection of the nucleotide C at said polymorphic position or the presence of the nucleotide C at said polymorphic position in at least 60% of the mitochondrial DNA molecules of said subject is indicative that the subject suffers from said disease or that the subject has an elevated risk of developing the disease.

The terms "diagnosis", "determine the risk", "sample" and "mitochondrial DNA" have been defined in the context of the first, second and third method of the invention and are used with the same meaning in the fourth method of the invention.

The presence of a specific nucleotide at a polymorphic position can be defined as the percentage of DNA molecules having such nucleotide at said polymorphic position with respect to the total of DNA molecules present in the sample. According to the fourth method of the invention it is considered that the subject is suffering from Alzheimer's disease or that the subject has an elevated risk of developing said disease if the mtDNA of said subject presents the nucleotide C at the polymorphic position 16519 according to the sequence defined under the accession number NC_012920 when the percentage of molecules that present said nucleotide at that position is at least 60%, at least 65%, at least 70%, at least 75%, at least 80%, at least 85%, at least 90% or more.

In a specific embodiment, it is considered that the subject has Alzheimer's disease or that the subject has an elevated risk of developing the disease if the MtDNA of said subject presents the nucleotide C at the polymorphic position 16519 according to the sequence defined under the accession number NC_012920 in 60% of mtDNA molecules. In a preferred embodiment of the invention it is considered that the subject has Alzheimer's disease or that the subject has an elevated risk of developing said disease if the MtDNA of said subject presents the nucleotide C at the polymorphic position 16519 according to the sequence defined under the accession number NC_012920 in 71% of mtDNA molecules.

In another preferred embodiment of the invention, it is considered that the subject has Alzheimer's disease or the subject is at a high risk of developing the disease if the mtDNA from said subject presents the nucleotide C at the polymorphic position 16519 according to the sequence defined under accession number NC_012920 in 74% of mtDNA molecules. In a preferred embodiment of the invention it is considered that the subject has Alzheimer's disease or that the subject is at a high risk of developing said disease if the MtDNA of said subject presents the nucleotide C at the polymorphic position 16519 according to the sequence defined under the accession number NC_012920 in 78% of mtDNA molecules.

As the person skilled in the art knows, a sample containing mitochondrial DNA can be homoplasmic or heteroplasmic. The term "heteroplasmy" or "heteroplasmic mitochondrial DNA" as used herein, refers to mitochondrial DNA of a subject that consists of a mixture of DNA from at least two different genotypes of mitochondria. The term "homoplasmia" or "homoplasmic mitochondrial DNA" as used herein refers to mitochondrial DNA of a subject that is formed by a single genotype of DNA from a single mitochondrial genotype.

In a specific embodiment, in the context of the present invention the sample of mitochondrial DNA is homoplasmic, in which case all mitochondria present in the subject contains identical genetic material so all mitochondria of a subject present in their genome nucleotide C at the polymorphic position 16519 according to the sequence defined under the accession number NC_012920. In those embodiments wherein the sample of mitochondrial DNA is homoplasmic, the fourth method of the invention allows to diagnose or determine the risk of developing Alzheimer's disease in a subject by detecting the C nucleotide in the polymorphic position 16519 according to the sequence defined under accession number NC_012920 in said mitochondrial DNA sample; that is, the detection of the nucleotide C at the polymorphic position 16519 according to sequence defined under the accession number NC_012920 in a sample of homoplasmic mitochondrial DNA from a subject is indicative that the subject suffers from Alzheimer's disease or that the subject has an elevated risk of developing the disease. Conversely, the detection of the nucleotide T at the polymorphic position 16519 according to the sequence as defined under the accession number NC_012920 in a sample of homoplasmic mitochondrial DNA, indicates that the subject is not suffering from Alzheimer's disease or that the subject has a low risk of developing the disease.

In another specific and preferred embodiment of the invention, the mitochondrial DNA sample is heteroplasmic, i.e. mtDNA subject is from two mitochondrial populations whose genetic material are not identical to each other. According to this invention, heteroplasmy refers to the fact that a percentage of said mitochondria of said subject present in its genome the oligonucleotide C at the polymorphic position 16519 according to the sequence defined under accession number NC_012920 and the remaining percentage of mitochondria of said subject presents the oligonucleotide T in its in its genome at the polymorphic position 16519 according to the sequence defined under accession number NC_012920.

The person skilled in the art will understand that the identification of the presence of polymorphism in at least 60% of mtDNA molecules is equally useful in order to select a subject for submission to preventive treatment of Alzheimer's disease, in cases where the mtDNA of the subject present heteroplamsy, as in the cases where the mtDNA of the subject present homoplamy, the totality of molecules will present the nucleotide T or the nucleotide C at position 16519, in which case the percentage of mtDNA molecules with polymorphisms indicative that the patient is a candidate to receive preventative treatment for Alzheimer's disease is either 100% or 0%. Like that, in the case of subjects whose mtDNA is heteroplasmic, there will be a population of MtDNA molecules that present the T nucleotide in position 16519 and a second population of molecules that present the C nucleotide in position 16519. In that case, it is considered that the patient is candidate for a preventive treatment of Alzheimer's disease when the percentage of mtDNA molecules that present nucleotide C at position 16519 is equal to or greater than 60%.

The determination of homoplasmy and heteroplasmy and the percentage of heteroplasmy or the "degree of heteroplasmy" can be determined by any technique known by a person skilled so in the art non-limiting illustrative examples of techniques to allow to determine whether a sample of mitochondrial DNA is heteroplastic include but are not limited to southern-blot, or PCR-RFLP of mtDNA sequencing. Briefly, the PCR-RFLP technique is based on the fact that normally the presence of a SNP in a sample is associated with the creation or destruction of specific sequences or target of one or more restriction enzymes. Heteroplasmy detection by PCR-RFLP technique is a first stage in the amplification of the genetic material region containing the polymorphism to be detected, by using specific oligonucleotides, followed by a second step where the amplified fragments are subjected to enzymatic digestion reaction in the presence of appropriate restriction enzyme. Since the presence or absence of the polymorphism in the sample is associated with the presence or absence of target specific restriction pattern obtained fragment sizes determine whether the sample is formed by a unique pattern of bands, in which case the sample is homoplasmic. If, however, the analysis determines the presence of two banding patterns, corresponding to two different mitochondrial DNA populations, then the mtDNA sample is heteroplasmic.

The term "single nucleotide polymorphism" or "single nucleotide polymorphism" or "SNP", as used herein, refers to a variation in the nucleotide sequence of a nucleic acid that occurs in a single nucleotide (A, C, T or G), where every possible sequence is present in a proportion equal to or greater than 1% of the population. These polymorphisms appear when a single nucleotide in the genome is altered (for example by substitution, addition or deletion). Each version of the sequence with respect to the polymorphic site is referred to as an allele of the polymorphic site. SNPs tend to be evolutionarily stable from generation to generation and, as such, can be used to study specific genetic abnormalities in a population.

The polymorphic variant of the invention is the position 16519 based on the numbering defined by the number NC_012920 in the NCBI database. The polymorphic variant contains a C in said position.

The terms "sequence determination of a SNP" or "detecting a SNP" are used interchangeably herein, and refer to the determination of a sequence of a particular SNP in the subject under study. Determining the sequence of the SNP can be performed by various processes known to the person skilled in the art.

In some specific embodiments of the invention, the sample comprising mitochondrial DNA is selected from a biopsy of a solid tissue or biofluid. The samples can be obtained by conventional methods known to the person skilled in the art.

In an even more specific embodiment, the biofluid is selected from peripheral blood or cerebrospinal fluid.

In an even more specific embodiment, said solid tissue is brain tissue.

If the material in which it is desired to determine said SNP according the present method is a solid tissue or biofluid, preferably there is a prior nucleic acid extraction from the sample using any suitable technique for this.

In a preferred embodiment of the invention, the DNA fraction suitable for the implementation of the invention is the total DNA. DNA extraction may be carried out using any method known to the person skilled in the art as has been detailed in the first method of the invention.

If desired, the present method can be carried out in samples which previously the mitochondrial fraction has been isolated and subsequently the DNA thereof has been isolated. The isolation of the mitochondrial fraction can be performed using any known method of cell fractionation and have been detailed in the first method of the present invention.

After isolating and amplifying (if necessary) the nucleic acid, the SNP sequence of the invention is detected by any method or technique capable of determining nucleotides present in a SNP or polymorphism. For example, a SNP can be detected by performing sequencing, mini-sequencing, hybridization, restriction fragment analysis, oligonucleotide ligation assay, allele-specific PCR, or a combination thereof. As such, the systems and methods limited to, nucleic acid sequencing, hybridization methods and array technology (e.g. technology available BioSciences Aclara, Affymetrix, Agilent Technologies, Inc. Illumina, etc); can also be used in techniques based on mobility shift of nucleic acid fragments amplified, for example Single Stranded Conformational Polymorphism (SSCP), denaturing gradient gel electrophoresis (DGGE), Chemical Mismatch Cleavage (CMC), Restriction Fragment Polymorphisms (RFLP), PCR-RFLP, WAVE analysis and the like (Methods Mol. Med. 2004; 108: 173-88). Of course, this list is merely illustrative and in no way limiting. The experts in the field may use any method appropriate to achieve such detection.

In another specific embodiment, determining the sequence of said SNP is performed by PCR-RFLP.

In a specific embodiment, the fourth method of the invention corresponds to an in vitro method to diagnose early stages of AD. The term "early stages of Alzheimer's disease" as used herein, refers to Alzheimer's disease stage I-II according to Braak scale defined in the context of the first method of the invention.

Fifth Method of the Invention

In the fifth feature, the invention corresponds to an in vitro method to select a subject for submission to a preventive treatment of Alzheimer's disease that involves determining in a sample containing mitochondrial DNA from said subject, the nucleotide at the polymorphic position 16519 according to the sequence with accession number NC_012920 in the NCBI database, wherein the detection of the C nucleotide at said polymorphic position or the presence of the nucleotide C at said polymorphic position in at least 60% of the mitochondrial DNA molecules indicative that the subject is a candidate to receive treatment aimed at preventing Alzheimer's disease.

The terms "Alzheimer", "treatment", "sample" mitochondrial DNA" and "polymorphism" as well as methods for obtaining the sample and detecting a polymorphism have been detailed in the context of the first, second, third and fourth method of the invention and are used here with the same meaning.

According to the fifth method of the invention it is considered that the subject is a candidate to be submitted to treatment aimed at preventing Alzheimer's disease if the mtDNA of the subject has nucleotide C at the polymorphic position 16519 according to the sequence defined under access number NC_012920 when the percentage of mtDNA molecules that have said nucleotide in said position is at least 60%, at least 65%, at least 70%, at least 75%, at least 80%, at least 85%, at least 90% or more. In a specific embodiment, it is considered that the subject is eligible to receive preventive treatment of Alzheimer's disease if the mtDNA of said subject presents the nucleotide C at the polymorphic position 16,519 according the sequence defined under accession number NC_012920 in 60% of mtDNA molecules.

The person skilled in the art will understand that the identification of the presence of the polymorphism in at least 60% of mtDNA molecules is equally useful to select a subject to be submitted to preventive treatment of Alzheimer's disease in cases where mtDNA of the subject present heteroplasmic as in the cases which it presents homoplasmic. Like that, as in the case of subjects whose mtDNA is homoplasmic, the totality of the molecules will present the nucleotide T or the nucleotide C at position 16519, in which case the percentage of mtDNA molecules with the polymorphisms indicative that the patient is a candidate to receive preventative treatment for Alzheimer's disease is either 100% or 0%. Like that, in the case of subjects whose mtDNA is heteroplasmic, there will be a population of mtDNA molecules which present the T nucleotide at position 16519 and a second population of molecules will present the C nucleotide at the position 16519. In that case, it will be considered that the patient is a candidate for preventive treatment of Alzheimer's disease when the percentage of molecules of mtDNA present the nucleotide C in position 16519 is less than or greater than 60%.

In some specific embodiments of the invention, the sample comprising mitochondrial DNA is selected from a biopsy of a solid tissue or biofluid, samples can be obtained by conventional methods known to the person skilled in the art.

In a specific embodiment, in the context of the present invention the sample of mitochondrial DNA is homoplasmic, in which case all mitochondria present in the subject contains identical genetic material so all mitochondria of a subject present nucleotide C in their genome in the polymorphic position 16519 according to the sequence under the accession number NC_012920. In those embodiments where the mitochondrial DNA sample is homoplasmic, the fifth method of the invention allows selecting a patient to be submitted to preventive treatment of Alzheimer's disease through the detection of the nucleotide C at the polymorphic position 16519 according to the sequence defined under accession number NC_012920 in said mitochondrial DNA sample; i.e. detection of nucleotide C at the polymorphic position 16519 according to the sequence defined under accession number NC_012920 in a sample of homoplasmic mitochondrial DNA from a patient is indicative that the subject is eligible to receive preventive treatment of Alzheimer's disease. Conversely, detection of nucleotide T in at polymorphic position 16519 according to the sequence defined under accession number NC_012920 in a sample of homoplasmic mitochondrial DNA from a patient is indicative that said patient is not a candidate to receive preventive treatment for Alzheimer's disease.

In another specific and preferred embodiment of the invention, the mitochondrial DNA sample is heteroplasmic, i.e. the mtDNA of the subject is of two mitochondrial populations whose genetic material are not identical to each other. According to the present invention heteroplasmy refers to a percentage of mitochondria of said subject that present in its genome the oligonucleotide C in the polymorphic position 16519 according to the sequence defined under the accession number NC_012920 and the remaining percentage of mitochondria of said subject present oligonucleotide T in the genome in the polymorphic position 16519 according to the sequence defined under accession number NC_012920.

Methods for determining whether a sample is homoplasmic or heteroplasmic as well as to determine the degree of heteroplasmy of a sample have been detailed in the context of the fourth method of the invention and are incorporated herein by reference.

In an even more specific embodiment, the biofluid is selected from peripheral blood or cerebrospinal fluid.

In an even more specific embodiment, said solid tissue is brain tissue.

If the material in which it is desired to determine said SNP according the present method is a solid tissue or biofluid, preferably there is a prior nucleic acid extraction from the sample using any suitable technique for this. In a preferred embodiment of the invention, the DNA fraction suitable for the implementation of the invention is the total DNA. The extraction of DNA may be carried out using any appropriate method known to persons skilled in the art as has been detailed in the first method of the invention.

In another specific embodiment, determining the sequence of said SNP is performed by PCR-RFLP.

Polynucleotides of the Invention

In another feature, the present invention corresponds to a nucleic acid (hereinafter "first polynucleotide of the invention") Comprising at least 9 contiguous polynucleotides in a mtDNA region wherein said region comprises at least one methylation site selected from the CpG sites in the D-loop region shown in Table 1.

The term "polynucleotide" as used herein, refers to DNA or RNA molecules of more than 13 bases in length. The polynucleotides of the invention are preferably DNA molecules of at least 14, at least 15, at least 16, at least 18, at least 20, at least 25, at least 30, at least 35, at least 40, at least 50, at least 60, at least 70, at least 80, at least 90, at least 100 or more bases in length.

In a specific embodiment, the first polynucleotide of the invention comprises at least 9, at least 10, at least 11, at least 12, at least 13, at least 14, at least 15, at least 20, at least 25, at least 30 or more contiguous nucleotides to at least one CpG site selected from Table 1.

In another feature, the present invention relates to a nucleic acid (hereinafter "second polynucleotide of the invention") comprising at least 9 contiguous polynucleotide in a mitochondrial DNA region wherein said region contains at least one methylation site selected from CpG sites in the ND1 gene shown in Table 2

In a specific embodiment, the second polynucleotide of the invention comprises at least 9, at least 10, at least 11, at least 12, at least 13, at least 14, at least 15, at least 20, at least 25, at least 30 or more contiguous nucleotides, to said at least one CpG site selected from Table 2. In another feature, the present invention relates to a nucleic acid (hereinafter "second polynucleotide of the invention") comprising at least 9 contiguous polynucleotide in a mitochondrial DNA region wherein said region comprises at least one methylation site selected from the CHG sites in the D-loop region shown in Table 3.

In a specific embodiment, the third polynucleotide of the invention comprises at least 9, at least 10, at least 11, at least 12, at least 13, at least 14, at least 15, at least 20, at least 25, at least 30 or more contiguous nucleotides, to said at least one CHG site selected from Table 3.

In another feature, the present invention relates to a nucleic acid (hereinafter "fourth polynucleotide of the invention") comprising at least 9 contiguous polynucleotide in a mitochondrial DNA region wherein said region contains at least one methylation site selected from CHG sites of the ND1 gene shown in Table 4.

In a specific embodiment, the fourth polynucleotide of the invention comprises at least 9, at least 10, at least 11, at least 12, at least 13, at least 14, at least 15, at least 20, at least 25, at least 30 or more contiguous nucleotides to said at least one CHG site selected from Table 4.

In another aspect, the present invention refers to a nucleic acid (hereinafter 35 hereinafter "fifth polynucleotide of the invention") comprising at least 9 contiguous polynucleotide in a mtDNA region wherein said region comprises at least one methylation site selected from the CHH sites in the D-loop region shown in Table 5.

In a specific embodiment, the fifth polynucleotide of the invention comprises at least 9, at least 10, at least 11, at least 12, at least 13, at least 14, at least 15, at least 20, at least 25, at least 30 or more contiguous nucleotides, to said at least one CHH site selected from Table 5.

In another feature, the present invention corresponds to a nucleic acid (hereinafter "sixth polynucleotide of the invention") Comprising at least 9 contiguous polynucleotide in a mitochondrial DNA region wherein said region comprises at least one methylation site selected from the CpG sites in the D-loop region shown in Table 1, wherein the corresponding position of cytosine in said CpG site is uracil.

In a particular embodiment, the sixth polynucleotide of the invention comprises at least 9, at least 10, at least 11, at least 12, at least 13, at least 14, at least 15, at least 20, at least 25, at least 30 or more contiguous nucleotides, to said at least one CpG site selected from Table 1 wherein the corresponding position of cytosine in said CpG site is uracil.

In another aspect, the present invention refers to a nucleic acid (hereinafter "seventh polynucleotide of the invention") comprising at least 9 contiguous polynucleotides in a mitochondrial DNA region wherein said region comprises at least one methylation site selected from the CpG sites of the ND1 gene shown in Table 2, wherein the corresponding position of cytosine in said CpG site is uracil.

In a particular embodiment, the seventh polynucleotide of the invention comprises at least 9, at least 10, at least 11, at least 12, at least 13, at least 14, at least 15, at least 20, at least 25, at least 30 or more contiguous nucleotides to said at least one CpG site selected from Table 2 wherein the corresponding position of cytosine in said CpG site is uracil.

In another feature, the present invention refers to a nucleic acid (hereinafter "eight polynucleotide of the invention") Comprising at least 9 contiguous polynucleotides in mitochondrial DNA region wherein said region comprises at least one methylation site selected from the CHG sites in the D-loop region shown in Table 3 wherein the corresponding position of cytosine in said CHG site is uracil.

In a particular embodiment, the eight polynucleotide of the invention comprises at least 9, at least 10, at least 11, at least 12, at least 13, at least 14, at least 15, at least 20, at least 25, at least 30 or more contiguous nucleotides to said at least one CHG site selected from Table 3, wherein the corresponding position of cytosine in said CHG site is uracil.

In another feature, the present invention relates to a nucleic acid (hereinafter "ninth polynucleotide of the invention") comprising at least 9 contiguous polynucleotides in a mitochondrial DNA region wherein said region comprises at least one methylation site selected from the CHG sites of the ND1 gene shown in Table 4, wherein the corresponding position of cytosine in said CHG site is uracil.

In a specific embodiment, the ninth polynucleotide of the invention comprises at least 9, at least 10, at least 11, at least 12, at least 13, at least 14, at least 15, at least 20, at least 25, at least 30 or more contiguous nucleotides, that is said, at least one CHG site selected from Table 4, wherein the corresponding position of cytosine in said CHG site is uracil.

In another feature, the present invention relates to a nucleic acid (hereinafter "tenth polynucleotide of the invention") Comprising at least 9 contiguous polynucleotide in a mitochondrial DNA region wherein said region comprises at least one methylation site selected from the CHH sites in the D-loop region shown in Table 5, wherein the corresponding position of cytosine in said CHH site is uracil.

In a specific embodiment, the tenth polynucleotide of the invention comprises at least 9, at least 10, at least 11, at least 12, at least 13, at least 14, at least 15, at least 20, at least 25, at least 30 or more contiguous nucleotides to said at least one CHH site selected from Table 5, wherein the corresponding position of cytosine in said CHH site is uracil.

In another feature, the invention relates to a polynucleotide that specifically hybridises with said first, second, third, fourth, fifth, sixth, seventh, eighth, ninth and tenth polynucleotides of the invention.

The expression "that specifically hybridises" or "capable of hybridising in a specific form", as used herein, refers to the ability of an oligonucleotide or of a polynucleotide of specifically recognizing a sequence of a CpG, CHG or CHH site. As used herein the term "hybridization" It is the process of combining two nucleic acid molecules or single-stranded molecules with a high degree of similarity resulting in a simple double-stranded molecule by specific pairing between complementary bases. Normally hybridization occurs under very stringent conditions or moderately stringent conditions.

As known in the technology, the "similitude" between two nucleic acid molecules is determined by comparing the nucleotide sequence of a molecule to the nucleotide sequence of a second molecule. The variants according to the present invention include nucleotide sequences that are at least 60%, 65%, 70%, 75%, 80%, 85%, 90%, or 95% similar or identical to the sequence of said at least one CpG, CHH and CGH site selected from the sites shown in Tables 1 to 5. The degree of identity between two nucleic acid molecules is determined using computer algorithms and methods that are widely known to persons skilled in the art. The identity between two amino acid sequences preferably determined by BLASTN algorithm (BLAST Manual, Altschul et al, 1990, NCBI NLM NIH Bethesda, Md. 20894, Altschul, S., et al, J. Mol Biol. 215: 403-10).

The "rigor" of hybridization reactions is readily determined by an ordinary expert in the field, and generally is an empirical calculation dependent upon probe length, washing temperature, and salt concentration. In general, longer probes require higher temperatures for proper annealing while shorter probes need lower temperatures. Hybridization generally depends on the ability of denatured DNA to reanneal when complementary strands are present in an environment below their melting temperature. The higher the degree of desired homology between the probe and hybridisable sequence, the higher the relative temperature that can be used. As a result, it is deduced that higher relative temperatures would tend to make the reaction conditions more stringent, while lower temperatures less so. For additional details and explanation of stringency of hybridization reactions, see Ausubel et al., Current Protocols in Molecular Biology, Wiley Interscience Publishers, (1995).

The term "stringent conditions" or "high stringency conditions" as used herein, typically: (1) employ low ionic strength and high temperature for washing, for example 0.015 M sodium chloride/0.0015 citrate/0.1% sodium dodecyl sulfate at 50° C. sodium; (2) employ during hybridization a denaturing agent such as formamide, for example, 50% (v/v) formamide with 0.1% bovine serum albumin/ 0.1% Ficoll/0.1% polyvinylpyrrolidone/50 mM buffer sodium phosphate at pH 6.5 with 750 mM sodium chloride, 75 mM citrate sodium at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, DNA sonicated salmon sperm (50 mg/ml), 0.1% SDS, and 10% dextran sulfate at 42° C., with washes at 42° C. in 0.2×SSC (sodium chloride/sodium citrate) and 50% formamide, followed by a high-stringency wash 0.1×SSC consisting containing EDTA at 55° C.

"Moderately stringent conditions" may be identified as described by Sambrook et al, Molecular Cloning. A Laboratory Manual, New York: Cold Spring Harbor Press, 1989, and include the use of washing solution and hybridization conditions (e.g., temperature, ionic force and % SDS) less stringent than those described above. An example of moderately stringent conditions is overnight incubation at 37° C. in a solution comprising: 20% formamide, 5×SSC (150 mM NaCl, 15 mM trisodium citrate), 50 mM sodium phosphate (pH7.6), 5×Denhardt's solution, 10% dextran sulfate and 20 mg/ml salmon sperm DNA denatured fragmented, followed by washing the filters in 1×SSC at about 35 37-50° C. the person skilled in the art will know how to adjust the temperature, ionic strength, etc. if necessary to accommodate factors such as probe length and the like.

Kits of the Invention

In another feature, the present invention relates to a kit (hereinafter "first kit of the invention") Comprising at least one oligonucleotide capable of specifically hybridizing and methylation-dependent manner with a mitochondrial DNA sequence comprising a methylation site selected from the group formed by:
   (i) the CpG sites in the D-loop region shown in Table 1,
   (ii) the CpG sites in the ND1 gene shown in Table 2,
   (iii) the CHG sites in the D-loop region shown in Table 3,
   (iv) the CHG sites in the ND1 gene shown in Table 4, and/or
   (v) the CHH sites in the D-loop region shown in Table 5

The terms "CpG site", "CHG site", "CHH site", "D-loop region" and "ND1 gene" have been described in detail in the context of the first method of the invention and the term "capable of hybridising in a specific form" is defined in the context of the polynucleotides of the invention. These terms are used with the same meaning in the context of the invention kits.

In a preferred embodiment, the oligonucleotides are part of the invention kit which is capable of specifically hybridizing dependently from methylation with a mitochondrial DNA sequence comprising a methylation site selected from the group consisting of:
   (i) the CpG sites in the D-loop region shown in Table 1,
   (ii) the CpG sites in the ND1 gene shown in Table 2,
   (iii) the CHG sites in the D-loop region shown in Table 3,
   (iv) the CHG sites in the ND1 gene shown in Table 4, and/or
   (v) the CHH sites in the D-loop region shown in Table 5

They constitute at least 10%, at least 20%, at least 30%, at least 40%, at least 50%, at least 60%, at least 70%, at least 80%, at least 90% or at least 100% of the total amount of the oligonucleotides that form the kit. In further embodiments, said oligonucleotides are at least 55% at least 60%, at least 65%, at least 70%, at least 75%, at least 80%, at least 90%, at least 95%, at least 96%, at least 97%, at least 98% or at least 99% of the total amount of oligonucleotides which form the kit.

Suitable kits include various reagents for use according to the present invention, in suitable containers and packaging materials, including tubes, vials, and shrink wrap packages and blow molders. In addition, invention kits can contain instructions for the simultaneous, sequential or separate use of the various components found in the kit. Such instructions may be in the form of printed material or in the form of electronic media capable of storing instructions so that they can be read by a subject, such as electronic storage media (magnetic disks, tapes and the like), optical media (CD-ROM, DVD) and the like. Additionally, or alternatively, the media can contain Internet addresses that provide such instructions.

Suitable materials for inclusion in an exemplary kit according to the present invention comprise one or more of the following: reagents capable of amplifying a specific sequence of a domain either total or mtDNA DNA without the need to carry out PCR; reagents required to discriminate between the different possible alleles in the sequence domains amplified by PCR amplification or non-PCR (e.g., restriction endonuclease, hybridizing oligonucleotides preferably CpG, CHG and/or CHH sites methylated or unmethylated, including those modified to contain enzymes or fluorescent chemical groups that amplify the oligonucleotide signal and make that the discrimination between CpG, CHG and/or CHH methylated or unmethylated sites CHH is more robust); or reagents required for physically separating the various products amplified regions (e.g., agarose or polyacrylamide and a buffer for use in electrophoresis, HPLC columns, SSCP gels, formamide gels or a support matrix for MALDI-TOF).

The term "oligonucleotide" as used herein, refers to a DNA molecule or short RNA, with up to bases in length. Oligonucleotides of the invention are preferably DNA molecules at least 2, at least 3, at least 4, at least 5, at least 6, at least 7, at least 8, at least 9, at least 10, at least 15, at least 20, at least 30, at least 40, at least 45 or 50 bases of length.

As used in the kit of the invention, at least one oligonucleotide capable of hybridizing with at least a sequence of a CpG site in the D-loop region selected from the CpG sites shown in Table 1, at least one oligonucleotide capable of hybridizing with at least one sequence of a CpG site in the ND1 gene shown in Table 2, at least one oligonucleotide capable of hybridizing with at least one sequence of a CHG site in the D-loop region shown in Table 3, at least one oligonucleotide capable of hybridizing with at least one sequence of a CHG site in the ND1 gene shown in Table 4 and/or at least one oligonucleotide capable of hybridizing with at least one sequence of a CHH site in the D-loop region shown in Table 5, in a methylation specific manner, it is used as a primer to amplify the region containing said CpG, CHG and/or CHH site(s) Alternatively, at least one oligonucleotide can also be used as a probe to detect such CpG, CHG or CHH methylated or unmethylated sites.

In a preferred embodiment of the first kit of the invention comprise oligonucleotides capable of specifically hybridizing with all CpG sites in the D-loop region shown in Table 1, all CpG sites of the ND1 gene shown in Table 2, with all of the CHG sites of the D-loop region shown in Table 3, with all of CHG sites in the ND1 gene shown in Table 4 and/or all CHH sites in the D-loop region shown in Table 5.

If desired, the first kit of the invention may comprise a first oligonucleotide capable of specifically hybridizing with bisulfites-treated oligonucleotide comprising at least one sequence of a CpG site in the D-loop region shown in Table 1 when said CpG site is methylated, and at least one oligonucleotide or polynucleotide capable of specifically hybridizing with the same bisulfite-treated oligonucleotide comprising at least one sequence of a CpG site in the D-loop region when said CpG site is unmethylated; and/or the kit may comprise a first oligonucleotide capable of specifically hybridizing with bisulfites-treated oligonucleotide comprising at least one sequence of a CpG site in the ND1 gene shown in Table 2 when said CpG site is methylated, and at least one oligonucleotide or polynucleotide capable of specifically hybridizing with the same bisulfite-treated oligonucleotide comprising at least one sequence of a CpG site of the D-loop region when said CpG site is unmethylated; and/or the kit may comprise a first oligonucleotide capable of specifically hybridizing with a bisulfite-treated oligonucleotide comprising at least one sequence of a CHG site in the D-loop region shown in Table 3 when said CHG site is methylated, and at least one oligonucleotide or polynucleotide capable of specifically hybridizing with the same bisulfite-treated oligonucleotide that comprises at least a sequence of a CHG site of the D-loop region when said CHG site is not methylated; and/or the kit may comprise a first oligonucleotide capable of specifically hybridizing with bisulfite-treated oligonucleotide comprising at least one sequence of a CHG site in the ND1 gene shown in Table 4 when said site CHG is methylated, and at least one oligonucleotide or polynucleotide capable of hybridizing specifically with the same bisulfites-treated oligonucleotide that contains at least one sequence of a CHG site in the D-loop region when said CHG site is unmethylated; and/or the kit may comprise a first oligonucleotide capable of specifically hybridizing with bisulfites-treated oligonucleotide comprising at least a sequence of a CHH site in the D-loop region shown in Table 5 when said CHH site is methylated and at least one oligonucleotide or polynucleotide capable of specifically hybridizing the same bisulfite-treated oligonucleotide comprising at least one sequence of a CHH site in the D-loop region when said CHH site is unmethylated.

For hybridization of an unmethylated CpG site, specific primers that hybridize with non-methylated DNA, have, preferably, a T in the CG par in "to distinguish it from the C retained in methylated DNA. It is preferable that primers contain relatively few Cs or Gs in the sequence since the Cs will be absent in the sense primer and the Gs absent in the antisense primer (cytosine converted into uracil, which is amplified as thymidine in the amplification product). Accordingly, for hybridization to a methylated CpG site, primers that specifically hybridize methylated DNA preferably they have a C at the 3'CG pair.

In another feature, the invention relates to a kit (hereinafter "second kit 35 invention") comprising at least one oligonucleotide capable of hybridizing.

Specifically, with a zone in 5' to 3' position with respect to a methylation site of mitochondrial DNA selected from the group consisting of:
 i. the CpG sites in the D-loop region shown in Table 1,
 ii. the CpG sites in the ND1 gene shown in Table 2,
 iii. the CHG sites in the D-loop region shown in Table 3,
 iv. the CHG sites in the ND1 gene shown in Table 4, and/or
 v. the CHH sites in the D-loop region shown in Table 5
 where methylated cytosine in said position has converted to uracil or another base that is distinguishable from cytosine in its hybridization properties.

In a preferred embodiment, the oligonucleotides that form part of the kit of the invention and which are capable of specifically hybridizing to a region or position 5' or position 3' with respect to a methylation site in the mitochondrial DNA selected from the group formed by:
 i. the CpG sites in the D-loop region shown in Table 1,
 ii. the CpG sites in the ND1 gene shown in Table 2,
 iii. the CHG sites in the D-loop region shown in Table 3,
 iv. the CHG sites in the ND1 gene shown in Table 4, and/or
 v. the CHH sites in the D-loop region shown in Table 5

They constitute at least 10%, at least 20%, at least 30%, at least 40%, at least 50%, at least 60%, at least 70%, at least 80%, at least 90% or at least 100% of the total amount of the oligonucleotides that form the kit. In further embodiments, said oligonucleotides constitute at least 55% at least 60%, at least 65%, at least 70%, at least 75%, at least 80%, at least 90%, at least 95%, at least 96%, at least 97%, at least 98% or at least 99% of the total amount of oligonucleotides that make up the kit.

In a specific embodiment, the second kit of the invention further comprises one or more reagents to convert unmethylated cytosine to uracil or another base that is differentially detectable to cytosine in terms of hybridization properties.

In a preferred embodiment, the one or more reagents to convert unmethylated cytosine to uracil or another base that is detectably different from cytosine in terms of hybridization properties is bisulfite, preferably sodium bisulfite. The reagent capable of converting unmethylated cytosine to uracil or another base that is differentially detectable to cytosine in terms of hybridization properties is metabisulfite, preferably sodium metabisulfite.

The term "conversion reagent" and its details are described in detail in context of the diagnostic method of the invention and used with the same meaning in the context of the kit according to the invention.

In a specific embodiment, the second kit of the invention comprises at least one oligonucleotide comprising a sequence selected from the sequences shown in SEQ ID NO: 2, SEQ ID NO: 3, SEQ ID NO: 4 and/or SEQ ID NO: 5.

In another feature, the invention refers to the use of the first and/or second kit of the invention to determine the pattern of mitochondrial DNA in a subject or to determine the diagnosis of a neurodegenerative disease in a subject selected from Alzheimer's disease and Parkinson's disease.

The invention is described by the following examples which are to be construed as merely illustrative and not limitative of the scope of the invention

EXAMPLES

Materials and Methods
Study Design and Subjects Included

The study was conducted on 44 samples, including pathology related to Alzheimer's disease (AD), Parkinson's disease (PD) and control cases. The samples were processed in a plate divided into two lanes. In lane 1 amplicons D-Loop ND1 and samples were analyzed in entorhinal cortex cases related pathology EA and corresponding controls (Table 7). In lane 2 D-Loop amplicons were analyzed on samples of the substantia nigra in PD and its corresponding controls (Table 7). Each patient was identified in the primers used with MID (multiplex Identifier) (Tables 7 and 8). Methylation in CpG sites and non CpG sites (CHG and CHH, where H=A, T, or C) was analyzed using a pyrosequencer 454 GS FLX Titanium Roche that generated 569.684 sequences in lane 1, whose lengths varied from 40-1098 base pairs (bp) with an average length of about 417 bp. In lane 2 the number of sequences obtained was 513.579, whose length ranged from 40 to 933 bp (466 bp average length). Alignments of the sequences obtained for each MID, amplicon and lane against their respective reference sequences were noted and the percentages of identity between these were nearly 100%. The mean and median rates of bisulphite conversion for each locus and MID were analyzed.

The number of unmethylated sequences exceeded the number of methylated sequences identified in each site and some methylation sites were not present. Those sequences after alignment were found to have, at least, one not present site of the methylation pattern not, were removed from the analysis to avoid any bias at the time of quantization. This circumvents approximation analysis of putative mitochondrial pseudogenes whose amplicons presented nearly 100% of identity with mitochondrial DNA when analyzed in NCBI BLAST. Most CpG, CHG, and CHH sites analyzed were unmethylated. However, different methylation sites could be identified.

TABLE 6

Number of differentially methylated sites. FRD: p-value adjusted Benjamini method and Hocheberg (1995)

| Lane | Amplicon | Site | Criteria | No. of Sites | C vs. AD I-II | C vs. AD III-IV | AD I-II vs. AD III-IV | C vs. PD |
|---|---|---|---|---|---|---|---|---|
| L1 | D-loop | CG | FDR < 0.01 | 18 | 17 | 14 | 12 | — |
| L1 | D-loop | CG | FDR < 0.05 | 18 | 17 | 15 | 16 | — |
| L1 | ND1 | CG | FDR < 0.01 | 13 | 7 | 7 | 0 | — |
| L1 | ND1 | CG | FDR < 0.05 | 13 | 7 | 7 | 0 | — |
| L1 | D-loop | CHG | FDR < 0.01 | 16 | 13 | 10 | 1 | — |
| L1 | D-loop | CHG | FDR < 0.05 | 16 | 14 | 12 | 7 | — |
| L1 | ND1 | CHG | FDR < 0.01 | 9 | 6 | 5 | 0 | — |
| L1 | ND1 | CHG | FDR < 0.05 | 9 | 7 | 5 | 0 | — |
| L1 | D-loop | CHH | FDR < 0.01 | 52 | 0 | 0 | 34 | — |
| L1 | D-loop | CHH | FDR < 0.05 | 52 | 23 | 0 | 43 | — |
| L1 | ND1 | CHH | FDR < 0.01 | 72 | 0 | 0 | 0 | — |
| L1 | ND1 | CHH | FDR < 0.05 | 72 | 0 | 0 | 0 | — |
| L2 | D-loop | CG | FDR < 0.01 | 18 | — | — | — | 17 |
| L2 | D-loop | CG | FDR < 0.05 | 18 | — | — | — | 17 |
| L2 | D-loop | CHG | FDR < 0.01 | 16 | — | — | — | 14 |
| L2 | D-loop | CHG | FDR < 0.05 | 16 | — | — | — | 14 |
| L2 | D-loop | CHH | FDR < 0.01 | 52 | — | — | — | 44 |
| L2 | D-loop | CHH | FDR < 0.05 | 52 | — | — | — | 44 |

TABLE 7

Summary of key clinical features and neuropathological human cases analyzed. Braak stages Alzheimer's disease (AD) indicate the degree of presence of neurons with fibrillary neurodegeneration (roman numerals) and senile plaques (letters) following the classification of Braak. Braak stages for Parkinson's disease (PD) refers to the degree of presence of the protein α-synuclein (Lewy bodies).

| MID | Lane | Region of brain | Diagnosis | Stage of Braak for AD | Stage of Braak for PD | Gender | Age | Time postmortem (h) |
|---|---|---|---|---|---|---|---|---|
| 1 | L1 | entorhinal | CONTROL | 0/0 | 0 | M | 56 | 5 |
| 2 | L1 | entorhinal | CONTROL | 0/0 | 0 | M | 56 | 3.45 |
| 3 | L1 | entorhinal | CONTROL | 0/0 | 0 | F | 55 | 8.3 |
| 4 | L1 | entorhinal | CONTROL | 0/0 | 0 | F | 66 | 4.15 |
| 5 | L1 | entorhinal | CONTROL | 0/0 | 0 | F | 64 | 5 |
| 6 | L1 | entorhinal | CONTROL | 0/0 | 0 | F | 52 | 5.45 |
| 7 | L1 | entorhinal | CONTROL | 0/0 | 0 | M | 57 | 5.20 |
| 8 | L1 | entorhinal | CONTROL | 0/0 | 0 | M | 64 | 3.3 |
| 9 | L1 | entorhinal | AD associated | I/A | 0 | F | 57 | 5 |
| 10 | L1 | entorhinal | AD associated | I/A | 0 | F | 64 | 2.15 |
| 11 | L1 | entorhinal | AD associated | I | 0 | M | 59 | 16.3 |

TABLE 7-continued

Summary of key clinical features and neuropathological human cases analyzed.
Braak stages Alzheimer's disease (AD) indicate the degree of presence of neurons with
fibrillary neurodegeneration (roman numerals) and senile plaques (letters) following the
classification of Braak. Braak stages for Parkinson's disease (PD) refers to the degree of
presence of the protein α-synuclein (Lewy bodies).

| MID | Lane | Region of brain | Diagnosis | Stage of Braak for AD | Stage of Braak for PD | Gender | Age | Time postmortem (h) |
|---|---|---|---|---|---|---|---|---|
| 12 | L1 | entorhinal | AD associated | II/A | 0 | F | 86 | 4.15 |
| 13 | L1 | entorhinal | AD associated | I/A | 0 | M | 67 | 14.4 |
| 14 | L1 | entorhinal | AD associated | II/A | 0 | M | 66 | 4.55 |
| 15 | L1 | entorhinal | AD associated | I/A | 0 | F | 63 | 8.05 |
| 16 | L1 | entorhinal | AD associated | II/A | 0 | F | 76 | 5.45 |
| 17 | L1 | entorhinal | AD associated | III/A | 0 | F | 71 | 6.45 |
| 18 | L1 | entorhinal | AD associated | III-A | 0 | F | 77 | 11.5 |
| 19 | L1 | entorhinal | AD associated | III/B | 0 | M | 86 | 3.1 |
| 20 | L1 | entorhinal | AD associated | IV/C | 0 | F | 69 | 8.1 |
| 9 | L1 | entorhinal | AD associated | I/A | 0 | F | 57 | 5 |
| 10 | L1 | entorhinal | AD associated | I/A | 0 | F | 64 | 2.15 |
| 11 | L1 | entorhinal | AD associated | I | 0 | M | 59 | 16.3 |
| 12 | L1 | entorhinal | AD associated | II/A | 0 | F | 86 | 4.15 |
| 21 | L1 | entorhinal | AD associated | III | 0 | F | 79 | 3.4 |
| 22 | L1 | entorhinal | AD associated | IV/C | 0 | M | 75 | 6.1 |
| 23 | L1 | entorhinal | AD associated | III/A | 0 | F | 74 | 4 |
| 24 | L1 | entorhinal | AD associated | III/0 | 0 | M | 87 | 3.3 |
| 1 | L2 | SN | CONTROL | 0/0 | 0 | F | 78 | 3.4 |
| 2 | L2 | SN | CONTROL | 0/0 | 0 | M | 66 | 3 |
| 3 | L2 | SN | CONTROL | 0/0 | 0 | F | 71 | 8.3 |
| 4 | L2 | SN | CONTROL | 0/0 | 0 | M | 30 | 4.1 |
| 5 | L2 | SN | CONTROL | 0/0 | 0 | M | 47 | 5 |
| 6 | L2 | SN | CONTROL | 0/0 | 0 | M | 67 | 5 |
| 7 | L2 | SN | CONTROL | 0/0 | 0 | M | 39 | 9.15 |
| 8 | L2 | SN | CONTROL | 0/0 | 0 | M | 85 | 5.45 |
| 9 | L2 | SN | CONTROL | 0/0 | 0 | F | 46 | 9.35 |
| 10 | L2 | SN | CONTROL | 0/0 | 0 | F | 77 | 3.15 |
| 11 | L2 | SN | PD | 0/0 | 3.4 | M | 68 | 9.2 |
| 12 | L2 | SN | PD | 0/0 | 3.4 | F | 81 | 6.3 |
| 13 | L2 | SN | PD | 0/0 | 3.4 | M | 76 | 12.3 |
| 14 | L2 | SN | PD | 0/0 | 3.4 | F | 77 | 3.3 |
| 15 | L2 | SN | PD | 0/0 | 3.4 | F | 78 | 27.3 |
| 16 | L2 | SN | PD | 0/0 | 3.4 | F | 69 | 4.3 |
| 5 | L2 | SN | CONTROL | 0/0 | 0 | M | 47 | 5 |
| 6 | L2 | SN | CONTROL | 0/0 | 0 | M | 67 | 5 |
| 7 | L2 | SN | CONTROL | 0/0 | 0 | M | 39 | 9.15 |
| 8 | L2 | SN | CONTROL | 0/0 | 0 | M | 85 | 5.45 |
| 9 | L2 | SN | CONTROL | 0/0 | 0 | F | 46 | 9.35 |
| 10 | L2 | SN | CONTROL | 0/0 | 0 | F | 77 | 3.15 |
| 11 | L2 | SN | PD | 0/0 | 3.4 | M | 68 | 9.2 |
| 12 | L2 | SN | PD | 0/0 | 3.4 | F | 81 | 6.3 |
| 13 | L2 | SN | PD | 0/0 | 3.4 | M | 76 | 12.3 |
| 14 | L2 | SN | PD | 0/0 | 3.4 | F | 77 | 3.3 |
| 15 | L2 | SN | PD | 0/0 | 3.4 | F | 78 | 27.3 |
| 16 | L2 | SN | PD | 0/0 | 3.4 | F | 69 | 4.3 |
| 17 | L2 | SN | PD | I/O | 4 | M | 69 | 6 |
| 18 | L2 | SN | PD | 0/0 | 4 | F | 84 | 4.3 |
| 19 | L2 | SN | PD | 0/0 | 5 | M | 76 | 12 |
| 20 | L2 | SN | PD | 0/0 | 5 | M | 80 | 7.3 |

TABLE 8

MID sequence associated with each case analyzed

| number MID | MID sequence | SEQ ID NO: |
|---|---|---|
| 1 | ACGAGTGCGT | 6 |
| 2 | ACGCTCGACA | 7 |
| 3 | AGACGCACTC | 8 |
| 4 | AGCACTGTAG | 9 |
| 5 | ATCAGACACG | 10 |
| 6 | ATATCGCGAG | 11 |
| 7 | CGTGTCTCTA | 12 |
| 8 | CTCGCGTGTC | 13 |
| 9 | TAGTATCAGC | 14 |
| 10 | TCTCTATGCG | 15 |
| 11 | TGATACGTCT | 16 |
| 12 | TACTGAGCTA | 17 |
| 13 | CATAGTAGTG | 18 |
| 14 | CGAGAGATAC | 19 |
| 15 | ATACGACGTA | 20 |
| 16 | TCACGTACTA | 21 |
| 17 | CGTCTAGTAC | 22 |
| 18 | TCTACGTAGC | 23 |
| 19 | TGTACTACTC | 24 |
| 20 | ACGACTACAG | 25 |
| 21 | CGTAGACTAG | 26 |
| 22 | TACGAGTATG | 27 |
| 23 | TACTCTCGTG | 28 |
| 24 | TAGAGACGAG | 29 |

Human Brain Samples

Tissue samples were provided by the Neurological Tissue Bank, University of Barcelona—Hospital de Barcelona and the Bank of Institute of Neuropathology, HUB-ICO-IDI-BELL. The donation and procurement of samples was regulated by the ethics committee of both institutions. Half of each brain was maintained in buffered formalin 4% solution for morphological and histological study, while the other half was processed in coronal sections to be frozen at −80 C to be available for biochemical studies. Neuropathological examination in all controls and pathological cases took place in thirty standardized sections of the brain, cerebellum and brain stem, which were stained with hematoxylin and eosin, and Klüver Barrera, or processed for immunohistochemistry for glial fibrillary acidic protein, microglial markers, beta-amyloid, phosphorylated tau (AT8 antibody) α-synuclein, β-crystallin, ubiquitin and TDP-43. Cases with pathology related to AD and PD were classified according to the current neuropathological criteria (Braak and Braak 1991, 1999; Braak et al, 2003, 2006). Cases with mixed pathology (including vascular lesions) were excluded from this study. The brains used as control belonged to individuals without neurological manifestations and without injury in the neurological study. The medical records were reexamined for each case, and cases with pathology related to AD (stages I-IV) were reevaluated through phone calls or interviews with relatives, asking if they had evidence of any neurological or cognitive impairment. Only cases meeting these criteria were considered in this work. All cases analyzed summarized in Table 7.

The average post-mortem interval samples entorhinal cortex was 4.98±1.57 hours in controls, 7.51±5.13 hours in stages I-II, and 5.70 t 2.85 hours stage III-IV; for samples of the substantia nigra intervals were 5.59±2.46 hours and 9.23 in controls ±7.07 hours in the case of PD.

Murine Brain Samples

Transgenic mice APP/PS1 and wild strain were obtained from Jackson Laboratory (USA). The transgenic model expresses a murine/human chimera APP (Mo/HuAPP695swe: Swedish mutation APP) molecule and the human variant of presenilin 1 (PS1-DE9), both expression in neurons of the nervous system product. The animals were housed in standard conditions with light and dark cycles of 12 hours, with unlimited access to food and water. Stabling was conducted following the ethical guidelines (European Communities Council Directive 86/609/EEC) approved by the local ethics committee.

Total DNA Extraction

Total DNA was isolated human samples of the entorhinal cortex and substantia nigra (Table 7) using the DNeasy Blood and Tissue Kit (Qiagen, Madrid, Spain) following the manufacturer's instructions. Total DNA samples murine was obtained from the frontal cortex using the same procedure.

Bisulfite Treatment

Three hundred nanograms of DNA were treated using bisulfite EZ DNA kit methylation Kit (Zymo Research, Ecogen, Barcelona, Spain) following the supplier's instructions. The bisulfite-treated DNA was resuspended in 30 μl to reach a final concentration of 10 ng/ul. All samples were treated with bisulfite in parallel, using the same batch of reagent to avoid differences in the rate of bisulfite conversion between different commercial lots.

Design of the Primers for Amplicon FLX-Loop D and ND1

The primers for the FLX experiment were designed following the instructions techniques for FLX sequencer Roche "*Amplicon Fusion Primer Design Guidelines for GS FLX Titanium Series Lib-A Chemistry*". Melting Primers for amplicons containing a directional primer GS FLX Titanium primer A or primer B (including a key sequence (Key) Four bases) in Lot 5-oligonucleotide premium, plus a specific sequence for mold at 3-first final. Moreover, a MID sequence was added (multiplex Identifier) Between the primer A (or primer B) and the specific sequence for subsequent automated sample identification software after steps grouping/multiplexing and sequencing. The primers used contained the following components: Primer forward (Primer A-Key-MID-specific sequence mold), 5'-CGTATCGCCTCCCTCGCGCCA (SEQ ID NO: 33)-MID TCAG-specific template sequence 3'; Primer reverse (Primer B-Key-MID-specific template sequence): 5'CTATGCGCCTTGCCAGCCCGC (SEQ ID NO: 34)-MID TCAG-specific template sequence-3'. Specific template sequences for each of the amplicons: D-loop—direct, 5'-TAGGGGTTTTTTGATTATTATTTTT-3'(SEQ ID NO: 2) and D Loop—reverso, ACAAACATTCAATATTATTAT-TATATCCT 5'-3' (SEQ ID NO: 3); ND1—direct, 5'-ATGGTTAATTTTTTATTTTTTATTGTATTT-3' (SEQ ID NO: 4) and ND1—reverso, 5'-TAATTTAAAT-TAATACTCACCCTAATCAA-3'(SEQ ID NO: 5). The primers used in this study were designed to avoid CpG sites. Sequence MIDs specific for each patient shown in Table 8. amplified regions (D-Loop: 16386-256; ND1: 3313-3686) are based on nucleotide position map of human mtDNA (www.mitomap.org).

Preparation of Amplicon Library

The PCR amplicons for D-Loop and ND1 were performed according to the manual *Amplicon Library Preparation Method Manual* (*GS FLX Titanium Series*) Of Roche. PCRs for twenty nanograms total bisulfite-treated DNA were used. DNA amplification bisulfite treated are carried out in a reaction volume 25 ul. Each PCR reaction consisted of: 1× FastStart 10× Buffer #2 0.05 U/ul polymerase HiFi FastStart Polymerase (Roche), 200 nM of each dNTP, and 200 nM of each primer specific forward Y reverse. The primers were synthesized with a HPLC purification quality (Sigma-Aldrich, Madrid, Spain). Amplifications were performed in a thermocycler Applied Biosystems Verity® (Applied Biosystems, Madrid, Spain) using the following conditions: 94° C. for 3 min and then 36 cycles of 94° C. for 15 s, temperature annealing (61° C. ND1, and 62° C. D-Loop) for 45 s and 72° C. for 1 min, followed by a final extension step at 72° C. for 8 min and a final hold temperature at 4° C. two microliters of each PCR product were checked on an agarose gel stained with 1.5% SYBR® Safe DNA Gel Stain (Invitrogen, Madrid, Spain).

Purification of PCR

Purification of PCR products was performed using the kit Agencourt® AMPure® XP PCR Purification (Beckman Coulter, Madrid, Spain) following the instructions manual Roche *Amplicon Library Preparation Method Manual* (*GS FLX Titanium Series*).

Quantification of Amplicons and Sequencing Libraries FLX

Quantification and quality control amplicon libraries and the rest of FLX sequencing protocol was performed by the team of the Platform for Genomic Research Institute of Vall d'Hebron (VHIR, Barcelona, Spain).

Selection of Differentially Methylated Sites

Alignment and identification of CpG, CHG, and CHH sites and bisulfite conversion rates were performed using the HT Analyzer BIQ (Lutsik et al, 2011) software. Quality control of raw data and all statistical analysis.

They performed using the statistical language R and bioconductor software, http:///www.bioconductor.org.

The selection of differentially methylated sites was based on the calculation of Fisher's Exact test statistic Test, considering those sites differentially methylated with a p-value set using Benjamini and Hochberg method (1995) below 0.05. The □-value represented in Heatmaps graphs is the ratio of methylated sequences with respect to the overall sum of methylated and unmethylated sequences per site (Du et al, 2010, BMC Bioinformatics, 30; 11: 587), i.e. $\beta_{i,j}$=M/(M OR) Where M is the number of methylated sequences at the site (i) and MID (j), and U is the number of non-methylated at the site (i) and MID (j) sequences.

Figure 1B:
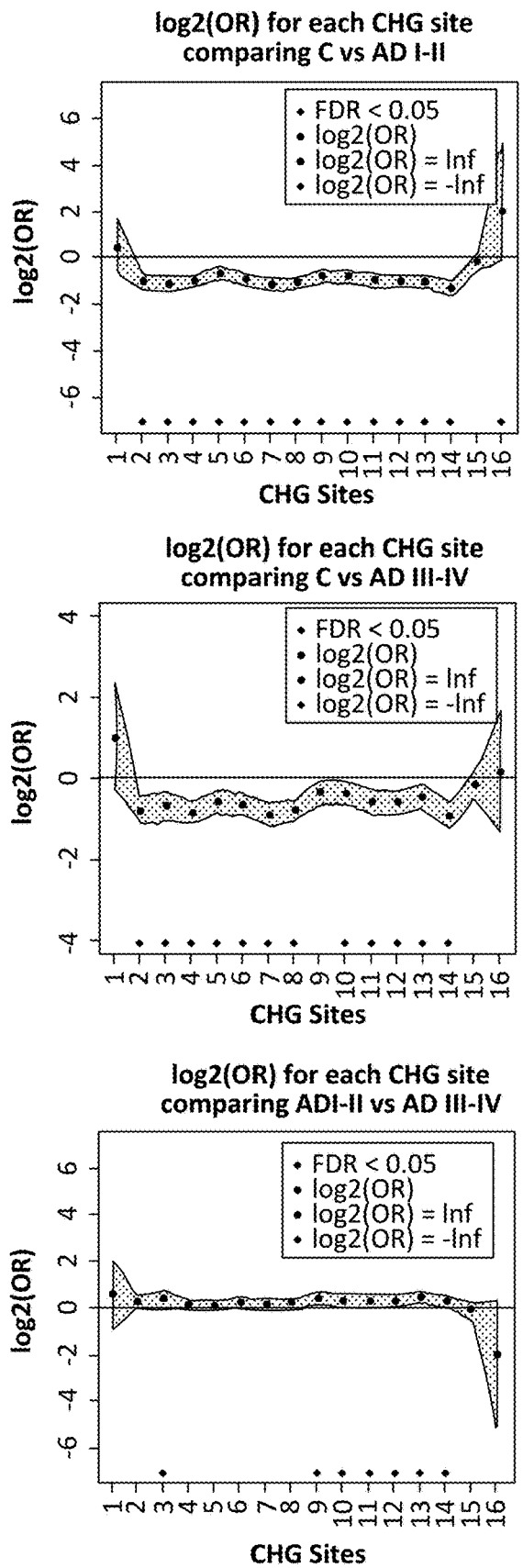
Figure 1C:
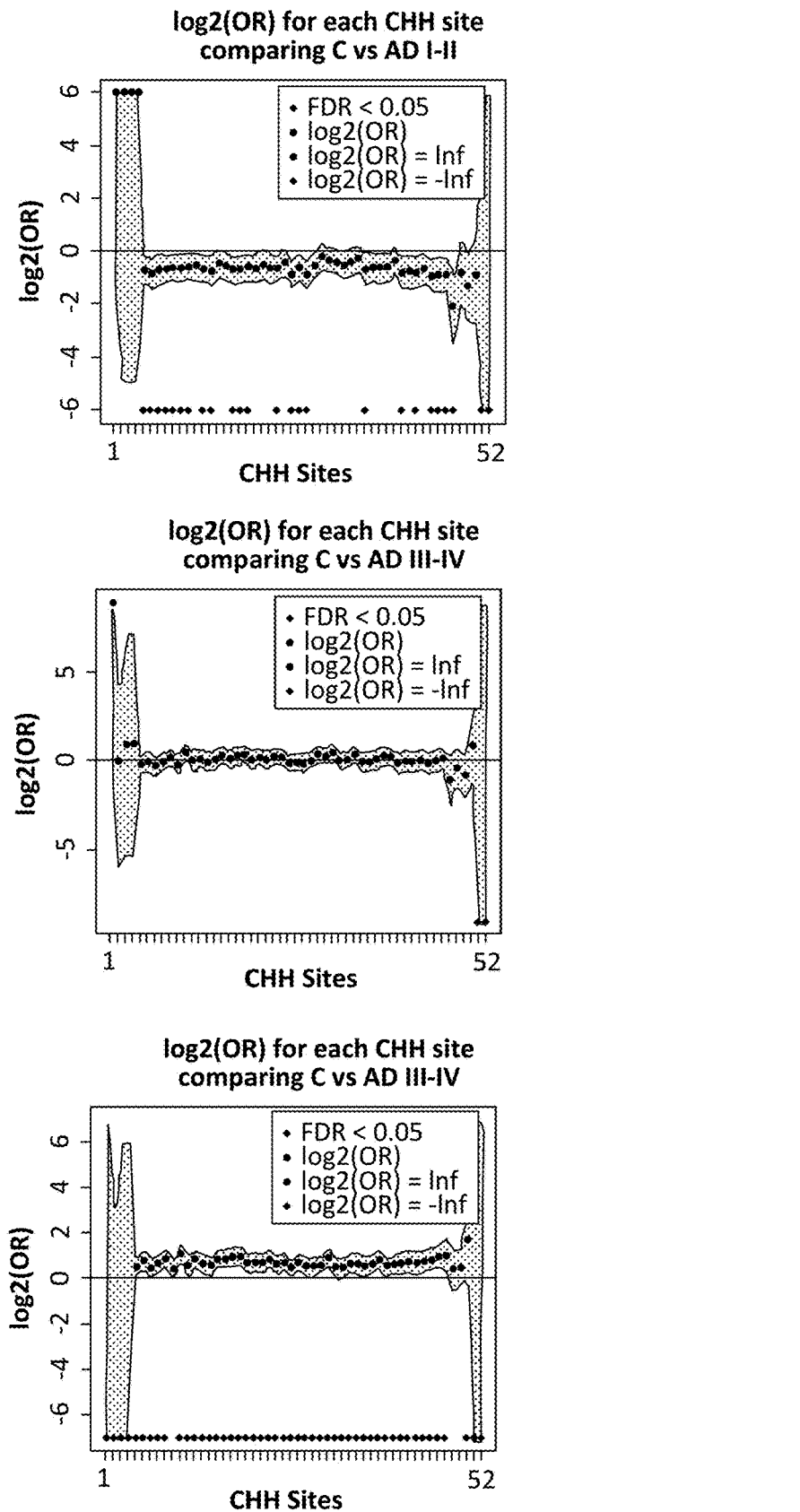

Example 1: DNA Methylation is Increased in the D-Loop Region and Reduced in the ND1 Gene in Cases with Early Stages of AD-Related Pathology An increase in methylation in CpG and non CpG sites (CHG and CHH) was observed in the D-loop region in cases with AD pathology related to stages I/II and III/IV of Braak (FIG. 1).

Figure 2A:
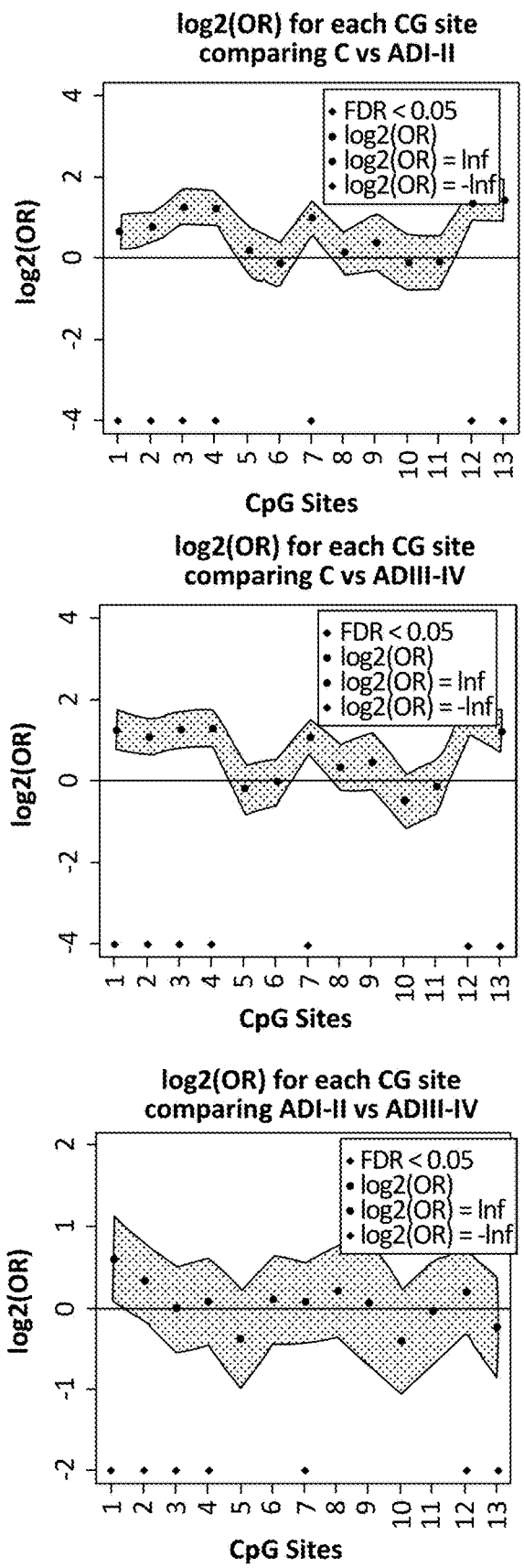
FIGS. 2A-2C: Graphics Log 2(OR) for CpG (A) CHG (B) and CHH (C) sites in the ND1 amplicon in the entorhinal cortex of AD pathology related cases. In Methylation sites from 5' to 3' are represented in the x-axis. The places marked with a diamond are differentially methylated sites of union of all the confidence intervals of 95%. C: control samples, AD: Alzheimer's disease.
Figure 2B:
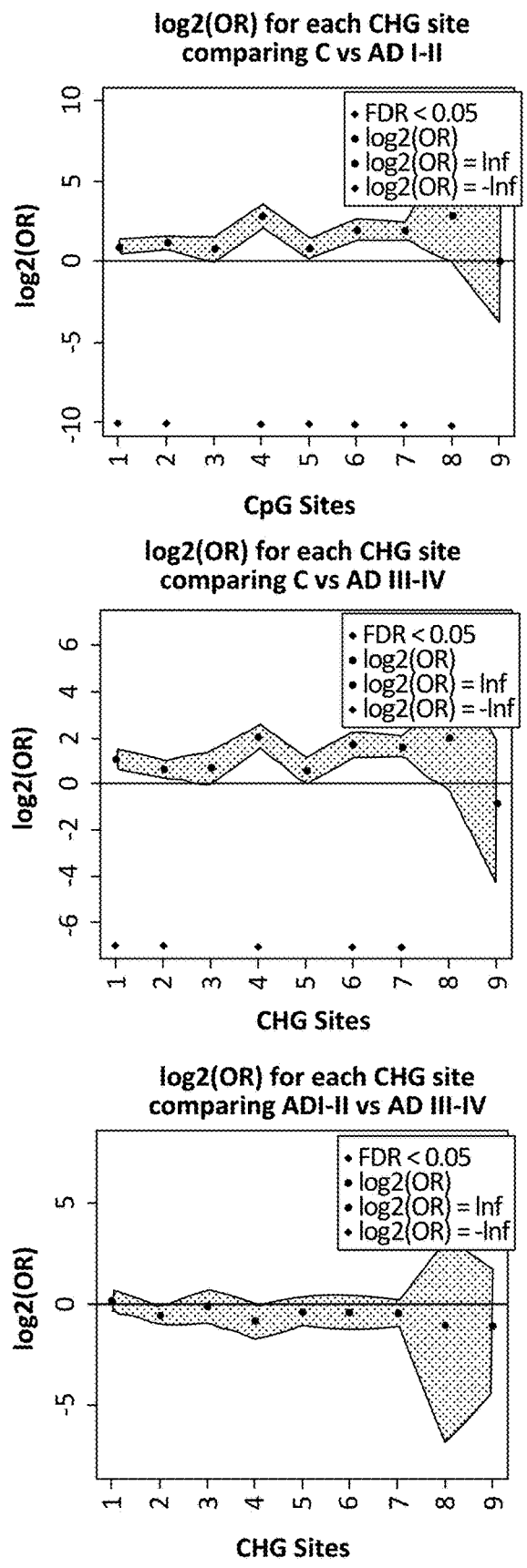
Figure 2C:
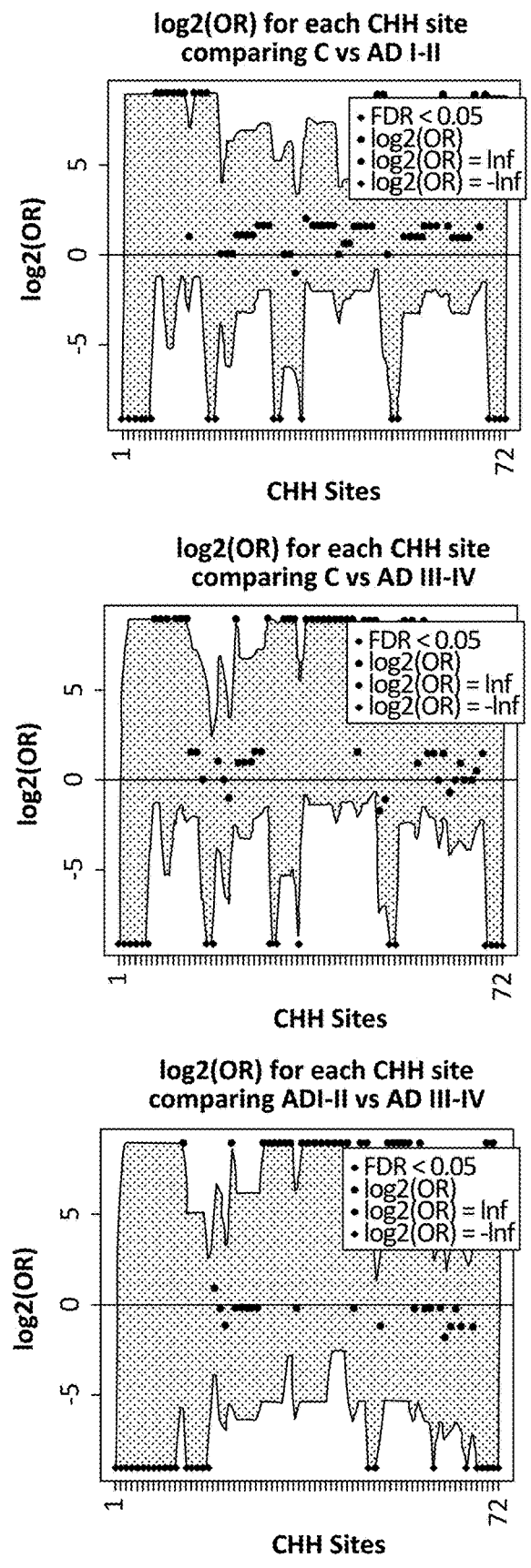

The degree of methylation was higher in cases of pathology related to AD with respect to the control samples, and higher stage I/II versus stage III/IV, as shown in log 2 graphics (OR) (FIG. 2). However, no differences in methylation of CHH sites between controls and cases with AD-related pathology at stages III/IV were found.

Figure 3:
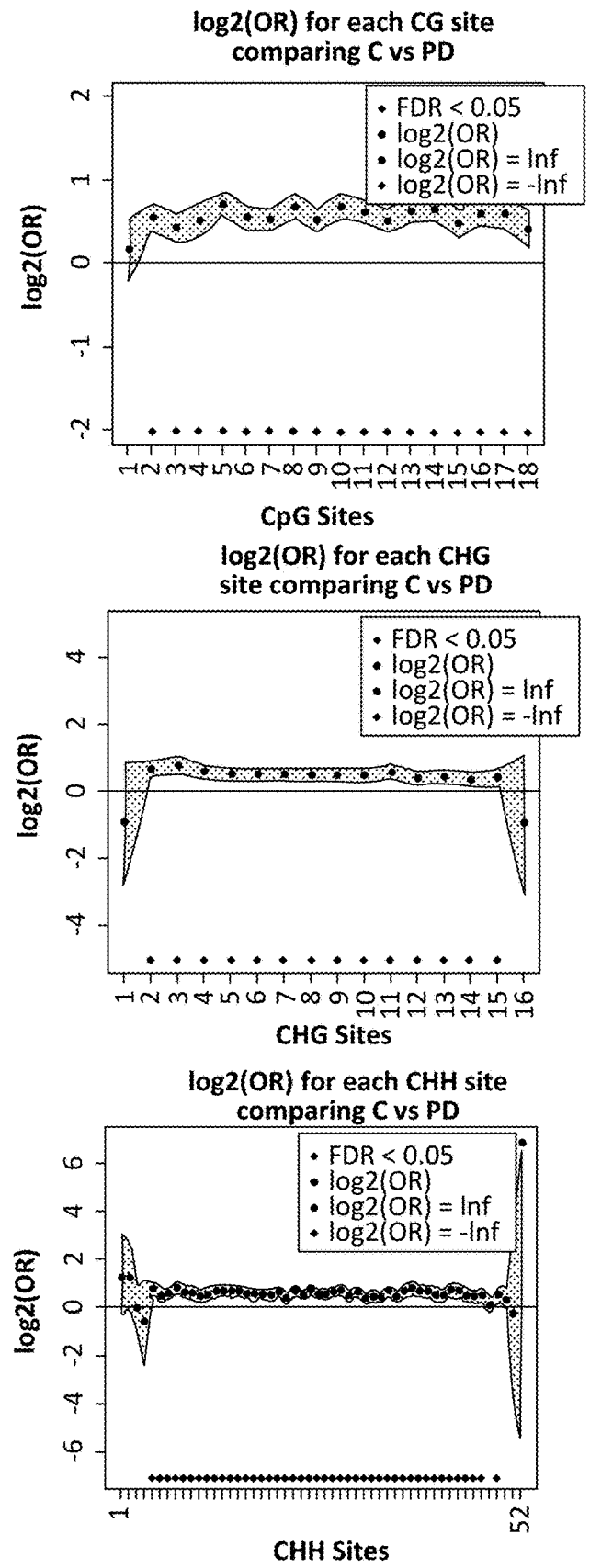
FIG. 3: Graphics Log 2 (OR) for CpG and non-CpG (CHG and CHH) sites in the amplicon D-loop in the substantia nigra in patients with PD. In the x-axis are Methylation sites from 5' to 3' are represented in the x-axis. The sites marked with a diamond are differentially methylated sites (FDR<0.05). Dots are estimated OR values, one for each site, and the band is the band of union of all the confidence intervals of 95%. C: control samples, PD: Parkinson's disease.

ND1 analysis revealed the presence of some less methylated CpG and CHG sites in cases with related AD pathology stage I/II and III/IV compared to control samples (log 2 [O]>0, FIG. 3). No differences were found for the CHH sites.

Example 2: DNA Methylation is Reduced in the D-Loop Region in the Substantia Nigra of PD Cases In contrast to what was observed in the entorhinal cortex in AD, the D-loop region showed a loss of methylation in almost all CpG and non CpG sites in the substantia nigra ub PD cases with respect to the control samples (FIG. 3). However, as with AD, the percentage of DNA methylation represents a small part of the total mitochondrial DNA.

Figure 4A:
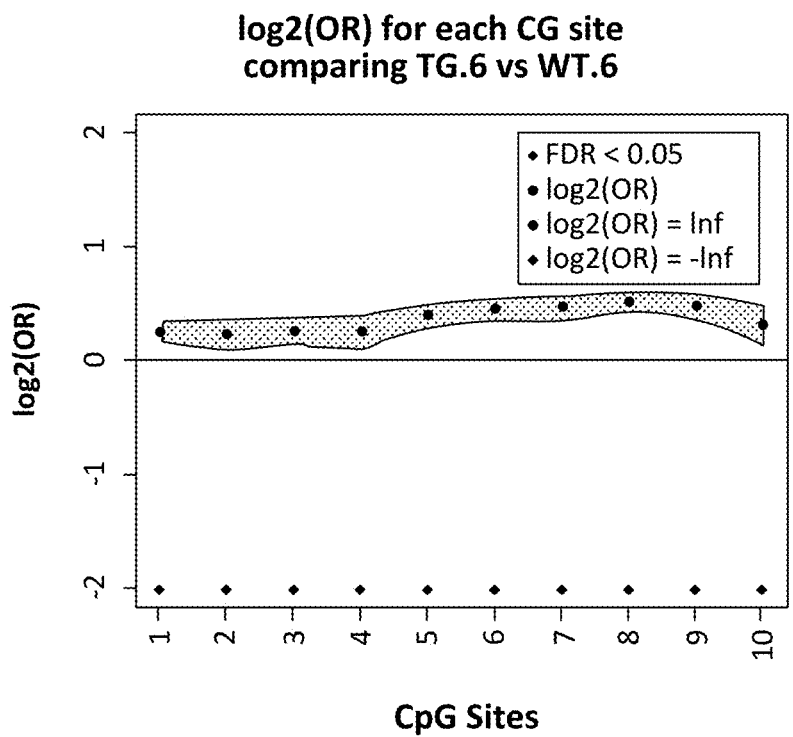
Figure 4B:
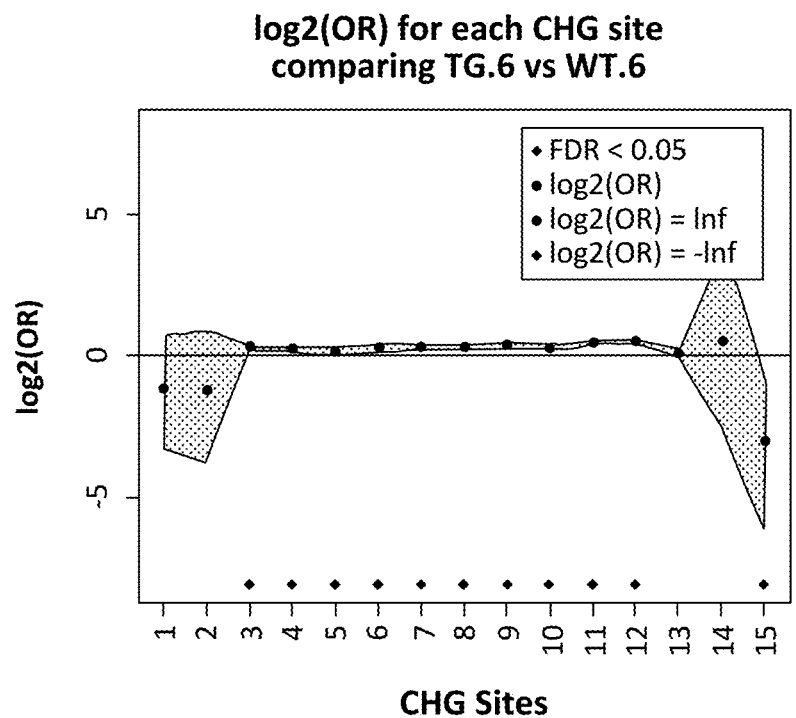

Example 3: DNA Methylation is Increased in the Region D-Loop in Murine Models of AD In this study, mice APP/PS1 (murine model of AD) six months of age (n=4) and control mice of the same age (n=4) were used. As can be seen in FIG. 4A, the CpG sites showed hypermethylation in samples obtained from pathology of mouse models with respect to the control samples. These results were also seen in CHG sites (see FIG. 4B).

To determine the methylation pattern as advance of AD, they employed mice APP/PS1 of three, six and twelve months. At three months, the APP/APS1 mice have a low degree of accumulation of neuritic plaques, which increases in APP/APS1 mice six months old. AD model mice six months of age show cognitive and memory failures. Finally, APP/APS1 animals of 12 months show similar symptoms to those observed in humans in advanced stages of AD.

Figure 5A:
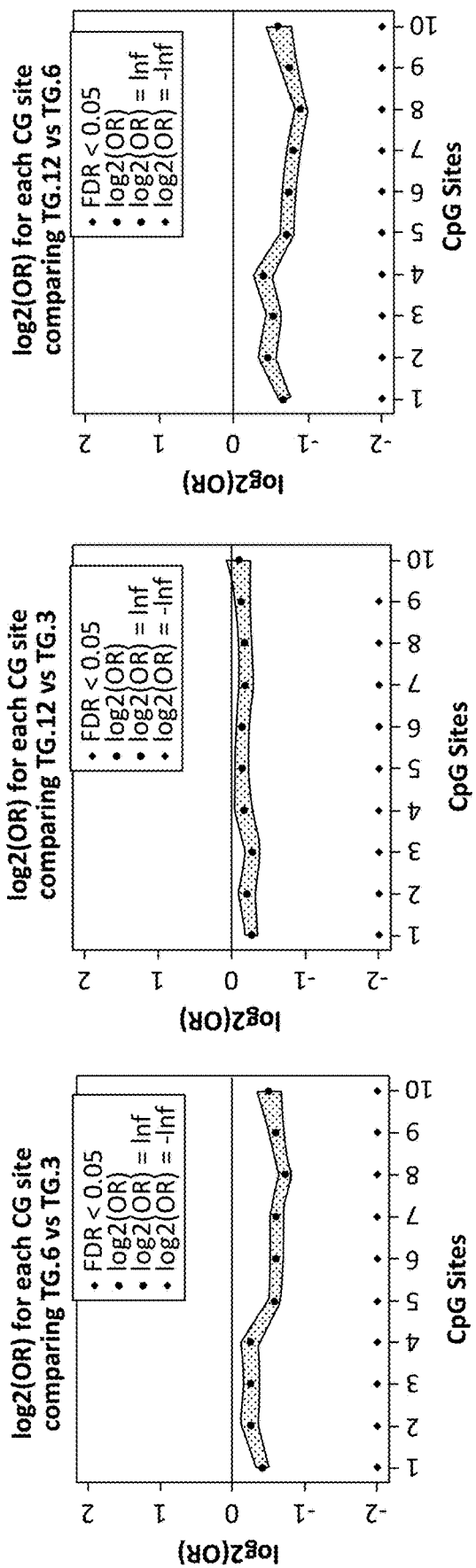
FIGS. 5A-5C: Graphics Log 2 (OR) for CG (A) CHG (B) and CHH (C) sites in the amplicon D-Loop in the frontal cortex of APP/PS1 of mice three, six and twelve months. Methylation sites sorted by 5' to 3' are represented in the x-axis. The sites marked with a diamond are differentially methylated sites (FDR<0.05). Dots are estimated OR values, one for each site, and the band is the band of union of all the confidence intervals of 95%. C: control samples, TG: Transgenic.
Figure 5B:
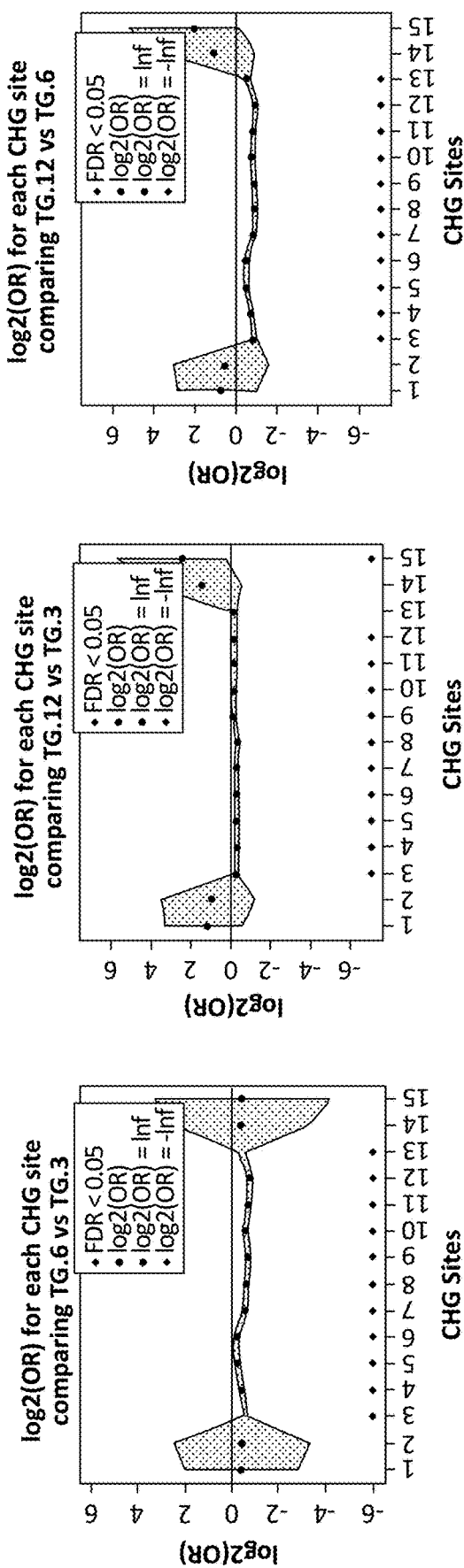
Figure 5C:
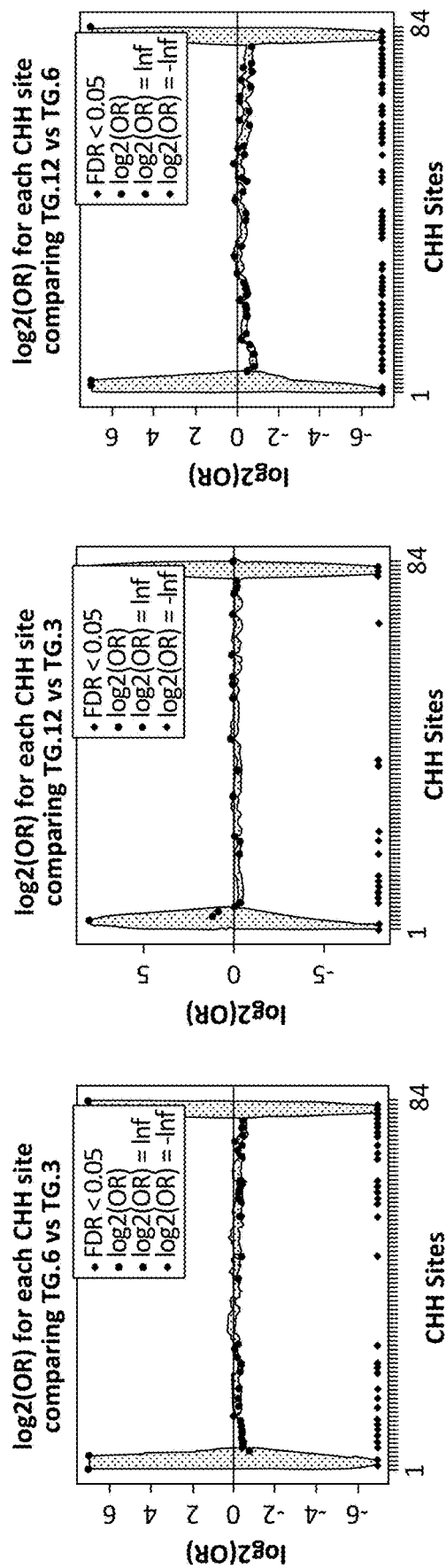

The analysis of the degree of methylation in the D-Loop region corroborated the pattern observed in samples of human brain tissue. As shown in FIG. 5, a tendency to hypomethylation of CpG sites CHG and CHH was observed in model mice in advanced stages of AD with respect to said CpG, CHG and CHH sites model mice in early stages of AD (FIGS. 5A, 5B and 5C).

Example 4: The Presence of the Polymorphic Position 16519 in Mitochondrial DNA is Associated with the Development of Alzheimers Disease The results shown in Table 9 show that the presence of the polymorphism T16519C is associated with Alzheimer's disease. Said results were obtained by conventional sequencing and using a chi-square test.

TABLE 9

Presence of polymorphism in samples obtained from individuals controls and individuals with Alzheimer's disease (AD) at different stages (Roman numerals).

| Type of sample Number of Samples analyzed) | presence of polymorphism T16519C (%) | p-value |
|---|---|---|
| Controls (n = 46) | 56.5 | — |
| AD I/II (n = 47) | 76.6 | 0.02 |

TABLE 9-continued

Presence of polymorphism in samples obtained from individuals controls and individuals with Alzheimer's disease (AD) at different stages (Roman numerals).

| Type of sample Number of Samples analyzed) | presence of polymorphism T16519C (%) | p-value |
|---|---|---|
| AD III/IV (n = 47) | 74.4 | 0.03 |
| AD V/VI (n = 46) | 76.1 | 0.02 |

The presence of heteroplasmy was observed in some cases and was performed again genotyping samples by using PCR-RFLP. The presence of the C allele creates a restriction site for the restriction enzyme HaeIII. The amplification of the sequence shown in SEQ ID NO: 30 was carried out using oligonucleotides SEQ ID NO: 31 and SEQ ID NO: 32. The following band patterns depending on the genotype were obtained:

Genotype T: 183 bp, 318 bp

Genotype C: 61 bp, 183 bp, 257

Heteroplasmia: 61 bp, 183 bp, 257 bp, 319 bp.

The invention claimed is:

1. A method for delaying progression of Alzheimer's disease in a subject comprising delivering a treatment for delaying the progression of Alzheimer's disease to the subject, wherein said treatment is administration of a pharmaceutical agent selected from the group consisting of a cholinesterase inhibitor, a cholinesterase antagonist and N-methyl-D-aspartate (NMDA), wherein the subject has been identified as having hypermethylation in the D-loop region of mitochondrial DNA by a method of detecting a hypermethylation in the D-loop region of mitochondrial DNA comprising:
  (a) obtaining a mitochondrial DNA sample comprising SEQ ID NO: 1 from the subject; and
  (b) detecting hypermethylation at CHH sites in the D-loop region of the mitochondrial DNA, wherein the CHH sites are selected from the group consisting of CHH sites at positions 16419, 16425, 16429, 16439, 16442, 16446, 16451, 16458, 16465, 16478, 16498, 16511, 16520, 16527, 16536, 16540, 16546, 16549, 4, 11, 113, 144, 147, 150, 164, 167, 190, of SEQ ID NO: 1;
  wherein hypermethylation at the CHH sites at positions 16419, 16425, 16429, 16439, 16442, 16446, 16451, 16458, 16465, 16478, 16498, 16511, 16520, 16527, 16536, 16540, 16546, 16549, 4, 11, 113, 144, 147, 150, 164, 167, and 190 of SEQ ID NO: 1 in the D-loop region of the mitochondrial DNA from the subject is compared to methylation of CHH sites at positions 16419, 16425, 16429, 16439, 16442, 16446, 16451, 16458, 16465, 16478, 16498, 16511, 16520, 16527, 16536, 16540, 16546, 16549, 4, 11, 113, 144, 147, 150, 164, 167, and 190 of SEQ ID NO: 1 in the D-loop region of mitochondrial DNA from a reference sample obtained from a subject not suffering from Alzheimer's disease, and the detecting is conducted by a technique selected from the group consisting of methylation specific PCR, bisulfite sequencing, techniques based on restriction-digestion, pyrosequencing, assay ChIP-on-chip, differential conversion, differential restriction, and differential weight of site(s) methylated.

2. The method according to claim 1, wherein said detecting hypermethylation at CHH sites in the D-loop of the mitochondrial DNA, comprises detecting hypermethylation at positions 16419, 16425, 16429, 16439, 16442, 16446, 16451, 16458, 16465, 16478, 16498, 16511, 16520, 16527, 16536, 16540, 16546, 16549, 4, 11, 113, 144, 147, 150, 164, 167, and 190 of SEQ ID NO: 1.

3. The method of claim 1, wherein said detecting is conducted by pyrosequencing.

4. The method according to claim 1, wherein the mitochondrial DNA obtained from the subject is contained in a biofluid or a biopsy of a solid tissue.

5. The method according to claim 4, wherein said biofluid is a peripheral blood or a cerebrospinal fluid.

6. The method according to claim 1, wherein the treatment comprises administration of a cholinesterase inhibitor selected from the group consisting of donepezil hydrochloride (Arecept), rivastigmine (Exelon), and galantamina (Reminyl).

7. The method according to claim 1, wherein step (b) comprises bisulfite sequencing or pyrosequencing at least 11,672 reads per D-loop of the mitochondrial DNA.

8. The method according to claim 1, wherein the subject has been diagnosed with Alzheimer's disease in stage I-II.

9. The method according to claim 1, wherein the subject has been further identified as having hypermethylation at CpG sites in the D-loop region of mitochondrial DNA by a method of detecting hypermethylation at CpG sites in the D-loop region of the mitochondrial DNA comprising: detecting hypermethylation at CpG sites in the D-loop region of mitochondrial DNA from the mitochondrial DNA sample comprising SEQ ID NO:1 obtained from the subject, wherein the CpG sites are selected from CpG sites at positions 16427, 16449, 16454, 16495, 16542, 16565, 61, 162, and 170 of SEQ ID NO: 1; wherein hypermethylation at the CpG sites at positions 16427, 16449, 16454, 16495, 16542, 16565, 61, 162, and 170 of SEQ ID NO: 1 in the D-loop region of the mitochondrial DNA from the subject is compared to methylation of CpG sites at positions 16427, 16449, 16454, 16495, 16542, 16565, 61, 162, and 170 of SEQ ID NO: 1 in the D-loop region of mitochondrial DNA from a reference sample obtained from a subject not suffering from Alzheimer's disease.

10. The method according to claim 1, wherein the subject has been further identified as having hypermethylation at CHG sites in the D-loop region of mitochondrial DNA by a method of detecting hypermethylation at CHG sites in the D-loop region of the mitochondrial DNA comprising: detecting hypermethylation at CHG sites in the D-loop region of mitochondrial DNA from the mitochondrial DNA sample comprising SEQ ID NO:1 obtained from the subject, wherein the CHG sites are selected from CHG sites at positions 16426, 16453, 16459, 16466, 16479, 16514, 6, 33, 64, 104, 122, 128, 141, and 253 of SEQ ID NO: 1, wherein hypermethylation at the CHG sites at positions 16426, 16453, 16459, 16466, 16479, 16514, 6, 33, 64, 104, 122, 128, 141, and 253 of SEQ ID NO: 1 in the D-loop region of the mitochondrial DNA from the subject is compared to methylation of CHG sites at positions 16426, 16453, 16459, 16466, 16479, 16514, 6, 33, 64, 104, 122, 128, 141, and 253 of SEQ ID NO: 1 in the D-loop region of mitochondrial DNA from a reference sample obtained from a subject not suffering from Alzheimer's disease.

11. The method according to claim 1, wherein the subject has been further identified as having hypomethylation at CpG sites in the ND1 gene of mitochondrial DNA by a method of detecting hypomethylation at CpG sites in the ND 1 gene of the mitochondrial DNA comprising: detecting hypomethylation at CpG sites in the ND 1 gene of mitochondrial DNA from the mitochondrial DNA sample comprising SEQ ID NO:1 obtained from the subject, wherein the CpG sites are selected from CpG sites at positions 3351, 3375, 3379, 3406, 3453, 3549, and 3642 of SEQ ID NO: 1, wherein hypomethylation at the CpG sites at positions 3351, 3375, 3379, 3406, 3453, 3549, and 3642 of SEQ ID NO: 1 in the ND1 gene of the mitochondrial DNA from the subject is compared to methylation of CpG sites at positions 3351, 3375, 3379, 3406, 3453, 3549, and 3642 of SEQ ID NO: 1 in the ND1 gene of mitochondrial DNA from a reference sample obtained from a subject not suffering from Alzheimer's disease.

12. The method according to claim 1, wherein the subject has been further identified as having hypomethylation at CHG sites in the ND1 gene of mitochondrial DNA by a method of detecting hypomethylation at CHG sites in the ND 1 gene of the mitochondrial DNA comprising: detecting hypomethylation at CHG sites in the ND 1 gene of mitochondrial DNA from the mitochondrial DNA sample comprising SEQ ID NO:1 obtained from the subject, wherein the CHG sites are selected from CHG sites at positions 3374, 3435, 3524, 3529, 3589, 3641, and 3657 of SEQ ID NO: 1, wherein hypomethylation at the CHG sites at positions 3374, 3435, 3524, 3529, 3589, 3641, and 3657 of SEQ ID NO: 1 in the ND1 gene of the mitochondrial DNA from the subject is compared to methylation of CHG sites at positions 3374, 3435, 3524, 3529, 3589, 3641, and 3657 of SEQ ID NO: 1 in the ND1 gene of mitochondrial DNA from a reference sample obtained from a subject not suffering from Alzheimer's disease.

* * * * *

SEQUENCE LISTING

<160> NUMBER OF SEQ ID NOS: 34

<210> SEQ ID NO 1
<211> LENGTH: 16569
<212> TYPE: DNA
<213> ORGANISM: Homo sapiens
<220> FEATURE:
<221> NAME/KEY: misc_feature
<222> LOCATION: (3107)..(3107)
<223> OTHER INFORMATION: n is a, c, g, or t

<400> SEQUENCE: 1

```
gatcacaggt ctatcaccct attaaccact cacgggagct ctccatgcat ttggtatttt      60
cgtctggggg gtatgcacgc gatagcattg cgagacgctg gagccggagc accctatgtc     120
gcagtatctg tctttgattc ctgcctcatc ctattattta tcgcacctac gttcaatatt     180
acaggcgaac atacttacta aagtgtgtta attaattaat gcttgtagga cataataata     240
acaattgaat gtctgcacag ccactttcca cacagacatc ataacaaaaa atttccacca     300
aacccccccct cccccgcttc tggccacagc acttaaacac atctctgcca aaccccaaaa     360
acaaagaacc ctaacaccag cctaaccaga tttcaaattt tatcttttgg cggtatgcac     420
ttttaacagt caccccccaa ctaacacatt attttcccct cccactccca tactactaat     480
ctcatcaata caaccccgc ccatcctacc cagcacacac acaccgctgc taacccata      540
ccccgaacca accaaacccc aaagacaccc cccacagttt atgtagctta cctcctcaaa     600
gcaatacact gaaaatgttt agacgggctc acatcacccc ataaacaaat aggtttggtc     660
ctagccttc tattagctct tagtaagatt acacatgcaa gcatcccgt tccagtgagt     720
tcaccctcta aatcaccacg atcaaaagga acaagcatca agcacgcagc aatgcagctc     780
aaaacgctta gcctagccac accccacgg gaaacagcag tgattaacct ttagcaataa     840
acgaaagttt aactaagcta tactaacccc agggttggtc aatttcgtgc cagccaccgc     900
ggtcacacga ttaacccaag tcaatagaag ccggcgtaaa gagtgtttta gatcaccccc     960
tccccaataa agctaaaact cacctgagtt gtaaaaaact ccagttgaca caaaatagac    1020
tacgaaagtg gctttaacat atctgaacac acaatagcta agacccaaac tgggattaga    1080
tacccacta tgcttagccc taaacctcaa cagttaaatc aacaaaactg ctcgccagaa    1140
cactacgagc cacagcttaa aactcaaagg acctggcggt gcttcatatc cctctagagg    1200
agcctgttct gtaatcgata acccccgatc aacctcacca cctcttgctc agcctatata    1260
ccgccatctt cagcaaaccc tgatgaaggc tacaaagtaa gcgcaagtac ccacgtaaag    1320
acgttaggtc aaggtgtagc ccatgaggtg gcaagaaatg ggctacattt tctacccag    1380
aaaactacga tagcccttat gaaacttaag ggtcgaaggt ggatttagca gtaaactaag    1440
agtagagtgc ttagttgaac agggccctga agcgcgtaca caccgcccgt cacccctcctc   1500
```

```
aagtatactt caaaggacat ttaactaaaa cccctacgca tttatataga ggagacaagt    1560
cgtaacatgg taagtgtact ggaaagtgca cttggacgaa ccagagtgta gcttaacaca    1620
aagcacccaa cttacactta ggagatttca acttaacttg accgctctga gctaaaccta    1680
gccccaaacc cactccacct tactaccaga caaccttagc caaaccattt acccaaataa    1740
agtataggcg atagaaattg aaacctggcg caatagatat agtaccgcaa gggaaagatg    1800
aaaaattata accaagcata atatagcaag gactaacccc tataccttct gcataatgaa    1860
ttaactagaa ataactttgc aaggagagcc aaagctaaga cccccgaaac cagacgagct    1920
acctaagaac agctaaaaga gcacacccgt ctatgtagca aaatagtggg aagatttata    1980
ggtagaggcg acaaacctac cgagcctggt gatagctggt tgtccaagat agaatcttag    2040
ttcaactttt aatttgccca cagaaccctc taaatcccct tgtaaattta actgttagtc    2100
caaagaggaa cagctctttg gacactagga aaaaccttg tagagagagt aaaaaattta    2160
acacccatag taggcctaaa agcagccacc aattaagaaa gcgttcaagc tcaacaccca    2220
ctacctaaaa aatcccaaac atataactga actcctcaca cccaattgga ccaatctatc    2280
accctataga agaactaatg ttagtataag taacatgaaa acattctcct ccgcataagc    2340
ctgcgtcaga ttaaaacact gaactgacaa ttaacagccc aatatctaca atcaaccaac    2400
aagtcattat taccctcact gtcaacccaa cacaggcatg ctcataagga aaggttaaaa    2460
aaagtaaaag gaactcggca aatcttaccc cgcctgttta ccaaaaacat cacctctagc    2520
atcaccagta ttagaggcac cgcctgccca gtgacacatg tttaacggcc gcggtaccct    2580
aaccgtgcaa aggtagcata atcacttgtt ccttaaatag ggacctgtat gaatggctcc    2640
acgagggttc agctgtctct tactttaac cagtgaaatt gacctgcccg tgaagaggcg    2700
ggcataacac agcaagacga gaagaccct atggagcttta atttattaat gcaaacagta    2760
cctaacaaac ccacaggtcc taaactacca aacctgcatt aaaaatttcg gttggggcga    2820
cctcggagca gaacccaacc tccgagcagt acatgctaag acttcaccag tcaaagcgaa    2880
ctactatact caattgatcc aataacttga ccaacggaac aagttaccct agggataaca    2940
gcgcaatcct attctagagt ccatatcaac aatagggttt cgacctcga tgttggatca    3000 ggacatcccg atggtgcagc cgctattaaa ggttcgtttg ttcaacgatt aaagtcctac    3060
gtgatctgag ttcagaccgg agtaatccag gtcggtttct atctacnttc aaattcctcc    3120
ctgtacgaaa ggacaagaga ataaggcct acttcacaaa gcgccttccc ccgtaaatga    3180
tatcatctca acttagtatt atacccacac ccacccaaga cagggtttg ttaagatggc    3240 agagcccggt aatcgcataa aacttaaaac tttacagtca gaggttcaat tcctcttctt    3300
aacaacatac ccatggccaa cctcctactc tcattgtac ccattctaat cgcaatggca    3360
ttcctaatgc ttaccgaacg aaaaattcta ggctatatac aactacgcaa aggccccaac    3420
gttgtaggcc cctacgggct actacaaccc ttcgctgacg ccataaaact cttcaccaaa    3480
gagcccctaa aacccgccac atctaccatc accctctaca tcaccgcccc gaccttagct    3540
ctcaccatcg ctcttctact atgaaccccc ctccccatac caacccct ggtcaacctc    3600 aacctaggcc tcctatttat tctagccacc tctagcctag ccgtttactc aatcctctga    3660
tcagggtgag catcaaactc aaactacgcc ctgatcggcg cactgcgagc agtagcccaa    3720
acaatctcat atgaagtcac cctagccatc attctactat caacattact aataagtggc    3780
tcctttaacc tctccaccct tatcacaaca caagaacacc tctgattact cctgccatca    3840
```

```
tgacccttgg ccataatatg atttatctcc acactagcag agaccaaccg aaccccttc    3900 gaccttgccg aagggagtc cgaactagtc tcaggcttca acatcgaata cgccgcaggc    3960
cccttcgccc tattcttcat agccgaatac acaaacatta ttataataaa caccctcacc    4020
actacaatct tcctaggaac aacatatgac gcactctccc ctgaactcta cacaacatat    4080
tttgtcacca agaccctact tctaacctcc ctgttcttat gaattcgaac agcataccc    4140 cgattccgct acgaccaact catacacctc ctatgaaaaa acttcctacc actcacccta    4200
gcattactta tatgatatgt ctccataccc attacaatct ccagcattcc ccctcaaacc    4260
taagaaatat gtctgataaa agagttactt tgatagagta aataatagga gcttaaaccc    4320
ccttatttct aggactatga gaatcgaacc catccctgag aatccaaaat tctccgtgcc    4380
acctatcaca ccccatccta agtaaggtc agctaaataa gctatcgggc ccatacccg     4440 aaaatgttgg ttatacccctt cccgtactaa ttaatcccct ggcccaaccc gtcatctact    4500
ctaccatctt tgcaggcaca ctcatcacag cgctaagctc gcactgattt tttacctgag    4560
taggcctaga aataaacatg ctagctttta ttccagttct aaccaaaaaa ataaaccctc    4620
gttccacaga agctgccatc aagtatttcc tcacgcaagc aaccgcatcc ataatccttc    4680
taatagctat cctcttcaac aatatactct ccggacaatg aaccataacc aatactacca    4740
atcaatactc atcattaata atcataatag ctatagcaat aaaactagga atagccccct    4800
ttcacttctg agtcccagag gttacccaag gcaccctct gacatccggc ctgcttcttc    4860
tcacatgaca aaaactagcc cccatctcaa tcatatacca aatctctccc tcactaaacg    4920
taagccttct cctcactctc tcaatcttat ccatcatagc aggcagttga ggtggattaa    4980
accaaaccca gctacgcaaa atcttagcat actcctcaat tacccacata ggatgaataa    5040
tagcagttct accgtacaac cctaacataa ccattcttaa tttaactatt tatattatcc    5100
taactactac cgcattccta ctactcaact aaaactccag caccacgacc ctactactat    5160
ctcgcacctg aaacaagcta acatgactaa caccccttaat tccatccacc ctcctctccc    5220
taggaggcct gcccccgcta accggctttt tgcccaaatg ggccattatc gaagaattca    5280
caaaaaacaa tagcctcatc atccccacca tcatagccac catcaccctc cttaacctct    5340
acttctacct acgcctaatc tactccacct caatcacact actccccata tctaacaacg    5400
taaaaataaa atgacagttt gaacatacaa aacccacccc attcctcccc acactcatcg    5460
cccttaccac gctactccta cctatctccc cttttatact aataatctta tagaaattta    5520
ggttaaatac agaccaagag ccttcaaagc cctcagtaag ttgcaatact taatttctgt    5580
aacagctaag gactgcaaaa ccccactctg catcaactga acgcaaatca gccactttaa    5640
ttaagctaag cccttactag accaatggga cttaaaccca caaacactta gttaacagct    5700 aagcaccta atcaactggc ttcaatctac ttctcccgcc gccgggaaaa aaggcgggag    5760
aagccccggc aggtttgaag ctgcttcttc gaatttgcaa ttcaatatga aaatcacctc    5820
ggagctggta aaagaggcc taaccccctgt ctttagattt acagtccaat gcttcactca    5880 gccatttttac ctcacccca ctgatgttcg ccgaccgttg actattctct acaaaccaca    5940
aagacattgg aacactatac ctattattcg gcgcatgagc tggagtccta ggcacagctc    6000
taagcctcct tattcgagcc gagctgggcc agccaggcaa ccttctaggt aacgaccaca    6060
tctacaacgt tatcgtcaca gcccatgcat ttgtaataat cttcttcata gtaatacccca   6120 tcataatcgg aggctttggc aactgactag ttcccctaat aatcggtgcc cccgatatgg    6180
cgtttccccg cataaacaac ataagcttct gactcttacc tccctctctc ctactcctgc    6240
```

```
tcgcatctgc tatagtggag gccggagcag gaacaggttg aacagtctac cctcccttag   6300
cagggaacta ctcccaccct ggagcctccg tagacctaac catcttctcc ttacacctag   6360
caggtgtctc ctctatctta ggggccatca atttcatcac aacaattatc aatataaaac   6420
cccctgccat aacccaatac caaacgcccc tcttcgtctg atccgtccta atcacagcag   6480
tcctacttct cctatctctc ccagtcctag ctgctggcat cactatacta ctaacagacc   6540
gcaacctcaa caccaccttc ttcgaccccg ccggaggagg agaccccatt ctataccaac   6600
acctattctg attttcggt caccctgaag tttatattct tatcctacca ggcttcggaa   6660
taatctccca tattgtaact tactactccg gaaaaaaaga accatttgga tacataggta   6720
tggtctgagc tatgatatca attggcttcc tagggtttat cgtgtgagca caccatatat   6780
ttacagtagg aatagacgta gacacacgag catatttcac ctccgctacc ataatcatcg   6840
ctatccccac cggcgtcaaa gtatttagct gactcgccac actccacgga agcaatatga   6900
aatgatctgc tgcagtgctc tgagccctag gattcatctt tcttttcacc gtaggtggcc   6960
tgactggcat tgtattagca aactcatcac tagacatcgt actacacgac acgtactacg   7020
ttgtagccca cttccactat gtcctatcaa taggagctgt atttgccatc ataggaggct   7080
tcattcactg atttccccta ttctcaggct acaccctaga ccaaacctac gccaaaatcc   7140
atttcactat catattcatc ggcgtaaatc taactttctt cccacaacac tttctcggcc   7200
tatccggaat gccccgacgt tactcggact accccgatgc atacaccaca tgaaacatcc   7260
tatcatctgt aggctcattc atttctctaa cagcagtaat attaataatt ttcatgattt   7320
gagaagcctt cgcttcgaag cgaaaagtcc taatagtaga agaaccctcc ataaacctgg   7380
agtgactata tggatgcccc ccaccctacc acacattcga agaacccgta tacataaaat   7440
ctagacaaaa aaggaaggaa tcgaaccccc caaagctggt ttcaagccaa ccccatggcc   7500
tccatgactt tttcaaaaag gtattagaaa aaccatttca taactttgtc aaagttaaat   7560
tataggctaa atcctatata tcttaatggc acatgcagcg caagtaggtc tacaagacgc   7620
tacttcccct atcatagaag agcttatcac ctttcatgat cacgccctca taatcatttt   7680
ccttatctgc ttcctagtcc tgtatgccct tttcctaaca ctcacaacaa aactaactaa   7740
tactaacatc tcagacgctc aggaaataga aaccgtctga actatcctgc ccgccatcat   7800
cctagtcctc atcgccctcc catccctacg catcctttac ataacagacg aggtcaacga   7860
tccctccctt accatcaaat caattggcca ccaatggtac tgaacctacg agtacaccga   7920
ctacggcgga ctaatcttca actcctacat acttccccca ttattcctag aaccaggcga   7980
cctgcgactc cttgacgttg acaatcgagt agtactcccg attgaagccc ccattcgtat   8040
aataattaca tcacaagacg tcttgcactc atgagctgtc cccacattag cttaaaaac    8100 agatgcaatt cccggacgtc taaaccaaac cactttcacc gctacacgac cggggggtata   8160 ctacggtcaa tgctctgaaa tctgtgggagc aaaccacagt ttcatgccca tcgtcctaga   8220
attaattccc ctaaaaatct ttgaaatagg gcccgtattt accctatagc accccctcta   8280 cccctctag agcccactgt aaagctaact tagcattaac cttttaagtt aaagattaag   8340
agaaccaaca cctctttaca gtgaaatgcc ccaactaaat actaccgtat ggcccaccat   8400
aattaccccc atactcctta cactattcct catcacccaa ctaaaaatat aaacacaaa    8460 ctaccaccta cctccctcac caaagcccat aaaaataaaa aattataaca aaccctgaga   8520
accaaaatga acgaaaatct gttcgcttca ttcattgccc ccacaatcct aggcctaccc   8580
```

```
gccgcagtac tgatcattct atttcccsct ctattgatcc ccacctccaa atatctcatc   8640
aacaaccgac taatcaccac ccaacaatga ctaatcaaac taacctcaaa acaaatgata   8700
accatacaca acactaaagg acgaacctga tctcttatac tagtatcctt aatcatttt    8760 attgccacaa ctaacctcct cggactcctg cctcactcat ttacaccaac cacccaacta   8820
tctataaacc tagccatggc catcccctta tgagcgggca cagtgattat aggctttcgc   8880
tctaagatta aaaatgccct agcccacttc ttaccacaag gcacacctac acccctttatc  8940 cccatactag ttattatcga aaccatcagc ctactcattc aaccaatagc cctggccgta   9000
cgcctaaccg ctaacattac tgcaggccac ctactcatgc acctaattgg aagcgccacc   9060
ctagcaatat caaccattaa ccttccctct acacttatca tcttcacaat tctaattcta   9120
ctgactatcc tagaaatcgc tgtcgcctta atccaagcct acgttttcac acttctagta   9180
agcctctacc tgcacgacaa cacataatga cccaccaatc acatgcctat catatagtaa   9240
aacccagccc atgaccccta cagggggccc tctcagccct cctaatgacc tccggcctag   9300
ccatgtgatt tcacttccac tccataacgc tcctcatact aggcctacta accaacacac   9360
taaccatata ccaatgatgg cgcgatgtaa cacgagaaag cacataccaa ggccaccaca   9420
caccacctgt ccaaaaaggc cttcgatacg ggataatcct atttattacc tcagaagttt   9480
ttttcttcgc aggatttttc tgagccttt accactccag cctagcccct accccccaat    9540
taggagggca ctggccccca acaggcatca ccccgctaaa tcccctagaa gtcccactcc   9600
taaacacatc cgtattactc gcatcaggag tatcaatcac ctgagctcac catagtctaa   9660
tagaaaacaa ccgaaaccaa ataattcaag cactgcttat tacaattttta ctgggtctct   9720 attttaccct cctacaagcc tcagagtact tcgagtctcc cttcaccatt tccgacggca   9780
tctacggctc aacatttttt gtagccacag gcttccacgg acttcacgtc attattggct   9840
caactttcct cactatctgc ttcatccgcc aactaatatt tcactttaca tccaaacatc   9900
actttggctt cgaagccgcc gcctgatact ggcattttgt agatgtggtt tgactatttc   9960
tgtatgtctc catctattga tgagggtctt actctttag tataaatagt accgttaact   10020
tccaattaac tagttttgac aacattcaaa aagagtaat aaactcgcc ttaattttaa    10080 taatcaacac cctcctagcc ttactactaa taattattac attttgacta ccacaactca   10140
acggctacat agaaaaatcc accccttacg agtgcggctt cgaccctata tccccgccc   10200 gcgtcccttt ctccataaaa ttcttcttag tagctattac cttcttatta tttgatctag   10260
aaattgccct ccttttaccc ctaccatgag ccctacaaac aactaacctg ccactaatag   10320
ttatgtcatc cctcttatta atcatcatcc tagccctaag tctggcctat gagtgactac   10380
aaaaaggatt agactgaacc gaattggtat atagtttaaa caaaacgaat gatttcgact   10440
cattaaatta tgataatcat atttaccaaa tgcccctcat ttacataaat attatactag   10500
catttaccat ctcacttcta ggaatactag tatatcgctc acacctcata tcctccctac   10560
tatgcctaga aggaataata ctatcgctgt tcattatagc tactctcata accctcaaca   10620
cccactccct cttagccaat attgtgccta ttgccatact agtctttgcc gcctgcgaag   10680
cagcggtggg cctagcccta ctagtctcaa tctccaacac atatggccta gactacgtac   10740
ataacctaaa cctactccaa tgctaaaact aatcgtccca caattatat tactaccact   10800 gacatgactt tccaaaaaac acataatttg aatcaacaca accacccaca gcctaattat   10860
tagcatcatc cctctactat ttttaacca aatcaacaac aacctattta gctgttcccc   10920
aaccttttcc tccgaccccc taacaacccc cctcctaata ctaactacct gactcctacc   10980
```

```
cctcacaatc atggcaagcc aacgccactt atccagtgaa ccactatcac gaaaaaaact  11040
ctacctctct atactaatct ccctacaaat tccttaatt ataacattca cagccacaga  11100
actaatcata ttttatatct tcttcgaaac cacacttatc cccaccttgg ctatcatcac  11160
ccgatgaggc aaccagccag aacgcctgaa cgcaggcaca tacttcctat tctacaccct  11220
agtaggctcc cttcccctac tcatcgcact aatttacact cacaacaccc taggctcact  11280
aaacattcta ctactcactc tcactgccca agaactatca aactcctgag ccaacaactt  11340
aatatgacta gcttacacaa tagctttat agtaaagata cctctttacg gactccactt  11400
atgactccct aaagcccatg tcgaagcccc catcgctggg tcaatagtac ttgccgcagt  11460
actcttaaaa ctaggcggct atggtataat acgcctcaca ctcattctca accccctgac  11520
aaaacacata gcctacccct ccttgtact atccctatga ggcataatta taacaagctc  11580
catctgccta cgacaaacag acctaaaatc gctcattgca tactcttcaa tcagccacat  11640
agccctcgta gtaacagcca ttctcatcca accccctga agcttcaccg gcgcagtcat  11700
tctcataatc gcccacgggc ttacatcctc attactattc tgcctagcaa actcaaacta  11760
cgaacgcact cacagtcgca tcataatcct ctctcaagga cttcaaactc tactcccact  11820
aatagctttt tgatgacttc tagcaagcct cgctaacctc gccttacccc ccactattaa  11880
cctactggga gaactctctg tgctagtaac cacgttctcc tgatcaaata tcactctcct  11940
acttacagga ctcaacatac tagtcacagc cctatactcc ctctacatat ttaccacaac  12000
acaatggggc tcactcaccc accacattaa caacataaaa ccctcattca cacgagaaaa  12060
caccctcatg ttcatacacc tatcccccat tctcctccta tccctcaacc ccgacatcat  12120
taccgggttt tcctcttgta aatatagttt aaccaaaaca tcagattgtg aatctgacaa  12180
cagaggctta cgacccctta tttaccgaga aagctcacaa gaactgctaa ctcatgcccc  12240
catgtctaac aacatggctt tctcaacttt taaaggataa cagctatcca ttggtcttag  12300
gccccaaaaa ttttggtgca actccaaata aaagtaataa ccatgcacac tactataacc  12360
accctaaccc tgacttccct aattccccc atccttacca ccctcgttaa ccctaacaaa  12420
aaaaactcat acccccatta tgtaaaatcc attgtcgcat ccaccttat tatcagtctc  12480 ttccccacaa caatattcat gtgcctagac caagaagtta ttatctcgaa ctgacactga  12540
gccacaaccc aaacaaccca gctctcccta agcttcaaac tagactactt ctccataata  12600
ttcatccctg tagcattgtt cgttacatgg tccatcatag aattctcact gtgatatata  12660
aactcagacc caaacattaa tcagttcttc aaatatctac tcatcttcct aattaccata  12720
ctaatcttag ttaccgctaa caacctattc caactgttca tcggctgaga gggcgtagga  12780
attatatcct tcttgctcat cagttgatga tacgcccgag cagatgccaa cacagcagcc  12840
attcaagcaa tcctatacaa ccgtatcggc gatatcggtt tcatcctcgc cttagcatga  12900
tttatcctac actccaactc atgagaccca caacaaatag cccttctaaa cgctaatcca  12960
agcctcaccc cactactagg cctcctccta gcagcagcag gcaaatcagc ccaattaggt  13020
ctccacccct gactccctc agccatagaa ggccccaccc cagtctcagc cctactccac  13080
tcaagcacta tagttgtagc aggaatcttc ttactcatcc gcttccaccc cctagcagaa  13140
aatagcccac taatccaaac tctaacacta tgcttaggcg ctatcaccac tctgttcgca  13200
gcagtctgcg cccttacaca aaatgacatc aaaaaaatcg tagccttctc cacttcaagt  13260
caactaggac tcataatagt tacaatcggc atcaaccaac cacacctagc attcctgcac  13320
```

```
atctgtaccc acgccttctt caaagccata ctatttatgt gctccgggtc catcatccac  13380
aaccttaaca atgaacaaga tattcgaaaa ataggaggac tactcaaaac catacctctc  13440
acttcaacct ccctcaccat tggcagccta gcattagcag gaatacccttt cctcacaggt  13500 ttctactcca aagaccacat catcgaaacc gcaaacatat catacacaaa cgcctgagcc  13560
ctatctatta ctctcatcgc tacctccctg acaagcgcct atagcactcg aataattctt  13620 ctcacccta caggtcaacc tcgcttcccc accttacta acattaacga aaataacccc  13680
accctactaa accccattaa acgcctggca gccggaagcc tattcgcagg atttctcatt  13740
actaacaaca tttcccccgc atcccccttc caaacaacaa tccccctcta cctaaaactc  13800
acagccctcg ctgtcacttt cctaggactt ctaacagccc tagacctcaa ctacctaacc  13860
aacaaactta aaataaaatc cccactatgc acattttatt tctccaacat actcggattc  13920
taccctagca tcacacaccg cacaatcccc tatctaggcc ttcttacgag ccaaaacctg  13980
cccctactcc tcctagacct aacctgacta gaaaagctat tacctaaaac aatttcacag  14040
caccaaatct ccacctccat catcacctca acccaaaaag gcataattaa acttacttc  14100 ctctctttct tcttcccact catcctaacc ctactcctaa tcacataacc tattcccccg  14160
agcaatctca attacaatat atacaccaac aaacaatgtt caaccagtaa ctactactaa  14220
tcaacgccca taatcataca aagccccgc accaatagga tcctcccgaa tcaaccctga  14280
cccctctcct tcataaatta ttcagcttcc tacactatta aagtttacca caaccaccac  14340
cccatcatac tctttcaccc acagcaccaa tcctacctcc atcgctaacc ccactaaaac  14400
actcaccaag acctcaaccc ctgaccccca tgcctcagga tactcctcaa tagccatcgc  14460
tgtagtatat ccaaagacaa ccatcattcc ccctaaataa attaaaaaaa ctattaaacc  14520
catataacct cccccaaaat tcagaataat aacacacccg accacaccgc taacaatcaa  14580
tactaaaccc ccataaatag gagaaggctt agaagaaaac cccacaaacc ccattactaa  14640
acccacactc aacagaaaca aagcatacat cattattctc gcacggacta caaccacgac  14700
caatgatatg aaaaaccatc gttgtatttc aactacaaga acaccaatga cccccaatacg  14760 caaaactaac cccctaataa aattaattaa ccactcattc atcgacctcc ccacccccatc  14820 caacatctcc gcatgatgaa acttcggctc actccttggc gcctgcctga tcctccaaat  14880
caccacagga ctattcctag ccatgcacta ctcaccagac gcctcaaccg cctttcatc  14940 aatcgcccac atcactcgag acgtaaatta tggctgaatc atccgctacc ttcacgccaa  15000
tggcgcctca atattcttta tctgcctctt cctacacatc gggcgaggcc tatattacgg  15060
atcatttctc tactcagaaa cctgaaacat cggcattatc ctcctgcttg caactatagc  15120 aacagcttc ataggctatg tcctcccgtg aggccaaata tcattctgag gggccacagt  15180
aattacaaac ttactatccg ccatcccata cattgggaca gacctagttc aatgaatctg  15240
aggaggctac tcagtagaca gtcccaccct cacacgattc tttacctttc acttcatctt  15300
gcccttcatt attgcagccc tagcaacact ccacctccta ttcttgcacg aaacgggatc  15360
aaacaacccc ctaggaatca cctcccattc cgataaaatc accttccacc cttactacac  15420
aatcaaagac gccctcggct tacttctctt ccttctctcc ttaatgacat taacactatt  15480
ctcaccagac ctcctaggcg acccagacaa ttatacccta gccaaccct taaacacccc  15540 tccccacatc aagcccgaat gatatttcct attcgcctac acaattctcc gatccgtccc  15600
taacaaacta ggaggcgtcc ttgccctatt actatccatc ctcatcctag caataatccc  15660
catcctccat atatccaaac aacaaagcat aatatttcgc ccactaagcc aatcacttta  15720
```

-continued

```
ttgactccta gccgcagacc tcctcattct aacctgaatc ggaggacaac cagtaagcta    15780 ccctttacc  atcattggac aagtagcatc cgtactatac ttcacaacaa tcctaatcct    15840
aataccaact atctccctaa ttgaaaacaa aatactcaaa tgggcctgtc cttgtagtat    15900
aaactaatac accagtcttg taaaccggag atgaaaacct ttttccaagg acaaatcaga    15960
gaaaaagtct ttaactccac cattagcacc caaagctaag attctaattt aaactattct    16020
ctgttctttc atggggaagc agatttgggt accacccaag tattgactca cccatcaaca    16080
accgctatgt atttcgtaca ttactgccag ccaccatgaa tattgtacgg taccataaat    16140
acttgaccac ctgtagtaca taaaaaccca atccacatca aaaccccctc cccatgctta    16200
caagcaagta cagcaatcaa ccctcaacta tcacacatca actgcaactc caaagccacc    16260
cctcacccac taggatacca acaaacctac ccacccttaa cagtacatag tacataaagc    16320
catttaccgt acatagcaca ttacagtcaa atcccttctc gtccccatgg atgaccccccc    16380 tcagataggg gtcccttgac caccatcctc cgtgaaatca atatcccgca caagagtgct    16440
actctcctcg ctccgggccc ataacacttg ggggtagcta aagtgaactg tatccgacat    16500
ctggttccta cttcagggtc ataaagccta aatagcccac acgttcccct taaataagac    16560
atcacgatg                                                              16569
```

<210> SEQ ID NO 2
<211> LENGTH: 25
<212> TYPE: DNA
<213> ORGANISM: Artificial Sequence
<220> FEATURE:
<223> OTHER INFORMATION: specific template sequence for the amplicon
      D-loop

<400> SEQUENCE: 2
tagggggttt tgattatta ttttt                                              25

<210> SEQ ID NO 3
<211> LENGTH: 30
<212> TYPE: DNA
<213> ORGANISM: Artificial Sequence
<220> FEATURE:
<223> OTHER INFORMATION: Specific template sequence for the amplicon
      D-loop

<400> SEQUENCE: 3
acaaacattc aattattatt attatatcct                                        30

<210> SEQ ID NO 4
<211> LENGTH: 30
<212> TYPE: DNA
<213> ORGANISM: Artificial Sequence
<220> FEATURE:
<223> OTHER INFORMATION: Specific template sequence for the amplicon ND1

<400> SEQUENCE: 4
atggttaatt ttttattttt tattgtattt                                        30

<210> SEQ ID NO 5
<211> LENGTH: 30
<212> TYPE: DNA
<213> ORGANISM: Artificial Sequence
<220> FEATURE:
<223> OTHER INFORMATION: Specific template sequence for the amplicon ND1

<400> SEQUENCE: 5

```
taatttaaat ttaatactca ccctaatcaa                                               30

<210> SEQ ID NO 6
<211> LENGTH: 10
<212> TYPE: DNA
<213> ORGANISM: Artificial Sequence
<220> FEATURE:
<223> OTHER INFORMATION: MID sequence

<400> SEQUENCE: 6
acgagtgcgt                                                                     10

<210> SEQ ID NO 7
<211> LENGTH: 10
<212> TYPE: DNA
<213> ORGANISM: Artificial Sequence
<220> FEATURE:
<223> OTHER INFORMATION: MID sequence

<400> SEQUENCE: 7
acgctcgaca                                                                     10

<210> SEQ ID NO 8
<211> LENGTH: 10
<212> TYPE: DNA
<213> ORGANISM: Artificial Sequence
<220> FEATURE:
<223> OTHER INFORMATION: MID sequence

<400> SEQUENCE: 8
agacgcactc                                                                     10

<210> SEQ ID NO 9
<211> LENGTH: 10
<212> TYPE: DNA
<213> ORGANISM: Artificial Sequence
<220> FEATURE:
<223> OTHER INFORMATION: MID sequence

<400> SEQUENCE: 9
agcactgtag                                                                     10

<210> SEQ ID NO 10
<211> LENGTH: 10
<212> TYPE: DNA
<213> ORGANISM: Artificial Sequence
<220> FEATURE:
<223> OTHER INFORMATION: MID sequence

<400> SEQUENCE: 10
atcagacacg                                                                     10

<210> SEQ ID NO 11
<211> LENGTH: 10
<212> TYPE: DNA
<213> ORGANISM: Artificial Sequence
<220> FEATURE:
<223> OTHER INFORMATION: MID sequence

<400> SEQUENCE: 11
atatcgcgag                                                                     10

<210> SEQ ID NO 12
<211> LENGTH: 10
<212> TYPE: DNA
<213> ORGANISM: Artificial Sequence
```

```
<220> FEATURE:
<223> OTHER INFORMATION: MID sequence

<400> SEQUENCE: 12
cgtgtctcta                                                                  10

<210> SEQ ID NO 13
<211> LENGTH: 10
<212> TYPE: DNA
<213> ORGANISM: Artificial Sequence
<220> FEATURE:
<223> OTHER INFORMATION: MID sequence

<400> SEQUENCE: 13
ctcgcgtgtc                                                                  10

<210> SEQ ID NO 14
<211> LENGTH: 10
<212> TYPE: DNA
<213> ORGANISM: Artificial Sequence
<220> FEATURE:
<223> OTHER INFORMATION: MID sequence

<400> SEQUENCE: 14
tagtatcagc                                                                  10

<210> SEQ ID NO 15
<211> LENGTH: 10
<212> TYPE: DNA
<213> ORGANISM: Artificial Sequence
<220> FEATURE:
<223> OTHER INFORMATION: MID sequence

<400> SEQUENCE: 15
tctctatgcg                                                                  10

<210> SEQ ID NO 16
<211> LENGTH: 10
<212> TYPE: DNA
<213> ORGANISM: Artificial Sequence
<220> FEATURE:
<223> OTHER INFORMATION: MID sequence

<400> SEQUENCE: 16
tgatacgtct                                                                  10

<210> SEQ ID NO 17
<211> LENGTH: 10
<212> TYPE: DNA
<213> ORGANISM: Artificial Sequence
<220> FEATURE:
<223> OTHER INFORMATION: MID sequence

<400> SEQUENCE: 17
tactgagcta                                                                  10

<210> SEQ ID NO 18
<211> LENGTH: 10
<212> TYPE: DNA
<213> ORGANISM: Artificial Sequence
<220> FEATURE:
<223> OTHER INFORMATION: MID sequence

<400> SEQUENCE: 18
catagtagtg                                                                  10
```

```
<210> SEQ ID NO 19
<211> LENGTH: 10
<212> TYPE: DNA
<213> ORGANISM: Artificial Sequence
<220> FEATURE:
<223> OTHER INFORMATION: MID sequence

<400> SEQUENCE: 19
cgagagatac                                                          10

<210> SEQ ID NO 20
<211> LENGTH: 10
<212> TYPE: DNA
<213> ORGANISM: Artificial Sequence
<220> FEATURE:
<223> OTHER INFORMATION: MID sequence

<400> SEQUENCE: 20
atacgacgta                                                          10

<210> SEQ ID NO 21
<211> LENGTH: 10
<212> TYPE: DNA
<213> ORGANISM: Artificial Sequence
<220> FEATURE:
<223> OTHER INFORMATION: MID sequence

<400> SEQUENCE: 21
tcacgtacta                                                          10

<210> SEQ ID NO 22
<211> LENGTH: 10
<212> TYPE: DNA
<213> ORGANISM: Artificial Sequence
<220> FEATURE:
<223> OTHER INFORMATION: MID sequence

<400> SEQUENCE: 22
cgtctagtac                                                          10

<210> SEQ ID NO 23
<211> LENGTH: 10
<212> TYPE: DNA
<213> ORGANISM: Artificial Sequence
<220> FEATURE:
<223> OTHER INFORMATION: MID sequence

<400> SEQUENCE: 23
tctacgtagc                                                          10

<210> SEQ ID NO 24
<211> LENGTH: 10
<212> TYPE: DNA
<213> ORGANISM: Artificial Sequence
<220> FEATURE:
<223> OTHER INFORMATION: MID sequence

<400> SEQUENCE: 24
tgtactactc                                                          10

<210> SEQ ID NO 25
<211> LENGTH: 10
<212> TYPE: DNA
<213> ORGANISM: Artificial Sequence
<220> FEATURE:
<223> OTHER INFORMATION: MID sequence
```

```
<400> SEQUENCE: 25
acgactacag                                                          10

<210> SEQ ID NO 26
<211> LENGTH: 10
<212> TYPE: DNA
<213> ORGANISM: Artificial Sequence
<220> FEATURE:
<223> OTHER INFORMATION: MID sequence

<400> SEQUENCE: 26
cgtagactag                                                          10

<210> SEQ ID NO 27
<211> LENGTH: 10
<212> TYPE: DNA
<213> ORGANISM: Artificial Sequence
<220> FEATURE:
<223> OTHER INFORMATION: MID sequence

<400> SEQUENCE: 27
tacgagtatg                                                          10

<210> SEQ ID NO 28
<211> LENGTH: 10
<212> TYPE: DNA
<213> ORGANISM: Artificial Sequence
<220> FEATURE:
<223> OTHER INFORMATION: MID sequence

<400> SEQUENCE: 28
tactctcgtg                                                          10

<210> SEQ ID NO 29
<211> LENGTH: 10
<212> TYPE: DNA
<213> ORGANISM: Artificial Sequence
<220> FEATURE:
<223> OTHER INFORMATION: MID sequence

<400> SEQUENCE: 29
tagagacgag                                                          10

<210> SEQ ID NO 30
<211> LENGTH: 502
<212> TYPE: DNA
<213> ORGANISM: Homo sapiens

<400> SEQUENCE: 30
ataccaacaa acctacccac ccttaacagt acatagtaca taaagccatt taccgtacat    60
agcacattac agtcaaatcc cttctcgtcc ccatggatga ccccccctcag ataggggtcc   120 cttgaccacc atcctccgtg aaatcaatat cccgcacaag agtgctactc tcctcgctcc   180
gggcccataa cacttggggg tagctaaagt gaactgtatc cgacatctgg ttcctacttc   240
agggtcataa agcctaaata gcccacacgt tcccttaaa taagacatca cgatggatca    300
caggtctatc accctattaa ccactcacgg gagctctcca tgcatttggt attttcgtct    360
ggggggtatg cacgcgatag cattgcgaga cgctggagcc ggagcaccct atgtcgcagt    420
atctgtcttt gattcctgcc tcatcctatt atttatcgca cctacgttca atattacagg    480
cgaacatact tactaaagtg tg                                            502
```

```
<210> SEQ ID NO 31
<211> LENGTH: 22
<212> TYPE: DNA
<213> ORGANISM: Artificial Sequence
<220> FEATURE:
<223> OTHER INFORMATION: primer forward to detect polymorphism T16519C

<400> SEQUENCE: 31
ataccaacaa acctacccac cc                                              22

<210> SEQ ID NO 32
<211> LENGTH: 24
<212> TYPE: DNA
<213> ORGANISM: Artificial Sequence
<220> FEATURE:
<223> OTHER INFORMATION: primer reverse to detect polymorphism T16519C

<400> SEQUENCE: 32
ggcgaacata cttactaaag tgtg                                            24

<210> SEQ ID NO 33
<211> LENGTH: 21
<212> TYPE: DNA
<213> ORGANISM: Artificial Sequence
<220> FEATURE:
<223> OTHER INFORMATION: Primer A

<400> SEQUENCE: 33
cgtatcgcct ccctcgcgcc a                                               21

<210> SEQ ID NO 34
<211> LENGTH: 21
<212> TYPE: DNA
<213> ORGANISM: Artificial Sequence
<220> FEATURE:
<223> OTHER INFORMATION: Primer B

<400> SEQUENCE: 34
ctatgcgcct tgccagcccg c                                               21
```